United States Patent [19]
Fluhr et al.

[11] Patent Number: 6,100,449
[45] Date of Patent: Aug. 8, 2000

[54] TRANSGENIC TOMATO PLANTS CONTAINING A FUSARIUM RESISTANCE GENE

[75] Inventors: Robert Fluhr, Rehovot; Yuval Eshed; Naomi Ori, both of Yavne; Ilan Paran, Carmei Yossef; Daniel Zamir, Gedera, all of Israel

[73] Assignees: Yeda Research and Development Co. Ltd., Rehovot; Yissum Research and Development Company, Jerusalem, both of Israel

[21] Appl. No.: 08/930,996

[22] PCT Filed: Apr. 15, 1996

[86] PCT No.: PCT/US96/05272

§ 371 Date: Dec. 9, 1997

§ 102(e) Date: Dec. 9, 1997

[87] PCT Pub. No.: WO96/32007

PCT Pub. Date: Oct. 17, 1996

[30] Foreign Application Priority Data

Apr. 13, 1995 [IL] Israel .......................................... 113373

[51] Int. Cl.⁷ .............................. C12N 15/29; C12N 5/04; C12N 15/82; A01H 5/00
[52] U.S. Cl. ........................ 800/279; 435/69.1; 435/70.1; 435/440; 435/468; 435/469; 435/474; 435/410; 435/419; 435/320.1; 536/23.1; 536/23.6; 536/23.3; 800/278; 800/290; 800/317.4
[58] Field of Search .................................... 800/278, 279, 800/317.4, 290; 536/23.6, 23.1, 23.3; 435/69.1, 70.1, 440, 468, 469, 474, 410, 419, 320.1

[56] References Cited

U.S. PATENT DOCUMENTS 5,437,697  8/1995  Sebastian et al. .
5,530,187  6/1996  Lamb et al. .

FOREIGN PATENT DOCUMENTS

WO 96/06731  3/1995  WIPO .
9706259  2/1997  WIPO .

OTHER PUBLICATIONS

Napoli et al. The Plant Cell. 1989. vol. 2: 278–289.
Carvalho et al. The EMBO J. 1992. vol. 11: 2995–2602.
Lepiniec et al. Plant Molecular Biology. 1992. vol. 19: 339–342.
A.F. Bent et al., "RPS2 of Arabidopsis Thaliana: A Leucine–Rich Repeat Class of Plant Disease Resistance Genes", Science, vol. 265, pp. 1856–1860, Sep. 23, 1994.
B.L. Bournival et al., "Genetic Analysis of Resistances to Races 1 and 2 of Fusarium Oxysporum f. sp. lycopersici From the Wild Tomato Lycopersicon Pennellii", Theor. Appl. Genet., vol. 79, pp. 641–645, 1990.
D.A. Jones et al., "Isolation of the Tomato Cf–9 Gene for Resistance to Cladosporium Fulvum by Transposon Tagging", Science, vol. 266, pp. 789–793, Nov. 4, 1994.

G.J. Lawrence et al., "The L6 Gene for FLax Rust Resistance is Related to the Arabidopsis Bacterial Resistance Gene RPS2 and the Tobacco Viral Resistance Gene N", The Plant Cell, vol. 7, pp. 1195–1206, 1995.
M. Mindrinos et al., "The A. Thaliana Disease Resistance Gene RPS2 Encodes a Protein Containing a Neucleotide–Binding Site and Leucine–Rich Repeats", Cell, vol. 78, pp. 1089–1099, Sep. 23, 1994.
G. Segal et al., "Correlation of Genetic and Physical Structure in the Region Surrounding the $I_2$ Fusarium Oxysporum Resistance Locus in Tomato", Mol. Gen. Genet., vol. 231, pp. 179–185, 1992.
S. Whitman et al., "The Product of the Tobacco Mosaic Virus Resistance Gene N: Similarity to Toll and the Interleukin–1 Receptor", Cell, vol. 78, pp. 1101–1115, Sep. 23, 1994.
H. Röhrig et al., "Growth of Tobacco Protoplasts Stimulated by Synthetic Lipo–Chitooligosaccharides", Science, vol. 269, pp. 841–846, Aug. 11, 1995.
M.S. Dixon et al., "The Tomato Cf–2 Disease Resistance Locus Comprises Two Functional Genes Encoding Leucine Rich Repeat Protiens", Cell, vol. 84, pp. 451–459, Feb. 9, 1996.
N. Ori et al., "The 12C Family From the Wilt Disease Resistance Locus I2 Belongs to the Neucleotide Binding, Leucine–Rich Repeat Superfamily of Plant Resistance Genes", The Plant Cell, vol. 9, pp. 521–532, Apr. 1997.
Sarfatti, M. et al., "RFLP mapping of I1, a new locus in tomato conferring resistance against Fusarium oxysporum f. sp. lycopersici race 1.", Theor. Appl. Genet., vol. 82, pp. 22–26 (1991).
Bournival, B.L. et al., "An isozyme marker for resistance to race 3 of Fusarium oxysporum f. sp. lycopersici in tomato.", Theor. Appl. Genet., vol. 78, pp. 489–494 (1989).
Bournival, B.L. et al., "New sources of genetic resistance to race 3 fusarium wilt of tomato.", Plant Disease, vol. 75, No. 3, pp. 281–284 (1991).
Staskawicz, Brian et al., "Molecular genetics of plant disease resistance.", Science, vol. 268, pp. 661–667 (1995).
Chasen, R., "Plant–Pathogen Encounters in Edinburgh" *The Plant Cell* 6:1332–1341 (1994) & 7th Int'l Symposium on Molecular Plant–Microbe Interactions, held Jun. 26–Jul. 1, 1994, in Edinburgh.

(List continued on next page.)

*Primary Examiner*—Lynette R. F. Smith
*Assistant Examiner*—Ohsama M-Faiz Zaghmout
*Attorney, Agent, or Firm*—Browdy and Neimark

[57] ABSTRACT

The invention provides genes from the I2 Fusarium resistance locus of tomato belonging to a multigene family herein designated I2C. The DNA molecules of the invention are useful as a tomato resistance gene to plant vascular diseases caused by Fusarium pathogens, particularly *Fusarium oxysporium* f.sp. *lycopersici* race 2, or as probes for breeding Fusarium-resistant tomato lines or for screening of news diseases in plants of the Solanaceae family. Further provided are Fusarium-resistant tomato lines transformed by an I2C resistance gene of the invention.

10 Claims, 18 Drawing Sheets

OTHER PUBLICATIONS de Wit, PJGM, "Cold Spring Harbor conference on 'Molecular biology of disease reistance genes in plants'", *Molecular Breeding* 1:203–206 (1995); meeting held Apr. 9–12, 1995.

Drouin et al, "A plant processed pseudogene", *Nature* 328:557–558 (1987).

Keen, N.T., "The molecular biology of disease resistance", *Plant Molecular Biology* 19:109–122 (1992).

Lamb et al, "Emerging Strategies for Enhancing Crop Resistance to Microbial Pathogens", *Bio/Technology* 10:1436–1445 (1992).

Ori et al, "A genomic search for the gene conferring resistance to fusarium wilt in tomato", *Euphytica* 79(3):201–204 (1994).

Tanksley et al, "RFLP Mapping in Plant Breeding: New tools for an Old Science", *Bio/Technology* 7:1436–1445 (1992).

Tanksley et al, "Chromosome Landing: a paradigm for map–based gene cloning in plants with large genomes", *Trends in Genetics* 11(2):63–68 (1995).

van den Elzen et al, "Virus and fungal resistance: from laboratory to field", *Phil. Trans. R. Soc. Lond. Biol. Sci.* 342:271–278 (1993).

GENETIC MAP OF CHROMOSOME 11

MAP DISTANCE (cM)

PHYSICAL MAP OF YAC 340-63

```
 -298  ATCTCAACTCTTCACAATTCTAAAATGTATTGATTATATGGTAGGCCCCACTACAATGAGCTGTTGAAAAATGGACTCAATTATTCTATTCAAGTCAATACTTTTGAGA
 -188  AGAGAAAAGAGGACAGTTTGATTAGCTGAAAAATAGTTGTACTAATTTCAAGCAATCACTACTATTCTTGTTGCAAATTACTTCTCAACATTCAACGGGTAAAGTGAA
  -78  GTACTATCTTGTAGTGAAGATAGAWAGAAAAAATTTATCTTCAAATCATTTGTGTTCCCTTGCAGATTTGAGAAATGGAGATTGGGTTAGCAATTGGTGTGTGCAT
                                                                              M  E  I  G  L  A  I  G  A  F
   32  TTCTCTCCTCAGCTTTGAATGTTCTGTTGATAGGCTTGCTCAACATGTTCCGAAGCATACGATGATGTTGAGCTCTTTGAGAAGCTGGGG
        L  S  S  A  L  N  V  L  F  D  R  L  A  P  N  G  D  L  L  N  M  F  R  K  H  T  D  D  V  E  L  F  E  K  L  G
  142  GACATTTGCTTAGTCTTCAAATTGCTAAGTGCAGAGAATAAGAAGCATCAATTGTGAGCCAGTGGTTACATAAGCTTCAGACTGCTCTGGACGCTGC
        D  I  L  L  S  L  Q  I  V  L  S  D  A  E  N  K  K  A  S  N  Q  F  V  S  Q  W  L  H  K  L  Q  T  A  V  D  A  A
  252  TGAAAACTTGATAGAACAAGTCAATTATGAAGCTTTGAGGCTTAAAGTGGAACAACCAGCAAGTAAGCAACCTGTCTGAGTGATGATTCTTTCTTA
        E  N  L  I  E  Q  V  N  Y  E  A  L  R  L  K  V  E  T  S  N  Q  Q  V  S  D  L  N  L  C  L  S  D  D  F  F  L  N
  362  ACATAAAGAAGAAGTTGGAAGACACTATTAAAAAACTGGAGGTGTTGGAAAAGCAAATTGGTCGCGTTGGCCTTAAAGGAGCATTTTATTCGACCAAACAAGAAACTAGA
        I  K  K  E  D  T  I  K  K  L  E  V  L  E  K  Q  I  G  R  L  G  L  K  E  H  F  I  S  T  K  Q  E  T  R
  472  ACACCTTTCAACTTCTTGGTTGATGATTCTGGTATCTTTGGAAGGAAGAATGAAGAATAGAGAATTTGGTTGGCCGTTTGTTGTCTATGATACAAAGCGAAAAATCTGGC
        T  P  S  T  S  L  V  D  D  S  G  I  F  G  R  K  N  E  I  E  N  L  V  G  R  L  L  S  M  D  T  K  R  K  N  L  A
  582  TGTAGTTCCTATTGTGGGAATGGGCGGCATGGGTAAGACAACACTTGCTAAAGCCGTTTACAATGATGAGAGTGCAGAAACATTTTGGTTTGACAGCTTGGTTTTGTG
        V  V  P  I  V  G  M  G  G  M  G  K  T  L  A  K  A  V  Y  N  D  E  R  V  Q  K  H  F  G  L  T  A  W  F  C  V
  692  TTTCTGAGGCATGATGCTTTCAGAATAGCCTTTCAAGAAGTTTACTTCAAGAAAAGCTGAATGACGGTTCTTGTCTTGATGACGTGTGGAATGATAATTATCCTGAGTGGGA
        S  E  A  Y  D  A  F  R  I  P  K  G  L  L  Q  E  I  G  S  T  D  L  K  A  D  D  N  L  N  Q  L  V  K  L  K
  802  GCTGATGACAATCTTAATGCTACAAGTCAAATTGAAGCAAAGCTAAGATCATTGTAACGACACGTAAAGAGAGTGTTGCCTTGATGATGATAGTGGGCAATCTACATGGGAA
        A  D  D  N  L  N  Q  L  V  K  L  K  E  K  L  N  G  K  R  F  L  V  V  L  D  D  V  W  N  D  N  Y  P  E  W  D
  912  TGACTTGAGAAATCTTTTTACAAGGGGATATAGGCATCTTCAAAGAAGTAAGATCATTGAGACGAAGATCCCAAGGAACATCCAGAATTTGAAGAGGTTGGAAAACAAATTGCAGACAAG
        D  L  R  N  L  F  L  Q  G  D  I  G  S  K  I  V  T  T  R  K  E  S  V  A  L  M  M  D  S  G  A  I  Y  M  G  I
 1022  TTCTGTCTAGTGAAGACTCCTTGGCTCTATTCAAACGACATTCATTAGAGCAACAAGATCCAAGGTTGACCAGCAAATCAGAGGTGGATGAGTGAGATATGGGAGCTTCCAAG
        L  S  S  E  D  S  W  A  L  F  K  R  H  S  L  E  H  K  D  P  K  E  H  Q  E  F  E  E  V  G  K  Q  I  A  D  K
 1132  TGCAAAGGGTTGCCTTTAGCTCTAAAAGCACTTGCTGGTATGTTACCAGCAATCATGATCTCCCTGCACATTAAAGCAATGTTGGCTTATTGTCAATATATCCAAAGATTATCAATTTC
        C  K  G  L  P  L  A  L  K  A  L  A  G  M  L  R  S  K  S  E  V  D  E  W  R  N  I  L  R  S  E  I  W  E  L  P  S
 1242  TTGTTCGAATGGTATATTACCAGCGTAATGTGAGCTACAAGTTTCATTCGGTAACCAATCAGTTTCATTCGGGTAACCAATCAGTGTTTCATTCTTATCGAGATCAAGATCATTGTTCGAAATGGCC
        C  S  N  G  I  L  P  A  H  L  K  Q  C  L  A  Y  C  A  I  Y  P  K  D  Y  Q  F  R
 1352  GCAAAGAGCAAGTTATTCACCTGTGGATTGCTAAGTGCCAAATGCTAAGTCGGCCAATCAGTTTCATTCGGGTAACCAATTGGCACAAATTGGCACAAATCATTGTATAAGGTTGAAGATAACAAAGG
        K  E  Q  V  I  H  L  W  I  A  N  G  L  V  H  Q  F  H  S  G  N  Q  Y  F  I  E  L  R  S  L  F  E  M  A
 1462  TCAGAGCCCTTCTGAAAGAGACGTAGAGAATTCTTAATGCATGACCTTGTCATGATTTGCAATGATGCACAAGATGTGAGTTTGAGGTGATGTGAGGACAATTACTTC
        S  E  P  S  E  R  D  V  E  E  F  L  M  H  D  L  V  N  D  L  A  Q  I  A  S  S  N  H  C  I  R  L  E  D  N  K  G
 1572  ATCGCATATGTTGGAACAATGTCGGCACATGTCCTATTCAATAGACAAGATGTGAGTTTGAGTTTAAATCACTCTTTAAATCAGAGCAGCTGAGGACATTACTTC
        S  H  M  L  E  Q  C  R  H  M  S  Y  S  I  G  Q  D  G  E  F  F  E  K  L  K  S  L  F  K  S  E  Q  L  R  T  L  L  P
```

FIG. 4B

```
1682 CAATCGATATCCAGTTCCATTACTCAAAAAAACTAAGCAAGAGGGTGTTGCATAACTACTGCCTACACTAGATCCTTGAGGGCACTATCATTGTCTCATTACCAGATT
      I  D  I  Q  F  H  Y  S  K  K  L  S  K  R  V  L  H  N  I  L  P  T  L  R  S  L  R  A  L  S  L  S  H  Y  Q  I

1792 GAGGTGTTGCCAAATGACTTGTTATCAAATTAAAGCTCCCTCAGATTTTGGACCTTTCTGAGACATGCCGATTACAAAGTTGCCGGATTCCATTTTGTGTTGTATAACTT
      E  V  L  P  N  D  L  F  I  K  L  K  L  L  R  F  L  D  L  S  E  T  S  I  T  K  L  .  R  .  D  .  S  .  .  I  .  F  .  V  .  .  L  .  Y  .  .  N  .  L

1902 AGAGACACTTCTCCTGTCATCTGTGAATATCTTGAGGAGTACCGCTGCAGATGGAGAAGTTGATTAACTTGCGTCATCTTGACATAAGCAACACTCGGCGCTTGAAGA
      .  E  .  T  .  .  L  .  .  L  .  .  S  .  .  C  .  .  E  .  Y  .  .  L  E  E  L  P  L  Q  M  E  K  L  I  N  L  R  H  L  D  I  S  N  T  R  R  L  K  I

2012 TCCCACTACATCTGAGCAGGTTGAAAAGCCTCCAAGTTCTTGTAGGTGGTTGGGAGCCAAGTTCTTGTAGGTGTTGAGAATATTTGGGTGAAGCACCAACTTATATGGA
      P  L  H  L  S  R  L  K  S  L  Q  V  L  V  G  A  K  F  L  V  G  G  W  R  M  E  Y  L  G  E  A  P  N  L  Y  G

2122 TCTCTATCAATTCTAGAGTTGGAAAATGTGGTTGATAGAAGGGAAGCTGTGAAGCAAAGATGAGGGAGAAGAATCATGTTGAGCAATTATCATTGGAGTGAGTGAAAG
      S  L  S  I  L  E  L  E  N  V  V  D  R  R  E  A  V  K  A  K  M  R  E  K  N  H  V  E  Q  L  S  L  E  W  S  E  S

2232 CATTAGTGCTGACAATTCACAAACAGAGACATACTTGATGAGCTACGCCCACATAAAGCAGTTGAAATCACTGGATATAGAGGGACAAACTTTCCAA
      S  L  S  I  L  E  L  E  N  V  V  D  R  R  E  A  V  K  A  K  M  R  E  K  N  H  V  E  Q  L  S  L  E  W  S  E  S

2232 CATTAGTGCTGACAATTCACAAACAGAGACATACTTGATGAGCTACGCCCACATAAAGCAGTTGAAATCACTGGATATAGAGGGACAAACTTTCCAA
      I  S  A  D  N  S  Q  T  E  R  D  I  L  D  E  L  R  P  H  K  N  I  K  A  V  E  I  T  G  Y  R  G  T  N  F  P  N

2342 ACTGGGTAGCTGATCCTTTGTTTGTTAAGCTGGTGCATTGTATCTTAGAAACTGCAAGGACTGTTACTCCTTGCCAGCACTGTTAACTCTCTTGTGAAGCTTAGATTTGAAGATATGCC
      W  V  A  D  P  L  F  V  K  L  V  H  L  Y  L  R  N  C  K  D  C  Y  S  L  P  A  L  G  Q  L  P  C  L  E  F  L

2452 TCCATTAGAGGGATGCATGGATAGAGTGGTGACAGAAGAGTTCTATGGCAGATTGTCCTCCAAAAGCCTTTAACTCTCTTGTGAAGCTTAGATTTGAAGATATGCC
      S  I  R  G  M  H  G  I  R  V  V  T  E  E  Y  G  R  L  S  S  K  K  P  F  N  S  L  V  K  L  R  F  E  D  M  P

2562 TGAATGGAAGCAATGGCACACACTAGGAATTGAGAGTTCCCTACACTTGAGAGAGTTCCCTACACTTGAGAGAATAAAGATATCTGGTTGCCCAAAATTGAAA
      E  W  K  O  W  H  T  L  G  I  E  F  Q  T  L  E  K  L  S  I  K  N  C  P  E  L  S  L  E  I  P  I  Q  F  S  S

2672 GTTTAAAAAGGTTAGATATGTGATTGTAAGTCTGTGATGATTTGAGTGATATTGAGTCTGTGTAGATATCACCTGAGTTTCTCCCAACAGCACGTCATTGAGTAT
      L  K  R  L  D  I  C  D  C  K  S  V  T  S  F  Q  F  S  I  L  P  T  T  L  K  R  I  K  I  S  G  C  P  K  L  K

2782 TTGGAGGCGCCAGTTGGTGAGATGTTTGTGGAGTATTTGATTCCTACTGCCCACTGAAAGTCTCCATATTCGGAATTGTGAAAACTCGGAGGAGCGGGCCAGCTGA
      L  E  A  P  V  G  E  M  F  V  E  Y  L  S  V  I  D  C  G  C  V  D  D  I  S  P  F  F  L  P  T  A  R  Q  L  S  I

2892 TGAGAATTGCCACAACGTTACTAGGTTTTTGATTCCTACTGCCCACTGAAAGTCTCCATATTCGGAATTGTGAAAACTCGGAGGAGCGGGCCAGCTGA
      E  N  C  H  N  V  T  R  F  L  I  P  T  A  T  E  S  L  H  I  R  N  C  E  K  L  S  M  A  C  G  G  A  Q  L  T

3002 CGTCACTGAATATTTGGGGATGTAAGAAGCTCAAGTGTCTTCCAGAAACTCCGACTATTGTCCAGAAGTTATGGATCAAACATGATGGGAGTGA
      S  L  N  I  W  G  C  K  K  L  K  C  L  P  E  L  L  P  S  L  K  E  L  R  L  T  Y  C  P  E  I  E  G  E  L  P

3112 TTCAATTTACAAATACTCGATATGCCAAGAACATCAGATATTGCAAGAAATGCAAGACTATTCATTCAATCATTCATTAAGAACATTAAGCAGCCAACATCTCAAAAGCCTCACCTCTTCAATTC
      F  N  L  Q  I  L  D  I  R  Y  C  K  K  L  V  N  G  R  K  E  W  H  L  Q  R  L  T  E  L  W  I  K  H  D  G  S  D

3222 CGAACATATTGAACATTGGGAGTTGCCTCTATTCAGAGACTTGCCTTCCAACATTCAAAATTAAGCAACATTCATATCATCAACATTAAGCAGCCAACATCTCAAAAGCCTCACCTCTTCAATTC
      F  N  L  Q  I  L  D  I  R  Y  C  K  K  L  V  N  G  R  K  E  W  H  L  Q  R  L  T  E  L  W  I  K  H  D  G  S  D

3222 CGAACATATTGAACATTGGGAGTTGCCTCTATTCAGAGACTTGCCTTCCAACATTCAAAATTAAGCAACATTCATATCATCAACATTAAGCAGCCAACATCTCAAAAGCCTCACCTCTTCAATTC
      E  H  I  E  H  W  E  L  P  S  S  I  Q  R  L  F  I  F  N  L  K  T  L  S  S  Q  H  L  K  S  L  T  S  L  Q  F  L

3332 TACGTATTGTTGGTAATTATCTCAGTTTCAGTGACGTTCAGTGACGTTCAGTGCCAACTTCTCACCTCACTCGCTTCAAAATCTACAAATCTGGAATTCTTAATCTTCAA
      R  I  V  G  N  L  S  Q  F  Q  S  Q  G  Q  L  S  S  F  S  H  L  T  S  L  Q  T  L  Q  I  W  N  E  L  N  L  Q
```

```
3442 TCACTACTGAATCAGCACTGCCCTCCTCCCTCTCTCACCTGATCATCTCCAATCCCTTCCATTAAAGGGATGCCCTCTTCCCTCTTCTACACT
      S  L  P  E  S  A  L  P  S  S  L  S  H  L  I  S  N  C  P  N  L  Q  S  L  P  L  K  G  M  P  S  L  S  T  L
3552 ATCAATTTCCAAATGTCCATTGCTCACACCTACTAGAATTGACAAGGGGAATACTGGACAGAAATGCTCATATCCCACCATACAGATCGATGAGGAATGCATGT
      S  I  S  K  C  P  L  L  T  P  L  L  E  F  D  K  G  E  Y  W  T  E  I  A  H  I  P  T  I  Q  I  D  E  E  C  M
3662 AATGATTAAAACAAATGGCTCCCCAACTGATGTAAGCTATTCTTTTCCCTCATAAGCTTTTTATTTCACTTTGCTTTTGGGTTACTTCTCTTTCATTTTAATCATGCCG
3772 GGCTAGCTCATCATCAAACACATAGCATTATATTTAACCTCCATAGAGAATCTAAATTTTTTAAAGATAATTCAATCACAAGTTTAGAAATAACTGCAACTTCCATT
3882 GTCACATGTTATATGATTCTCTATGTTTCTCATGCTTATTGGTTTGATATGCTCTCAATGCCACCATGTTAATCACGTCTCAATGTTTAATCAAAAGTTTTAGTTCT
3992 TGTAATCATCAACCATCCTAGTCACTAGATATACATTTGCAGGGTGTTAATCAACAGTTAAGAGAGTTAGAAATCCCTGTCTTTAGATATCTTCGTCATATACTTTGGCAATTTTAAGCTACA
4102 GATAGGTAAGGCTATAGATATACATTTGCAGGGTGTTAATCAACAGTTAAGAGAGTTAGAAATCCCTGTCTTTAGATATCTTCGTCATATACTTTGGCAATTTTAAGCTACA
4212 GTTTGAACTCATGTGCTGCTGCTATTTTACATCTGTTCCGAGTTTGGTTTTTTTTTTAAATCTTTCCACTAAGCTATTATGTCGTCCACAGTGCTGAATTTCAGGTCTGTTGT
4322 TTTCTAAGGTGCTGCTGCTATTTTTACATCTGTTCCGAGTTTGGTTTTTTTTTTAAATCTTTCCACTAAGCTATTATGTCGTCCAGTGCAAGCCTCTTTTGTAAGTTGACAAACT
4432 TATAGGCAAGTCTTTGAGATGCGACTATCAAAGAAGGGCGATTACAATCAGTGTACCGCTGAAACTATTTCATGTTTCCAGTGCAAGCCTCTTTTGTAAGTTGACAAACT
4542 CGATTAGTTAATATGTTTGGGACTCAACTAGTGTTAGAGTACTCATTTGTAAGACTTGGTACAGAAAATCAAATTAGAATTATCACTCGCGATGGTTGGAATAAC
```

```
   1  AATTCGGCAC  GAGAATTGAA  ATTGGAGGCT  CCAGTTGGTG  AGATGTTTGT
  51  GGAGTATTTG  AGTGTGAATG  ATTGTGGTTG  TGTAGAAGAT  ATATCACCTG
 101  AGTTTCTCCC  AACAGCACGT  AAATTGATTA  TTACGGATTG  CCAGAACGTT
 151  ACTAGGATTT  TGATTCCTAC  TGCCACTGAA  ACTCTCACTA  TTGAGAATTG
 201  TGAGAATGTT  GAAAACTAT   CGGTGGCATG  TGGAGGAGCG  GCCCAGATGA
 251  CGTCTCTGAT  TATTTCGGAG  TGTAAGAAGC  TCAAGTGTCT  TCCAGAACGT
 301  ATGCAGGAAC  TCCTTCCATC  TCTCAAGGAA  CTGCGTCTGT  CTGATTGTCC
 351  AGAAATAGAA  GGAGAATTGC  CCTTCAATTT  ACAAAAACTC  TATATCAGTT
 401  ATTGCAAGAA  ATTGGTGAAT  GGCCGAAAGG  AGTGGCATTT  ACAGAGACTC
 451  ACAGAGTTAT  GGATCCATCA  TGATGGGAGT  GACGAAGATA  TTGAACATTG
 501  GGAGTTGCCT  TCCTCTATTC  AGAGTCTTAC  CATATGCAAT  CTGATAACAT
 551  TAAGCAGCCA  ACATCTCAAA  AGCCTCACCT  CTCTTCAATA  TCTATGTTTT
 601  GATGGTAATT  TATCTCAGAT  TCAGTCACAA  GGCCAGCTTT  CCTCCTTTTC
 651  TCACCTCACT  TCGCTTCAAA  CTCTACAAAT  CCGTAATCTC  CAATCACTTG
 701  CTGCATTAGC  ACTGCCCTCC  TCCCTCTCTC  ACCTGACCAT  CCTCAATTTC
 751  CCTAATCTCC  AATCACTTTC  AGAATCAGCA  CTGCCCTCCT  CCCTCTCTCA
 801  CCTGATCATA  GATGATTGCC  CTAATCTCCA  ATCACTTTCA  GAATCAGCAC
 851  TGCCCTCCTC  CCTCTCTCAC  CTGGACATCT  CCAATTGcCC  TAATCTCCAA
 901  TCACTTTCAG  AATCAGCACT  GCCCTCCTCC  CTCTCTAGCC  TGACCATCTA
 951  TGATTGCCCT  AATCTCCAAT  CACTtCCAGT  AAAAGGGATG  CCGTCTTCCC
1001  TCTCTGAACT  AGCAATTTCC  AAATGTCCAT  TGCTCAAACC  ACTACTAGAA
1051  TTTGGAAAGG  GGGAATACTG  GCCAAATATT  GCTCATATCC  CCTCCATATA
1101  CATCGATTGG  GAACGCATGT  AATGATTAAA  ACGAATGGCT  CCCCAACTGA
1151  TATGTGGATT  TTGAAGAGCG  AGTACGACAA  GTCTGGTACA  TCAATTGTCC
1201  GTAGGAAGTG  TTTCTAAGTG  AATTTTCAGG  TTTGTTGTTA  TAGGCAAGTC
1251  TTTGAGATGC  GACTATCAAA  GAAGGGCGAT  TACGATCAGT  GTACCGCTGA
1301  TATTATTTCA  TGTTTCCAGT  GCAAGCTTCT  TTTGTAAGTT  GACAAACTTG
1351  ATTAGTTCTC  GTGCCGAATT  C
```

FIG. 7

```
   1  CCAGGGTTTT  CCCAGTCACG  ACGTTGTAAA  ACGACGGCCA  GTGAATTGTA
  51  ATACGACTCA  CTATAGGGCG  AATTGGAGCT  CCACCGCGGT  GGCGGcCGCT
 101  CTAGAACTAG  TGGATcCCCC  CGGGCTGCAG  GAATTCTATG  GCAGATTGTC
 151  CTCCAAAAAG  CCTTTTAACT  GTCTTGAGAA  GCTTGAATTT  GAAGATATGA
 201  CGGGGTGGAA  GCAATGGCAC  GCACTAGGAA  TTGGAGAGTT  CCCTACACTT
 251  GAGAACCTTT  CCATTAAAAA  TTGCCCTGAG  CTCAGTTTGA  AGATACCCAT
 301  CCAATTTTCA  AGTTTAAAAA  GGTTACAAGT  TAGAGGTTGT  CCAGTTGTTT
 351  TtGATGATGC  TCAACTGTTT  AGATCCCAAC  TTGAAGCAAT  GAAGCAGATT
 401  GAAGCATTAt  AtATACGTGA  TTGTAACTCT  ATTACCTCCT  TTCCTTTTAG
 451  CATACTGCCA  ACTACCTTGA  AGACAATAGA  GATATCTGGT  TGCCCAAAAT
 501  TGAAATTCGA  GGCGCCAGTT  GGTGAGATGT  TTGTGGAGTa  TTTGAGTGtG
 551  ATTGATTGTG  GTTGTGTAGA  TGATAATATC  ATTAGAGTTT  CTCCCAGCAG
 601  CGTGTAAATT  GAGTATTATG  AGTTGCCACA  ACTTTACTAG  GTTTttGATT
 651  CCTACTGCAA  CTGAAACTCT  CACTATTTCG  AATTGTGAGA  ATGTTGAAAA
 701  ACTATCGGTG  GCATGTGGAG  GAGCGGCCCA  GATGACGTTA  CTGCATaTTT
 751  tGAAGTGTAA  GAAGCTCAAG  TGTCTGCCAG  AACGTATGCA  GGAACTCCTT
 801  CCATCTCTCA  AGGATTTGTA  TCTTTCCAAT  TGTCCAGAAA  TAGAAGGAGA
 851  ATTGCCCTTC  AATTTACATA  AACTCCGTAT  CAGTGATTGC  AAGAAACTGG
 901  TGAATGGCCG  AAAGGAGTGG  CATTTACAGA  GACTCACAGA  GTTAGTGATC
 951  CATCATGATG  GGAGTGACGA  AGATATTGAA  CATTGGGAGT  TGCCTTGTTC
1001  TATTACAGAA  CTTGAGGgTA  TACAATATGA  TAACATTAAG  CAGCCAACAT
1051  CTCAAAAGCC  TCACCTCTCT  TCAATGTCTA  AGTATTGGTG  GTAATTTATC
1101  TCAGATTGGC  CGTCTTTCCT  CCTTTTCTCA  CCTCACTTCG  CTTCAAACTC
1151  TACAAATCAG  GAATTTCGGT  AATCTCCAAT  CACTTGCTGA  ATCAGCACTG
1201  CCATCCTCCC  TCTCTCACCT  GACCATCTCC  CGTTGCCCGA  ATCTCCAATC
1251  ACTTGCTGAA  TCAGCACTGC  CCTCCTCCCT  CTCTCACCTG  AACATCTATG
1301  ATTGCCCGAA  TCTCCAATTA  CTACCTGAAT  CAGCACTGCC  CTCCTCCCTC
1351  TCTCACCTGG  ACATCTCCCA  TTGTCCTAAT  CTCCAATCAC  TACCTGAATC
1401  AGCACTGCTC  TCCTCCCTCT  CTCACCTGGA  CATCTCCCAC  TGTCCTAATC
1451  TCCAATCACT  TGCTGAATCA  GCACTGCCCT  CCTCCCTCTC  TCACCTGACC
1501  ATCTCCCATT  GCCCTAATCT  CCATTCACTT  TCAGAAAAAG  GGATGCCCTC
1551  TTCCCTCTCT  AAACTATCTA  TTTCCAAATG  TTCATTGCTC  ACACCACTAC
1601  TAGAATTTAA  CAAGGGGGAA  TACTGGACAA  ATATTGCTCA  TATCTCCACC
1651  ATACAGATCG  ATTGGAAATG  CATGTAATGA  TTAAAACGAA  TGACTCCCCA
1701  ACTGATATGT  GGATTTAGAA  GAGCGAGTaC  GACAAGTCTG  GTACATCAAT
1751  TGTCCGTAGG  AAGTGTTTCT  AAGTGAATTT  TCAGGTCTGT  TGTTATAGGC
1801  AAGTCTTTGA  GATGTGACTA  TCAAAGAAGG  GCGATTACAA  TCAGTGTACC
1851  GCTGATACTA  TTTCATGTTT  CCAGTGCTAC  AGTGCAAGCC  TCTTTTGTAA
1901  GTTGnCAAAC  TCGATTAGTT  AATATGTTTG  GGACTCAACT  ACTACTCATT
1951  TTGTAAGACT  TAAGTACAGA  AAATCAAATT  AGAATTATAA  CTCGCGATGG
2001  TTGAGTAAAC  TCCAAGAAGC  TCGTGCC
```

```
I2C-1   ............................MEIGLAIGGAFLSSALNVLFDRLAPNGDLLNMFRKH  36
I2C-2   ............................                              V       36
RPM1    ........................MAS TVDFGIGRILSV ENETL   SGVHGE          30
RPS2    ............................                                      0
N-GENE  ..........................MASSSSSSRWSY VFLS     GE              21
L6      MSYLREVATAVALLLPFILLNKFWRPNSKDSIVNDDDDSTSEVDAI DST PSGSFPSVEYEVFLS GP 70
CON.

I2C-1   TDDVELFEKLGDILLSLQI.VLSDAENKKASNQFVSQWLHKLQTAVDAAENLIEQVN..YEALRLKVETS 103
I2C-2       K H K LK  KMT RGI .         Q   PS RD  NE RD  S     E ..         GQ  103
RPM1        I ......  MKKE  IMKS.F E T.H HGG GSTTTTTQLF  F ANTRD AY IEDILDEFGYHIHGY 92
RPS2    ......MDFISSLIVGCAQ.  CESM MAEKRGHKTD.... RQ ITDL TA GDLKAIRDD T RIQ.. 57
N-GENE  DTRKTFTSH YEV NDKG KTFQ DXRLEYGATIPGELCKAIEESQF IVVFS NYATSRWC NEL KIM 91
L6      DTREQFTDF YQS RRYK HTFR DDELLKGKEIGPNL RAIDQSKIYVPIISSGYADSKWC MELA IV 140
CON.

I2C-1   NQQVSDL.NLCLSDDFFLNIKKKLEDTIKKLEVLEKQIGRLGLXEHFIS.........TK..........  153
I2C-2   H NF ETS QQV  E       D      ET KD QE   L      Y D ..........           154
RPM1    RSCAKIWRAFHFPR..YMWARHSLAQKLGMVN MIQS SD.SM RYYH .........ENYQAALLPPID 150
RPS2    QDGLEGRSCSNRAREWLSAVQVTETK ALL VRFRRREQ TRMRRRYL CFGCADYKLC KVSAILKSIG 127
N-GENE  ECK.TRFKQTVIPIFYDVDPSHVRNQKESFAKAF EHETKYKDDVEG QRWRIALNEAANLKGSCDNRDK 160
L6      RR EE PRRII PIFYMVDPSDVRHQ GCYKKAFR HANKF..DGQT QNWKDALKKVGDKGWHIGKND 208
CON.                                                                 I
                                                                    P-LOOP

I2C-1   ......QETRTP.STSLVDDSGIFGRKNEIEN..LVGRLLS.MDTKRKNLAVVPIVGMGGMGKTTLAKAV 213
I2C-2   ......L       .    I EPD   QS    D.. ID   .EGASG   T      L            214
RPM1    DGDAKWVNNISE. SLFFSENSLV IDAPKGK..  I   .PEPQ ...I   AV      SANI      213
RPS2    ELRERSEAIK D.GG IQVTCREIPI SVVG TIMMEQV E.FLSEEEERGIIGVY P   V     MQSI 195
N-GENE  TDADCIRQIVDQI SK CXI LSY.LQ IVGIDTHLEKIE LLEIGINGVRIMG W     V      I R I 229
L6      KQGAIADKVSADIWSHISKENL LETDELVG DDHITAV EKLSLDSE VTM GLY    I      T    278
CON.                                                  α α GMGGαGKTT

I2C-1   YNDERVQKH.FGLTAWFCVSEAYDAFRITKGILQEI.GSTDLKADDNLNQLQVKLKADDNLNQLQVKLKE 281
I2C-2        S KN . D K       N           . I ...............V              278
RPM1    FKSQS RR . ESY  VTI KS VIEDVFRTMIK FYKEA TQIPAE YS ........GYRE VE  V 274
RPS2    N ELITKG QYDVLI VQM REFGECT QQAVGARGLG W E ETGENRA ................IYR 250
N-GENE  FDTLLGR.....MDSSYQFDG CFLXD KE..NKRGNH LQNALLSE LR...EKANYN EEDGKHQMAS 289
L6           KI..........SSC.FDCCCFIDN RETQEKDGVVVLQK LVSEILRIDSGSVGFN DSGGRKTI 337
CON.

II                        III
I2C-1   KLNGKRFLVVLDDVWNDNYPEWDDLRNLFLQGDIGSKIIVTTRKESVALM...MDSGAIYMGILSSEDSW 348
I2C-2     R KE K   I         N  E    V V             D    ... GNEQ  S   N  T A  335
RPM1    Y QS YI        TTGL.. REISIALPD IY  RVMM     DMN  SFPYGIG TKHEIEL KEDEA 342
RPS2    A RQ    LL        EEIDL KTGVPR..PDRENKC VMF    .. I  CNNMGAEYKLRVEF EKKHA 315
N-GENE  R RS KV I    I.DNKDHYLEY AGGLEWFGN  R I   DKHLI....EKNDIIYEVTA PDHE I 354
L6      RVSRFKI   .DEKFKFE M GSPKDFISQ. RF I S SMF LGTLNENQCKLYEV SM KPR L 405
CON.            K+αLαVLDDV               S+αααTTR                L
                                     IV
I2C-1   ALFKRHSL.EHKDPKEHPEFEEVGKQLADKCKGLPLALKALAGMLRSKSEVDEWRNILRSEIWELPSCSN 417
I2C-2    S Q AF. NM MG S L   R    A        T       E   KC         R..D 402
RPM1    V SNKAFPASLEQCRTQNL PIARKLVER O     IAS GS MST KFES  KKVYSTLN   NNNHE 412
RPS2    E CSKVW..R LL SSSIRRLAEI VS G     IT G AMAHRETEE  IHASEVLTRFPAEMKG 384
N-GENE  Q  Q AFGKE...VPNEN KLSLEVVNYA     VWGSL .HNLRLT KSAIE....HMKNN.S 415
L6      E  SK AFKKN...TPPSYY TLANDVV TTA  T VIGSL .F Q IAV EDT E....Q RRTL 467
CON.        LF                       GLPLAL              EW
```

FIG. 8A

```
                        V
I2C-1    ..GILPALMLSYNDLPAH.LKQCFAYCAIYPKDYQFPKEQVIHLWIANGLVHQFHS......GNQYFIEL 478
I2C-2         D              . R  SF  F    P         PVEDEI IQDL    F L     468
RPM1     LKIVRSIMF  F    YP. R  L   SLF VN RMKRKRL RM M QRF EPIRGVKAEEVADS LN 481
RPS2     MNYVFAL  KF   DN ESDL RS  L  LF EEHSIEI LVEY VGE FLTSS GVNTIYK YFLIGD 454
N-GENE   YS  IDK KI    DG EPKQQEMFLDIACFLRGE...E DYILQILESCHIGAEYG..........LRI 471
L6       LDEVYDR KI    DA NPEAKEIFLDIACFFIGQ...N EPYYM TDCNFYPASN............I F 523
CON.            ∝     L  ∝SY  L
                             VI
I2C-1    RSRSLFEMASEPSERDVEE.FLMHDLVNDLAQ................IASSNHCIRLEDNKGSHMLEQC 531
I2C-2        S    RVPN    GNIK L             ..............L    KL     ESQ    522
RPM1     VY NMLQVILWNPFGRPKA.  K   VIWEI .....................................SVS 515
RPS2     KAAC L ......TG EKTQVK  NV RSF .....................LWMASEQ TYKELIL 494
N-GENE   IDK  VFI.......SEYNQVQ    IQ MGKYIVNFQKD PGERSRLWLAKEVEEVMST T TMAM AI 533
L6       IQ  CMIQV.......GDDDE K    QLR MGREIVRREMVLPWKRSRIWSAEEGIDL LNK   SKVKAI 584
CON.                             ∝ MHD∝∝ -

I2C-1    RHMSYSIGQDGEFEKLKSLFKSEQLRTLLPI..DIQFHYSKKLSKRVLHNILPTLRSLRALSLSHYQIEV 599
I2C-2       L  MY  G     TP  Y L      TCSSVNYF .NP T                    KM  E 541
RPM1     KLERFCDVYNDDSD.......GDDAAETMENYGSRHLCIQ EMTPOSIRA..TN H  LVC SAKHKM L 576
RPS2     VEP MGHTEAPKA  NWRQALVISL DNRIQT........... PEKLICPK T  MLQQNS  KK..... 548
N-GENE   MVS   STLRFSNQAV NMKRLRVFNM............GRSSTHYAIDYLPNN  CFVCTNYPW... S 588
L6       SI.PWGVKYEFKS CFLN SELRY HA...........REAMLTGDFN L  N KW ELPFYK GEDDP 643
CON.

I2C-1    LPNDLFIKLKLLRFLDLSETSITKLPDSIFVLYNLETLLLSSCEYLEELPLQMEKLINLRHLDISNTRRL 669
I2C-2            I R N KR     C             K.                       WH      660
RPM1     S..... N  A   EDS   S   CLVTMF  KY N  KTQ.VK   KNFH  V ET NTKHSKIE 640
RPS2     I TGF MHMPV  V    F    EI L  KY VE YH SM GTK.ISV  QELGN RK K  LQR QF 617
N-GENE   F STF..E  M  VH Q  RH............. SLRH WTETKH PS ........ RI L WSK 632
L6       PLTNY..TM N IIVI EHSH ADD......WGGWRHMMKMA R KVVR ASNYSLYG RVRL DCW F 705
CON.

I2C-1    KM..PLHLSRLKSLQVLVGAKFLVGGWRMEYLGEAHNLYGSLSILELENVVDRREAVKAKMREKNHVEQL 737
I2C-2        ..                 V   D  Q         VVK         P              728
RPM1     EL..  GMWK  K ......RY  ITFR  N GHDSNW Y............LGT .. VP IWQ....... 682
RPS2     QTIPRDAICW  SK E  .NLYYSTA  ELQSP  DEAEELGFAD  YLENLTTLGITVLSL.......... 677
N-GENE   T. RTPDFTCMPN EY..VN.. YQCSNL EVHHSLGCCSKVIG Y NDCKSLKRFPCVNVESLEYLGLR 696
L6       P. KSIEVLSMTAIEMDEVD..IGELKKLKT VLKFCPIQKI GGTFGMLKGL  L.........CL FN 762
CON.

I2C-1    SLEWSESISADNSQTERDILDELRPHKNIK.AVEITGYRGTNFPNWVADPLFVK.LVHLYLRNCKDCYSL 805
I2C-2                 Q.E K I              L . K S                           776
RPM1     ........................L .DLQVMDC.......FN EDELI ..............N 702
RPS2     ............E LKTLFEFGAL  H Q.HLHVEECNELLYF LPSLTNHGRN RR SIKS H LEY 733
N-GENE    CDSL KLPEIYGRMKP..........E QIHMQGS I ELP.SSIFQYKTH TX LLWNM....KNLVA 751
L6       WGTNLREVV  IG LSSLKVLKTTGA EVEINEFPL LKELSTSSRIPNLSQLLD EV KVYD  GFDM 832
CON.

I2C-1    PALGQ.....LPCLEFLSIRGMHGIRVVTEEFYG.....................RLS 837
I2C-2         .....    K   VK                  ...................... 828
RPM1     GCMT ..... TRISLVMV  RE  RDLC............................. 725
RPS2     VTPADFENDW  S  V  THSL NLTR........................WG 763
N-GENE   LPSSICRLKS  VS SVSGCSKLESLPEEIGDLDNLRVFDASDTLILRP...................P 801
L6          PASPSEDESSVWWKV...SKLKSLQLEKTRINVNVVDDASSGGHLPRYLLPTSLTYLKIYQCTEPTW P 899
CON.
```

FIG. 8B

```
I2C-1    SKKPFNSLVKLRFEIMPEWKQWHTLG.IGEFPTLEKLSIKNC......PELSLEIPIQFSSLKRLD....  896
I2C-2        C   E    T         A .          I  ......             FRVFGC      891
RPM1     ..DSL KIKRI  LSLTSIDEEEP E. DDL........................................  753
RPS2     NSVSQDC RNI CINISHCNKLKNVSWVQKL K  VIELFD ......R IEEL SEHE P.........  818
N-GENE     IIRL K II M RGFKDGVHFEFPPVAEGLHS  Y NLSY NLID  GG PE .GSL   K  L..S  866
L6        GIENLEN TS EVN IFQTLGGDLD L.QGLRS  I R RKVNGLARIKG KDLLCSSTCK RKFYITEC  968
CON.

I2C-1    .....................ICDCKSVTSFPFSILPTTLKRIKISGCPKLKLEAPVGE..MFVEY  939
I2C-2    PVVF YDAQVLRSQLECMKQIEEIY R   N           T  D          C MS  L E  960
RPM1     .............................................. ATASIE   F AGXLERVPSWFNT  767
RPS2     ...........................VEDPT FPS  TLRTRDL E N........SILPSR  847
N-GENE   RNNFEHLPSSIA    QLGALGSLDLK  QRL QL ..E  PE NELHVDCHMA  FIHYLVTKRKKLHR  930
L6       POLIELLPCELGVQTVVVPSMAELT R  PRL.EVG..PMIRS PKFPM..... KLDLAVANITKE D  1030
CON.

I2C-1    LSVIDCGCV..................DDISPEFLPTARQLSIENCHNVTRFLIPTATESLH.IRNC..  987
I2C-2    F  EE     ................       ERG        .     T   .       EN  1006
RPM1     ..QNLTYL................GLRGSQLQEN .I   QTLPRLVWLSFYN YMGPR.L F...  821
RPS2     VKLD AHNDTMYNLFAYTMFQNISSMRR  ISASDS SLTVFTGQPYPEKIPSWFHHQGWD SVSVN....  996
N-GENE     DA GSLEELV  SLELELDDTSSGIERIVS SKLQKLTTLVV......K PSLREIEGL E KSLQDLYL  1093
L6
CON.

I2C-1    .EKLSMACGGAAQLTSLNIWGCKKLKCLPELLPSLKELRLTYCPE........IEGELPFNLQILDIRYC  1048
I2C-2    V            D  S           Q N  ........             K Y   D   1068
RPM1     ...........QGFQN K LEIVQM H T VV....................  DGAM E  K YV A  860
RPS2     E   WWK LEKDQPNEE C..........Y  RFV N.................................  909
N-GENE   ... PENWYIPDKFLGFAVCYSRS IDTTAH IPVCDDK..........MSRMTQK A....LSECDTE  1048
L6       EGCT LGRLPLEK KE D G  PD TE VQTVVAVPS  GLTIRDCPRLEVGPMIQS  KFPMLNELTLS  1163
CON.

I2C-1    KKLVNGRKEW.HLQRLTELWIKHDGSDEHIEHWELP....SSIQRLFIFNLKTLSSQHLKSLTSLQFLRI  1113
I2C-2                K V Y      D      ....C T EV  I               Y C  1133
RPM1     RG EYVPRGIEN IN Q  HLI .V NQLV RIRGE....G VD ...........SRV HIPAIKHYFR  914
RPS2     ..................................................................  909
N-GENE   SSNYSEWDIHFFFVPFAG  DTSKANGKTPNDYGIIRLSF GEEKMYGLR LYKEGPEVNA LQMRENSN  1118
L6       MVNITKED LEV GS E  DSLELTL DTCSSI RISF L KL K TTLIVEVP LREIEG AE KS  1232
CON.

I2C-1    VGNLSQFQSQGQLSSFSHLTSLQTLQIWNFLNLQSLPESALPSSLSHLIISNCPNLQSLPLKGMPSSLST  1183
I2C-2      D  PI    I            H   S       Q E FH        N          K  1203
RPM1     TD G FYV ...   .....................................................  926
RPS2     ....................................................................  909
N-GENE   EPTEHSTGIRR.TQYNNR   FYE ....ING...................................1144
L6       LYLEGCTSLERLWPDQQQ  G  KN NVLDIQGCK  SVDH SALKTT PPRARITWPDQ YR........1294
CON.

I2C-1    LSISKCPLLTPLLEFDKGEYWTEIAHIPTIQIDEECM  1220
I2C-2       L G          PQ       L   W YI  1240
RPM1     .....................................  926
RPS2     .....................................  909
N-GENE   .....................................  1144
L6       .....................................  1437
CON.
```

```
I2C-1   EEFYGRLSSKKPFNSLVKLRFEDMPEWKQWHTLGIGEFPTLEKLSIKNCPELSLEIPIQF   889
I2C-2            C  E    E     T        A                I            880
I2C-3   ............................................................
I2C-4   Q        C  E    E   TG        A              N       K       60
CON.    EEFYGRLSSKKPFN L KL FEDM WKQWH LGIGEFPTLE LSI NCPELSL IPIQF

I2C-1   SSLKRLD........................ICDCKSVTSFPFSILPTTLKRIKIS       921
I2C-2          FRVFGCPVVFYDAQVLRSQLEGMKQIEEIY R  N            T D      940
I2C-3   ...........................................................N   1
I2C-4          QVRGCPVVFDDAQLFRSQLEAMKQIEALY R  N I          T E        120
CON.    SSLKR                            I DC S TSFPFSILPTTLK I I

I2C-1   GCPKLKLEAPVGE..MFVEYLSVIDCGCVDDISPEFLPTARQLSIENCHNVTRFLIPTAT    979
I2C-2         C MS   L EF   EE   ...         E R G    .              996
I2C-3   SARE         ..      N    E           K I TD Q    I
I2C-4        F       ..            L    A  CK MS   F                  59
CON.       LK EAPV E  MFVE  SV  CGCVDDIS EFLP A  L I   C N TRFLIPTAT   178

I2C-1   ESLHIRNC...EKLSMACGGAAQLTSLNIWGCKKLKCLP....ELLPSLKELRLTYCPET   1032
I2C-2      T    ENV        D S               ....        Q    N       1052
I2C-3    T T E  ENV   V   M  I SE          ERMQ           SD          119
I2C-4    T T S  ENV   V   M LH LK          ERMQ        D Y SN         238
CON.    E L I NC   EKLS ACGGAAQ T L I CKKLKCLP    ELLPSLKEL L CPEI

I2C-1   EGELPFNLQILDIRYCKKLVNGRKEWHLQRLTELWIKHDGSDEHIEHWELPSSIQRLFIF   1092
I2C-2          K Y   D              K V Y      D        C  T EV       1112
I2C-3          K Y   S              H         D           S T C       179
I2C-4         HK R  SD              V H       D        C   N RVY      298
CON.    EGELPFNL  L I  CKKLVNGRKEWHLQRLT L I HDGSDE IEHWELP S   L

I2C-1   NLKTLSSQHLKSLTSLQFLRIVGNLSQFQSQGQLSSFSHLTSLQTLQIWNF.........   1143
I2C-2        I          Y C D    PI   I                    .........  1164
I2C-3        I          Y CFD    I                       R..........  228
I2C-4       MI          C  G     I... R                 R GNLQSLAES   355
CON.    N  TLSSQHLKSLTSLQ L   GNLS   QSQ LSSFSHLTSLQTLQI

I2C-1   .............................................................  1143
I2C-2   .............................................................  1163
I2C-3   ..............NLQSLAALALPSSLSHLTILNFPNLQSLSESALPSSLSHLIIDDC    273
I2C-4   ALPSSLSHLTISRCPNLQSLAESALPSSLSHLNIYDCPNLQLLPESALPSSLSHLDISHC    415
CON.

I2C-1   .....................LNLQSLPESALPSSLSHLIISNCPNLQSLPLKGMPSS    1180
I2C-2   ..................H        S               Q E FH       N      1200
I2C-3   PNLQSLSESALPSSLSHLDISNCP   S                S T YD       V      333
I2C-4   PNLQSLPESALLSSLSHLDISHCP   A                T H  H SE           475
CON.                         NLQSL ESALPSSLS L I CPNL SL GMPSS

I2C-1   LSTLSISKCPLLTPLLEFDKGEYWTEIAHIPTIQIDEECM   1220
I2C-2       K L  G                  PQ      L   W YI   1240
I2C-3       E A       K      G      PN     S Y  W R    373
I2C-4       K    S           N      N      S    WK     515
CON.    LS L IS C LL PLLEF KGEYW  IAHI  I ID
```

TRANSGENIC TOMATO PLANTS CONTAINING A FUSARIUM RESISTANCE GENE

This is a rule 371 application based on the priority date of PCT/US 96/05272 filed Apr. 15, 1996.

FIELD OF THE INVENTION

The present invention relates to genes from the I2 Fusarium resistance locus of tomato belonging to a multi-gene family herein designated I2C, useful either as a tomato resistance gene to plant vascular diseases caused by Fusarium pathogens, or as probes for breeding Fusarium resistant tomatoes or for screening of new diseases in related plants of the Solanaceae family, and to transformed plants, particularly Fusarium resistant tomatoes.

BACKGROUND OF THE INVENTION

Resistance to pathogens is thought to involve a specific recognition between a resistant plant and the pathogen, which triggers a set of responses that act to confine the pathogen. The specificity of this process is considered to involve a recognition between the products of a plant resistance (R) gene and a cognate pathogen avirulence gene (Dangl, 1995; Staskawicz et al., 1995). The characterization of resistance genes is of major importance for elucidating the initiation of the cascade of events that leads to specific resistance responses, as well as for more efficient introduction of resistance to pathogens into important crops.

Several resistance genes have been cloned recently by positional cloning or by transposon tagging. These genes include: the HM1 gene of maize (Johal and Briggs, 1992), the Pto gene of tomato (Martin et al., 1993), the Cf-9 gene of tomato (Jones et al., 1994), the RPS2 (Bent et al., 1994; Mindrinos et al., 1994) and the RPM1 (Grant, 1995) genes from Arabidopsis, the N gene from tobacco (Whitham et al., 1994), and the L6 gene from flax (Ellis et al., 1995; Lawrence et al, 1995). These resistance genes show diverse biological characteristics. The HM1 gene is the only example to date where the gene product acts directly to inactivate a component of the pathogen attack, or a compatibility factor (Briggs and Johal, 1994). The other genes belong to a different genetic category, that of incompatibility (or gene for gene) interaction, based on the recognition by the resistance gene product of in avirulence (or incompatibility) component of the pathogen, which does not necessarily participate in the compatibility or in the infection processes (Briggs and Johal, 1994). These genes are all involved in resistance processes characterized by hypersensitive response (HR). In spite of their origin from different plant species, and their divergent specificity to viral, fungal or bacterial pathogens, a group of these R genes share several structural features. A nucleotide-binding domain (P-loop) and five additional amino-acid stretches of unknown function are conserved in their N-terminal region. A region of leucine-rich repeats (LRR) is present in their C terminus, though the consensus sequence and the length of the repeats are different among them. LRR were shown to be involved in protein-protein interactions in other proteins (Kobe and Deisenhofer, 1994; Kobe and Deisenhofer, 1995), and may have similar role in resistance genes. The N gene, the L6 gene and the Cf-9 gene were shown to belong to large gene families, partially clustered with the resistance gene. The detailed genomic distribution of these multigene families is yet unknown.

The soil-born fungus *Fusarium oxysporum* is the causative agent of severe will diseases in a large variety of plant species world-wide. It is an imperfect fungus for which no sexual cycle is known. The tomato-specific pathogen *Fusarium oxysporum* f. sp. *lycopersici* (*F.o.l*) causes the disease Fusarium wilt. The fungus penetrates the vascular system of roots from both resistant and susceptible varieties, mainly through wounds. During a compatible interaction, which leads to disease, the fungus proceeds through the vascular system which eventually collapses. This leads to wilt and often to death of the plant. During an incompatible interaction, resulting in resistance, the fungus is confined to the lower part of the roots, and further symptoms do not develop. Several mechanisms, not including HR, were suggested to be involved in this resistance. They include: the production of inhibitory secondary metabolites, and structural barriers such as vascular gelation, callose deposition, and abnormal membrane outgrowths of vascular parenchyma cells, termed tyloses. Most of these processes, thought to be involved in resistance to vascular diseases, are detectabe also in compatible interactions, though to a lesser extent. Therefore the exact sequence of events that leads to resistance is still unknown.

Three races of *F.o.l.* and their cognate R genes have been identified in tomato. The classification of different *F.o.l.* isolates into races does not correlate with their general genetic resemblance, as established by restriction fragment length polymorphism (RFLP) analysis and distribution into vegetative compatibility groups (VCG; Elias et al., 1993). The I locus, introgressed from *L. pimpinellifolium*, confers resistance to *F.o.l* race 1, and is located on the short arm of chromosome 11, between the RFLP markers TG523 and CP58 (Eshed and Ori, unpublished). The I3 locus from chromosome 7 of *L. pennellii* confers resistance to races 1, 2 and 3 of *F.o.l.* (Bournival et al., 1990). This locus appears to be composed of three separate but linked genes (Scott and Jones, 1991). The I2 locus, introgressed from *L. pimpinellifolium*, confers resistance to race 2 of the pathogen. We previously mapped I2 to the long arm of chromosome 11, between the RFLP markers TG105 and TG36, very close to TG105 (Segal et al., 1992; Ori et al., 1994). In previous studies we utilized recombinant inbred (RI) lines for mapping I2 (Ori et al., 1994). However this population turned to be problematic for mapping of this region because of a very high recombination rate, including double recombinations, especially in the region of I2.

SUMMARY OF THE INVENTION

It has now been found in accordance with the present invention that high resolution genetic and physical mapping of the I2 region, using a large and conclusive F2 population (3200 meiotic gametes), show complete cosegregation between I2 and a cluster of genes on chromosome 11 belonging to a new multigene family, herein designated I2C.

Additional multigene family members are dispersed between four different loci, on three different chromosomes, either in clusters or as single genes. Two I2C genomic clones were isolated from the locus completely linked to I2 and sequenced, and were herein designated I2C-1 and I2C-2. Their sequences show striking structural similarity with a group of recently isolated resistance (it) genes, which includes the above-mentioned RPS2 and the RPM1 genes from Arabidopsis, the N gene from tobacco and the L6 gene from flax. These genes confer resistances to specific pathogens of viral, bacterial and fungal origin, and share common features. They contain a conserved nucleotide binding domain, termed P-loop, in their N terminus, and five other conserved domains of unknown function. At least half of their C terminus is composed of leucine rich repeats (LRR).

A few partial cDNA clones from the I2C family were further examined, such as the herein designated I2C-3 and I2C-4 cDNA clones, and show that family members differ from each other mainly by insertions or deletions.

The deduced amino acid sequence encoded by members of this gene family reveals a region of LRRs, as well as a P-loop and other motifs in common with the above-mentioned recently characterized plant resistance genes.

Thus, in one aspect, the present invention provides a DNA molecule selected from the group comprising:

(i) a DNA molecule having a nucleotide sequence derived from the coding region of the clone herein designated I2C-1 (SEQ. ID. NO.:1);

(ii) a DNA molecule having a nucleotide sequence derived from the coding region of the clone herein designated I2C-2 (SEQ. ID. NO.:3);

(iii) a DNA molecule having a nucleotide sequence derived from the codinz region of the clone herein designated I2C-3 (SEQ. ID. NO.:5);

(iv) a DNA molecule having a nucleotide sequence derived from the coding region of the clone herein designated I2C-4 (SEQ. ID. NO.:6);

(v) a DNA molecule characterized by containing a coding sequence representing at least 60% similarity with the encoded open reading frame in the DNA sequence of at least one of the DNA molecules (i) and (ii);

(vi) a DNA molecule capable of hybridization with any one of the DNA. molecules (i)–(v) under moderately stringent conditions;

(vii) a DNA molecule that differs, by insertion, deletion or as a result of the degenerative nature of the genetic code, from the DNA sequences (i)–(vi); and (viii) a fragment of any of the DNA molecules (i)–(vii).

The DNA molecule defined in (v) above contains preferably a coding sequence representing 70–80% similarity with the encoded open reading frame in the DNA sequence of at least one of the DNA molecules (i) and (ii). The moderately stringent conditions required in (vi) above are such as those conditions described in Sambrook et al., Molecular Cloning: A Laboratory Manual, 2nd. edition, Cold Spring Harbor Laboratory Press, New York, 1989.

One of the members of the multigene family I2C consisting of a DNA molecule as defined in (i)–(vii) above will confer resistance to *Fusarium oxysporum* f.sp *lycopersici* race 2 in tomato plants. In another aspect, the invention relates to a gene construct comprising such DNA as a genomic clone including regulatory sequences that flank the coding region thereof, and to a cosmid, into which said gene construct has been subcloned, for direct transformation of tomato plants.

In another embodiment, a DNA molecule according to the invention may be subcloned into a plant transformation vector under the control of regulatory elements capable of enabling the expression of said DNA molecule in plant cells. Said DNA regulatory sequences comprise, for example, a plant promoter, a DNA sequence that enhances translation of the mRNA transcribed from said DNA molecule and a polyadenylation/terminator sequence.

In a further embodiment the invention provides a tomato cell line or a tomato plant line transformed with a cosmid or with an expression vector of the invention, and to tomato plants regenerated from said transformed cells In another aspect of the invention, a DNA molecule or fragment thereof as defined in (i)–(viii) above may be used as a direct RFLP probe employing standard protocols for breeding tomatoes resistant to *Fusarium oxysporum* f.sp *lycopersici* race 2, or to examine the homologous multigene family in related plants of the Solanaceae family, e.g. potato, pepper, petunia, eggplant, preferably plants which have colinear genomic maps with tomatoes, for finding new species-specific disease linkages with said probes. The thus bred tomato plants and related plants of the Solanaceae family are also encompassed by the present invention.

Thus the invention provides a method of selective breeding of Fusarium resistant tomatoes employing a DNA molecule according to the invention as a direct restriction fragment length polymorphism (RFLP) probe, which comprises:

(i) marking said DNA molecule with a suitable marker; and (ii) reacting said probe of (i) with DNA extract of a tomato plant under hybridization conditions;

thus obtaining restriction-length polymorphism that is indicative of a resistance-type gene, which facilitates the selection of progeny that contains said resistance gene.

The invention further provides a method of screening new diseases in plants of the Solanaceae family employing a DNA molecule according to the invention as a direct RFLP probe which comprises:

(i) marking said DNA molecule with a suitable marker, and (ii) reacting said probe of (i) with DNA extracts from said Solanaceae species, thus identifying the homologous gene family in those species which can be linked to known resistance genes in those species.

DESCRIPTION OF THE DRAWINGS

FIG. 4 depicts the nucleotide sequence and deduced amino acid sequence of the clone herein designated I2C-1 [SEQ. ID. NOS:1 and 2, respectively]. The first translated nucleotide is no. 1. Sequences conserved between resistance genes are double underlined. Leucine Rich Repeats (LRRs) region and other AA repeats are single underlined. A putative Leucine-Zipper domain is underlined with dots.

Figure 5A:
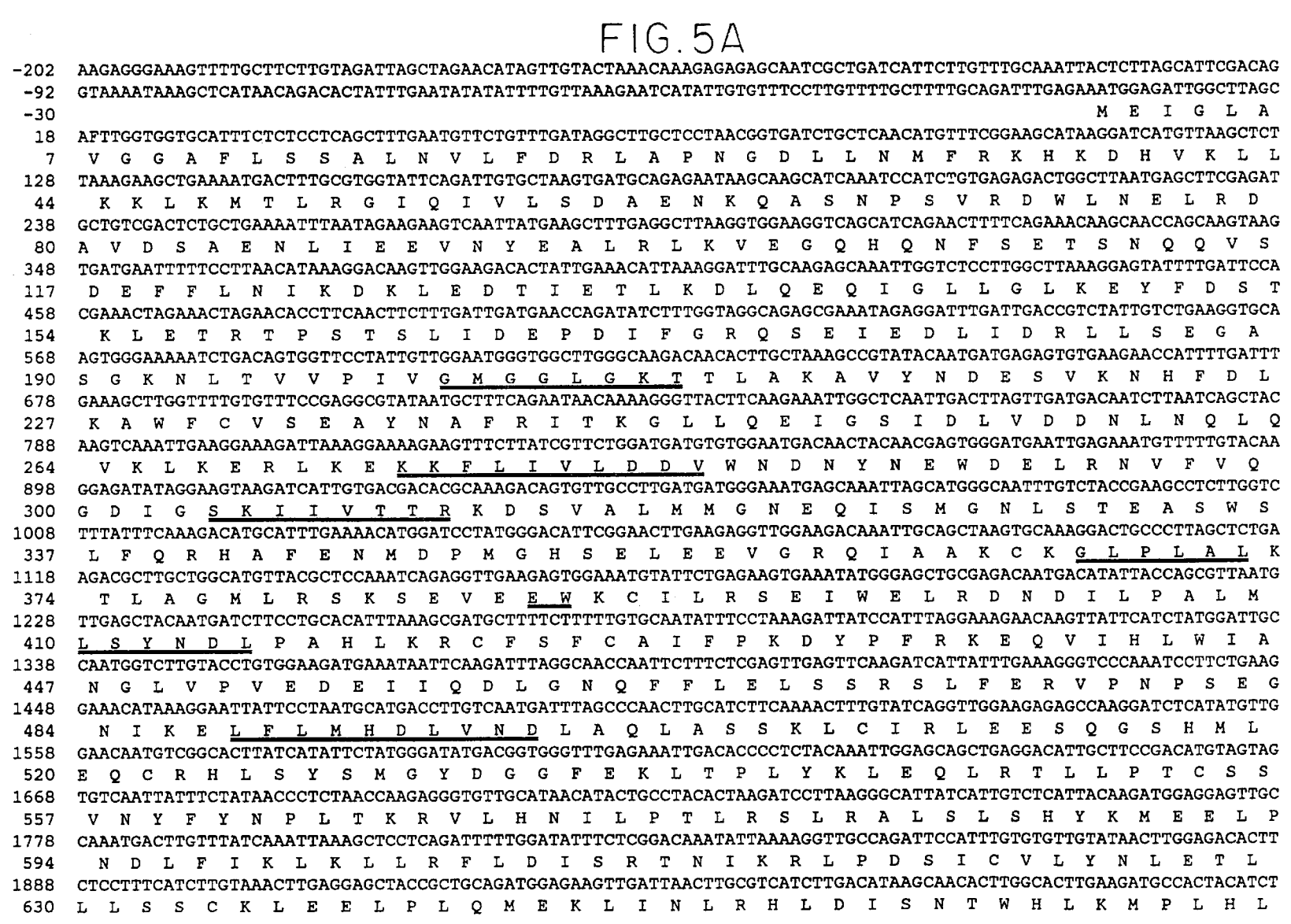
Figure 5B:
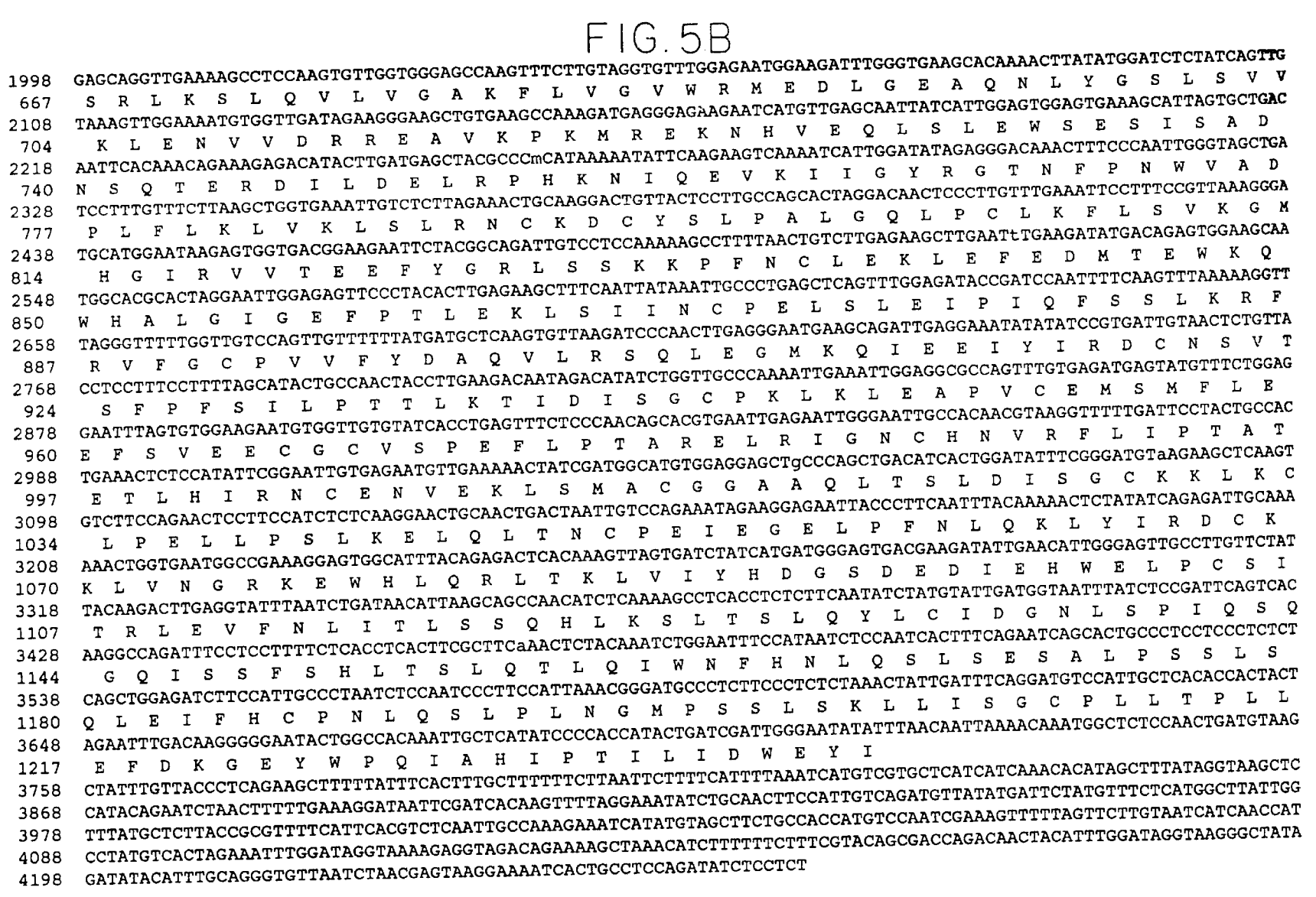

FIG. 5 depicts the nucleotide sequence and deduced amino acid sequence of the clone herein designated I2C-2 [SEQ. ID. NOS:3 and 4, respectively]. The first translated. nucleotide is no. 1. Sequences conserved between resistance genes are double underlined.

FIG. 6 depicts the partial nucleotide sequence of the 3' of the cDNA clone herein designated I2C-3. [SEQ. ID. NO:5]

FIG. 7 depicts the partial nucleotide sequence of the 3' of the cDNA clone herein designated I2C-4. [SEQ. ID. NO:6]

FIG. 8 shows comparison of the deduced amino acid sequences of the genomic clones I2C-1, I2C-2 [SEQ. ID. NOS:3 and 4] and of the resistance genes RPS2 and RPM1 (SEQ ID. NO:8) from Arabidopsis, N (SEQ ID. NO:9) from tobacco and L6 (SEQ ID. NO:10) from flax (Bent et al., 1994; Dangl, 1995; Grant, 1995; Jones et al., 1994; Mindrinos et al., 1994; Lawrence et al., 1995; Whitham et al., 1994). Residues numbers are from the first translated methionine of each sequence. Consensus sequence in the N terminal region is indicated only when minimum number of gaps was needed for alignment of at least 5 out of 6 residues. Symbols are: con., consensus sequence; a, aliphatic residue; – and +, negatively or positively charged residues, respectively. Boxes containing stretches of conserved residues are indicated by a line above the sequences, and numbered from I to VI.

FIG. 9 shows alignment of the leucine reach repeats (LRR) of I2C-1 [SEQ. ID. NO:2], and their consensus sequence.(Top) Alignment in the region from residues 558 to 220 of I2C-1 where alignment to consensus sequence is optimized; (Bottom) A comparison of the consensus sequences of the I2C-1 LRR with those of the resistance genes RPS2, N and Cf-9, and the T-LR SAG expression site associated leucine rich protein from *Trypanosoma brucei*.α represents an aliphatic residue.

FIG. 10 shows comparison of the 3' end of four I2C family members. I2C-1 and I2C-2 are the deduced amino acid sequences [SEQ. ID. NOS:2 and 4] as in FIG. 8. I2C-3 and I2C-4 are the deduced amino acid sequences [SEQ. ID. NOS:11 and 12] derived from partial cDNA clones from a λgt 10 library. The sequence of I2C-4 is a chimera between three ORFs. originally separated by one base insertions which caused two frame shifts. The junctions where separated ORFs were combined are indicated by arrows. Con. indicates consensus and is shown when a residue is present in all 4 sequences. Numbers are from the first methionine in sequences I2C-1 and I2C-2 [SEQ. ID. NOS:2 and 4] and from the first residue of the available sequence for I2C-3 and I2C-4 [SEQ. ID. NOS:11 and 12]. Brackets indicate a repeat unit of 23 amino acids which appears in variable copy number in the 3' end of the cDNA clones.

DETAILED DESCRIPTION OF THE INVENTION

Figure 1A:
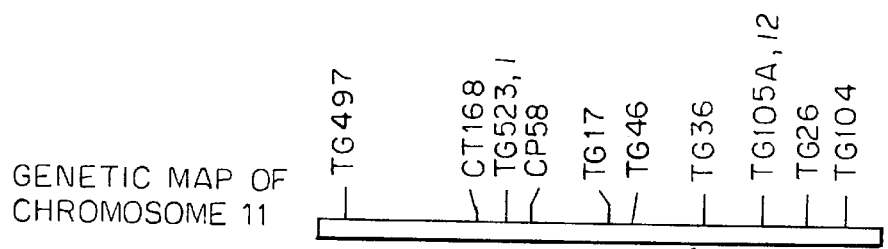
FIGS. 1A–C depict genetic and physical maps of the tomato gene I2 region. (1A) Genetic linkage map of chromosome 11, adopted from Eshed et al. (1995). The I and I2 Fusarium resistance loci were positioned according to Eshed (unpublished) and Segal et al. (1992), respectively; (1B) High resolution mapping of the genetic region spanning RFLP markers TG105A and TG36, as revealed from analysis of 1600 F2 and F3 individuals; (1C) Physical map of YAC 340-63, with relevant markers indicated. The total length of YAC 340-63 is 350 kb.

The invention relates to a multigene family, I2C, which is dispersed on three different chromosomes of the tomato genome. Two lines of evidence suggest that a member of this gene family is the I2 Fusarium resistance gene. The first is the complete cosegregation of some of the genes from this family with the I2 gene; the second is the striking structural similarity between members of this family and a group of recently isolated plant resistance genes (Bent et al., 1994; Dangl, 1995; Grant et al., 1995; Jones et al., 1994; Mindrinos et al., 1994; Lawrence et al., 1995; Whitham et al., 1994). In addition, I2C genes from the SL8D locus of the family, which maps to I2, were shown here to be very highly polymorphic between *F.o.l.* resistant and susceptible varieties. In a similar fashion, the Pto resistance gene was also shown to be a gene family highly polymorphic between bacterial speck resistant and sensitive varieties (Martin et al., 1993). Which of the family members are responsible for resistance can be determined by extensive complementation tests with all members of the SL8D cluster.

The I2C gene family contains a few motif, that have been identified in plant resistance genes. The N terminus contains a P-loop and 5 additional conserved boxes of unknown function. Different classes of P-loop motifs are common to many but not all nucleotide binding proteins (Saraste et al., 1990) The consensus of this motif varies significantly between different classes of nucleotide binding proteins, but is highly conserved within each class. The consensus sequence GMGGaGKTT, where a designates an aliphatic amino acid, is highly conserved among the P-loops of the genes I2C-1, 12C-2, RPS2, RPM1, N and L6. No other protein in the gene bank were found to contain this consensus sequence. In contrast to the Cf-9 gene, and perhaps the RPS2 gene, the I2C-1 deduced protein sequence does not predict any membrane-spanning domain. Residues 623 to 645 of I2C-1, included in the LRR region, fit the consensus for a leucine zipper (Busch and Sassone-Corsi, 1990) This motif is considered to be involved in dimerization of DNA binding proteins. However, sequences that fit this consensus are abundant in the databanks, and the existence of this consensus does not necessarily imply a function.

In common with recently isolated plant resistance genes, the C-terminal parts of the I2C genes are composed of leucine rich repeats. The LRR consensus comprising 23 amino acids, together with a lack of a membrane spanning domain in the gene, are consistent with an intracellular location of this gene family (Jones et al., 1994). The LRRs of four members of the I2C family show high homology to each other and differ from each other mainly by insertions or deletions. This may be indicative of evolutionary processes, and hint at mechanisms that generate new diversity of LRR. Interestingly, one of the cDNA analyzed, I2C-4, contains stop codons within the LRR region, and therefore may result in a truncated protein. This is reminiscent of phenomena described for the N and the L6 genes, where truncated transcripts were described, apparently arising from alternative splicing. In the case of I2C-4 this mechanism is less likely, since the genes analysed thus far from the family appear to lack introns. The I2C LRR-region consensus is homologous to the trypanosome variable surface glycoprotein (VSG) expression site associated gene T-LR. This gene is thought to be involved in the regulation of adenylate cyclase function (Ross et al., 1991; Smiley et al., 1990). LRR were described recently in many proteins, and may be involved in protein-protein interactions (Colicelli et al., 1990; Kobe and Deisenhofer, 1994). Thus, the LRR region may be responsible for specificity of interaction, either with a protein component from the pathogen, or with downstream factors involved in signal transduction. The crystal structure of an interaction of an LRR containing protein, an RNAase inhibitor (RI), with RNAase, was recently described (Kobe and Deisenhofer, 1995). The RI contains a horse-shoe like structure in which individual, 28–29 residues long repeats constitute b-a hairpin units which are aligned parallel to a common axis (Kobe and Deisenhofer, 1993). However, the LRR consensus of I2C and of the other plant resistance genes differ from that of RI. In addition, the repeat length of I2C varies between 19 and 32 amino acids per repeat. Similar variation in repeat length can be observed in other R genes, which may imply a less organized or different structure than that found for RI.

Using novel tomato genetic populations (Eshed et al., 1992; Eshed and Zamir, 1994; Eshed and Zamir, 1995), all members of the I2C family have been mapped according to the present invention. The I2C genes are distributed to five locations in the genome, two of which are clusters of several genes, both on chromosome 11. Some of the recently isolated resistance genes were also shown to be members of large, clustered, gene families, but complete mapping data for them is lacking. The complex pattern of distribution of I2C is remindfull of the case of L and the M rust resistance genes of flax (Ellis et al., 1995). In that case, L appears to be a single multiallelic gene, whereas homologous sequences map to a more complex M locus containing a gene cluster. Both loci may contain resistance genes specific for different races of the same pathogen, or to different pathogens. It is interesting to note in this respect, that the I2C copy from chromosome 9 (SL8B) maps with a resolution of 5 cM to both the Tm-2a TMV resistance gene (Young, et al., 1988), and the Frl *Fusarium oxysporum* f.sp. *radicis lycopersici* (*F.o.r.l.*; Laterrot and Moretti, 1995). The I2C cluster SL8C maps in the vicinity of the Sm Stemphylium resistance gene, with a resolution of 10 cM (Behare et al., 1991). However, no member of the I2C family maps to the I locus on the short arm of chromosome 11, or the I3 locus in chromosome 7 (Bournival et al., 1990; Scott and Jones, 1991), which confers resistance to races 1, 2 and 3 of *F.o.l.*

Considering that a member of the I2C family encodes for the I2 resistance gene, the present invention shows commonalties between a wilt disease resistance gene and other disease resistance genes. Despite the lack of HR in vascular disease resistance, the I2C family belongs to the superclass of resistance genes described for leaf HR This raises questions concerning the role of the various functional domains of R genes in upstream and downstream events that result in different types of resistance mechanisms.

For transformation of tomato plants, a genomic I2C clone according to the lo invention may be subcloned into any suitable cosmnid, such as cosmid TDNA 04541 (Jones et al., 1992). Such constructs contain more than a few kb of genomic DNA upstream and downstream from the gene coding, region sufficient for regulated expression. These constructs can be used for direct DNA transfer into plant cells by electroporation (Dekeyser et al., 1990); by polyethyleneglycol (PEG) precipitation (Hayashimoto et al., 1990), by balistic bombardment (Gordon-Kahn et al., 1990), or by Agrobacterium-mediated transformation (Jones et al., 1992).

Other engineered constructs according to the invention comprise a DNA molecule of the invention and DNA regulatory elements enabling the expression of said DNA, molecule in plant cells. Said DNA regulatory sequences comprise, for example, a plant promoter, a DNA sequence that enhances translation of the mRNA transcribed from said DNA molecule and a polyadenylation/terminator sequence.

The plant promoter used in the invention is selected from tissue specific and non-tissue specific plant promoters of different kinds, derived from both mono- and dicotyledoneous plants. The preferred promoter is the commercially available cauliflower mosaic virus (CaMV) 35S promoter that is generally expressed in most, if not all, plant tissues, including vascular tissues. Another example of promoter expressed in vascular tissues that can be used in the invention is PRB-1) (Eyal et al., 1993).

The promoter is to be found in the 5' region of the gene. At the 3' end of the promoter, a short DNA sequence for 5' mRNA non-translated sequence may be added to enhance translation of the mRNA transcribed from the gene such as the omega sequence derived from the coat protein gene of the tobacco mosaic virus (Gallie et al., 1987).

Downstream at the 3' end of the resistance gene DNA coding sequence a terminator DNA sequence containing the 3' transcription termination and polyadenylation signal of the mRNA from the resistance gene is installed. Terminator DNA sequences comprised within the 3' flanking DNA sequences of any cloned genes can be used, such as the 3' untranslated sequence of the octopine synthase gene of the Ti plasmid of *Agrobacterium tumefaciens* (Greve et al, 1983), or more preferably the 3' untranslated sequence of the nopaline synthase gene (Depicker et al., 1982).

The gene constructs of the invention can be subcloned into expression vectors, such as the Ti plasmids of *Agrobacterium tumefaciens*, the preferred plasmid being the pGA492 binary vector (An., 1986).

The expression vector comprising the resistance gene is then introduced into plant cells by a transformation protocol capable of transferring DNA to dicotyledoneous plant cells, preferably by infection of plant cells with *Agrobacterium tumefaciens* using the leaf-disk protocol (Horsch et al., 1985). For this purpose, tomato leaf explants are infected and the transformed tomato cells are cultured on a suitable medium, preferably a selectable growth medium. Tomato plants can then be regenerated from the resulting callus. Tissue cultures of transformed tomato cells are propagated to regenerate differentiated transformed whole plants. Transgenic plants are thereby obtained whose cells incorporate a Fusarium resistance gene in their genome, said gene being expressible in the cells. Seeds from the regenerated transgenic plants can be collected for future use. Transformed plants that are resistant to *Fusarium oxysporum* f.sp. lycopersici race 2 can be selected by incorporating a selectable marker such as resistance to kanamycin.

Figure 2:
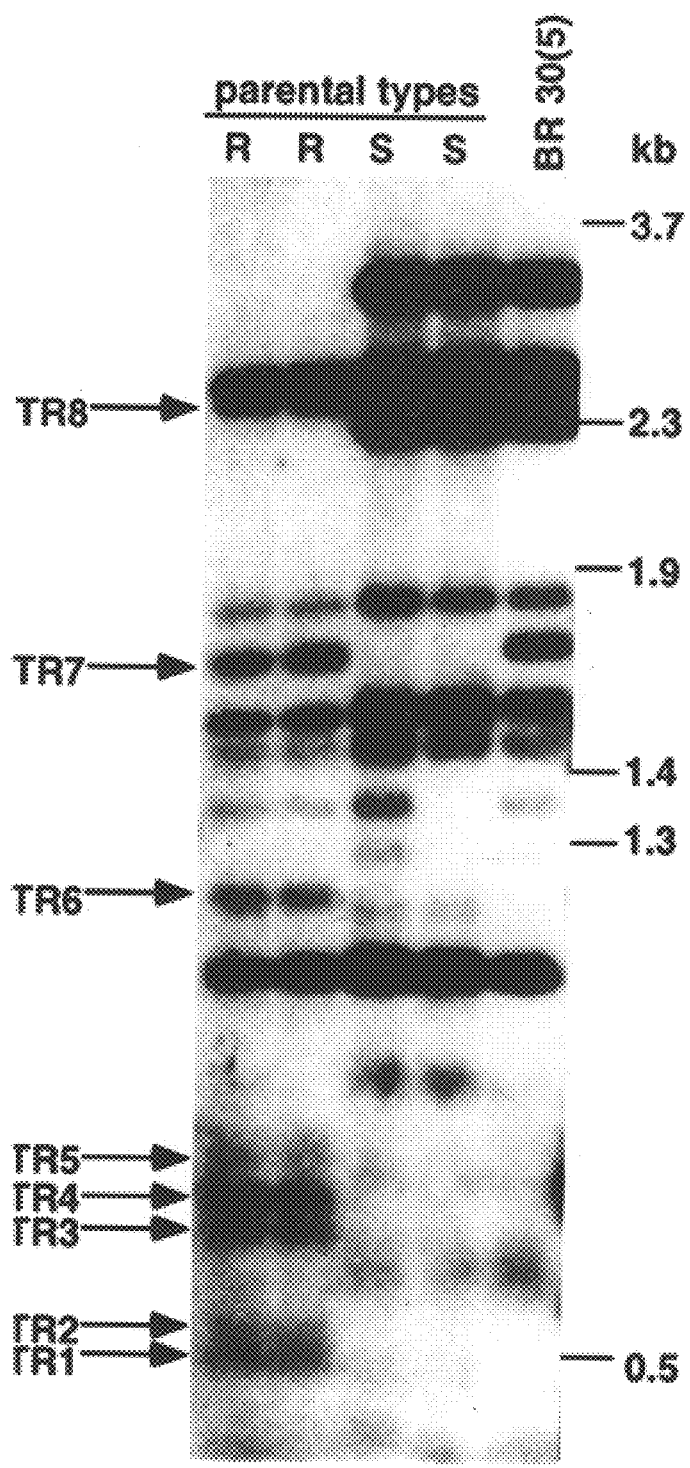
FIG. 2 shows Southern blot analysis of genomic tomato DNA of resistant and susceptible parental types and of the fixed recombinant F2 plant BR 30(5). DNA samples were digested with TaqI, and the blot hybridized with SL8 probe R and S indicate *F.o.1* race 2 resistant and susceptible individuals, respectively. R lanes, parental types which are a nonrecombinant resistant type F2 individual from the F2 population initiated from Br5577; S lanes, parental lines which are the sensitive tomato inbreds *L. esculentum* var. M82 and *L. esculentum* var. S-365. BR 30(5) is the single recombinant identified within the SL8 cluster, from the entire F2 population. TR1-TR8 indicate resistant-type polymorphic bands, as established by examination of this and additional gels. Sizes in kb are indicated on the right.

The DNA molecules of the invention can further be used as markers in selective plant breeding as direct RFLP probe as exemplified in Examples 2 and 3 and FIGS. 2 and 3 herein, or small fragments thereof can be used for PCR-based technology in marker assisted breeding (review by Tanksley et al., 1995).

In the RFLP probe technology, the DNA from different varieties of tomatoes or related Solanaceae plants is digested by restriction enzymes and fractionated on an agarose gel. Digests are chosen such that the gene of interest will be polymorphic. The DNA fragments are transferred to a nitrocellulose or other similar blotting agent and hybridized to the I2C probe of the invention, preferably under conditions of 6×SSC, 0.5% SDS, at 65° C. The blots are washed, preferably at 2×SSC at room temperature, and subjected to autoradiography. Further washings at higher temperatures and lower SSC concentrations can be carried out for higher stringency.

The individual DNAs in the population that show the polymorphic signature of the resistance gene can then be further used in a breeding program for the desired traits.

An advantage of using these DNA sequences as direct RFLP probes in selective plant breeding is that the presence of disease resistance in plants can then be examined without using phytopathological methods. In addition, by using a direct or tightly-linked DNA marker as probe (based on RFLP or PCR-based technologies), it is possible to select for the desirable trait, i.e. resistance gene without accompanying genetic drag, i.e. transfer of the desired trait by breeding without incorporation of flanking unwanted traits.

The DNA molecules of the invention can further be used as probes to identify homologous multigene families conferring resistance to different diseases in related, plants of the Solanaceae family, such as those which have colinear genomic maps with tomatoes, e.g. potato, eggplant, pepper, petunia and the like, for example, by using a marker of the I2C-1 family as a DNA probe to clone the related gene family from said related Solanaceae species, and then using that clone or I2C members directly as DNA probes to analyze genetic lines of those species for RFLP linkage to resistances in said species.

In the PCR-technology, a preferred approach uses specific oligonucleotides synthesized according to the sequences of selected regions of the I2C family such that the fragment generated in a PCR reaction will yield a polymorphic band for the resistance trait either by being specific for the resistance-type gene and therefore yielding a null PCR reaction in sensitive plants, or by yielding PCR fragments of different size or different restriction patterns upon using sensitive or resistant sources of the DNA.

The invention now will be illustrated according to the following non-limiting Examples and the drawings herein.

EXAMPLES

In the Examples, the following Materials and Methods are used.

MATERIALS AND METHODS (a) Plant Material and Magnetic Mapping

Four *L. esculentum* segregating F2 population were used for genetic mapping. In each case, an initial cross was made between a parent resistant to *F.o.l* race 2 (R), and a susceptible parent (S). The resistant and susceptible parents for the first 3 populations were, respectively, c.v. Motelle and c.v. Money Maker; c.v. Mogeor and c.v. Vendor, and c.v. Motelle and LA1113 (chromosome 11 marker stock, kindly provided by Dr. C.M. Rick (UC Davis). The fourth population was initiated from the commercial hybrid line Br5577 (AB Seeds, Ness Ziona, Israel), as F1. The results obtained from the 4 populations were pooled.

(b) Genomic and cDNA Libraries Plasmids and Probes.

YAC8 (YAC 340-63, Cornell collection), which contains the RFLP marker TG105A, was generated from the *F.o.l* race 2 resistant tomato line Rio Grande—PtoR, and cloned in the vector pYAC 4 (Martin et al., 1992). Probes from YAC 340-63 that were used for the genetic and physical mapping are as follows. D2 is from a genomic lambda library of the tomato line VFNT cherry, selected during chromosome walking from TG105. SL8, SR8 and 6-16, are subclones of IEMBL3 clones from a library of the yeast line that contains YAC 340-63. D14 is a cDNA clone selected by YAC 340-63 from a cDNA library from roots of the *F.o.l*. race 2-resistant tomato *L. eesculentum* c.v. Mogeor. Additional clones, previously described (Ori et al, 1994), were not polymorphic. or not informative in these populations.

cDNA clones which represent members of the I2C family were isolated from three different cDNA libraries. The cDNA libraries were all constructed in λgt10, from roots or leaves of resistant-type *L. esculentum*, Positive clones were equally abundant in the three different libraries. While large (>3 kb sizes) clones have been previously isolated from these libraries, all the SL8 clones were partial and contained only the 3' end of the genes. Cosmid clones were isolated from a genomic library of the *F.o.l*. race 2 resistant variety *L. esculentum*. var. Mogeor. constructed in the cosmid TDNA 04541 (Jones et al., 1992).

(c) Sequence Analysis

Cosmid clones were either subcloned into the Bluescript plasmid or sequenced directly. The cDNA clones were subcloned into the Bluescript vector and then sequenced. Sequencing was performed with an automated Applied Biosystems Sequencer. Sequence analysis was performed using the sequence analysis software package of the 'University Wisconsin, Genetics Computer Group' (Devereux et al, 1984).

(d) Physical Mapping

Yeast DNA for pulse field gel electrophoresis analysis was digested with limiting amounts of the restriction enzymes MluI, XhoI and SalI, to obtain successive partial digestions. The digests were fractionated on counter clamped homogeneous electric field (CHEF) gels (BioRad), blotted and hybridized with probes. The maximal distance between a pair of markers was estimated according to the smallest partial band that contained both markers. Additionally, the DNA was digested with the rare cutters SgrAI and PmeI.

(e) Genetic Mapping

RFLP analysis and *F.o.l*. inoculation were performed as previously described (Segal et al., 1992). F2 plants (1200) were screened for recombinants between TG105 and TG36. When necessary, F3 seedlings from the recombinant plants were screened in order to fix the recombination to a homozygous state. An additional 400 F3 plants were screened, and more recombinants were identified in the region. All the recombinants were analyzed for the different RFLP markers and for Fusarium resistance.

Example 1

High Resolution Mapping of I2

Figure 1B:
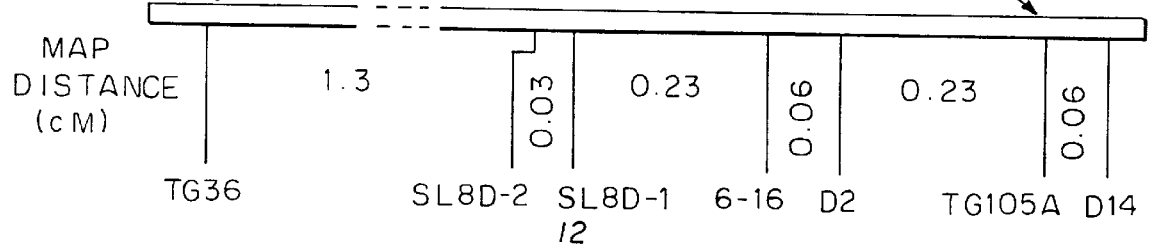
Figure 1C:
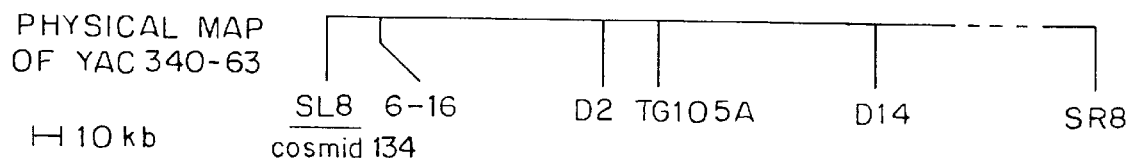

The I2 Fusarium resistance gene was previously mapped to chromosome 11 between RFLP markers TG105A and TG36, 0.4 centimorgan from TG105A (FIG. 1A, and Segal et al., 1992). To obtain higher resolution mapping of 12, we generated new markers in the region of TG105A, by chromosome walking from TG105A on lambda clones, and by subcloning a 350 kb YAC clone, YAC 340-63, that hybridized to TG105A. Pulse Field Gel Electrophoresis (PFGE) of YAC 340-63 was used to physically position genetically informative markers, as shown in FIG. 1C. In order to localize the position of I2 relative to the new markers, a segregating population of 1600 plants (F2 and F3) was screened for recombinations between TG105A and TG36, and 57 recombination events were detected. The recombinant plants were then tested for *F.o.l* race 2 resistance, and for RFLP markers located between TG105A and TG36. According to the resulting map (FIG. 1B), I2 maps to the multi-copy marker SL8D, which represents the edge of YAC 340-63 (FIG. 1C) and lies genetically between markers 6-16 and TG36, 0.23 cM from 6-16 and 1.3 cM from TG36. In previous studies we utilized recombinant inbred (RI) lines for mapping of I2 (Ori et al, 1994). Interestingly, in spite of some inconsistencies in linearity of markers between the RI and the F2 population described here, SL8D completely congregated with I2 also when mapped using the RI it) lines (data not shown). The SL8 marker showed a remarkably high rate of polymorphism between F.o.l race 2 resistant and susceptible lines. In comparison, flanking markers showed a much lower degree of polymorphism, as judged by the paucity of restriction digests that yielded polymorphic bands.

Example 2

SL8 is a Member of a Gene Family Cosegregating with I2

The complete genetic cosegregation of SL8D with the I2 resistance gene and the unique level of polymorphism between resistant and susceptible lines prompted us to further characterize the multicopy marker SL8. Sequence analysis revealed that SL8 contains an open reading frame with similarity to a group of recently isolated resistance genes (see below). This suggested that SL8 is a part of a gene that belongs to a family which includes the I2 resistance gene. The gene of which the SL8 probe was the 3' part was therefore designated I2C-1 (I2 candidate 1).

We wished to further characterize the different SL8 family members as RFLP markers, draw criteria to distinguish between them, and analyze their genomic distribution. A comparison of the SL8 RFLP patterns of resistant and susceptible type lines, obtained with the restriction enzyme TaqI, is shown in FIG. 2. Approximately 17 different TaqI bands hybridized to the SL8 probe, and many of them were polymorphic between resistant and sensitive lines. Resistant-type bands, consistent among all tested lines, were designated TR1-TR8. The rest of the bands were either nonpolymorphic or polymorphic between the susceptible lines, because of the different parental origins. As several polymorphic TaqI bands were detected with the SL8 probe, direct allelism cannot be established. In the entire F2 population, a single recombinant plant was identified between all the polymorphic SL8-bands (BR 30(5) in FIG. 2), which separated SL8D two distinct loci, SL8D-1 and SL8D-2. (FIG. 1B). Except for this case, all into polymorphic SL8 bands congregated. The recombinant individual BR30 (5) is sensitive to F.o.l race 2, and contains one resistant-type TaqI band, TR7, but lacks the others (TR1-6 and TR8). Similar additional southern blots and progeny tests of BR 30(5) confirmed these results (data not shown). Therefore, bands TR1-TR6 and TR8 appear to completely cosegregate witheach other and with I2, and are all candidates for the resistance gene. However, the possibility of a recombination within the gene should also be considered. This could result in a sensitive plant containing a part of the resistance gene, and consequently a polymorphic band that belongs to the resistance gene. In addition, the possibility exists that a nonpolymorphic band represents the resistance gene. The latter is unlikely as will be shown below.

Example 3

Genomic Distribution of I2C

Figure 3A:
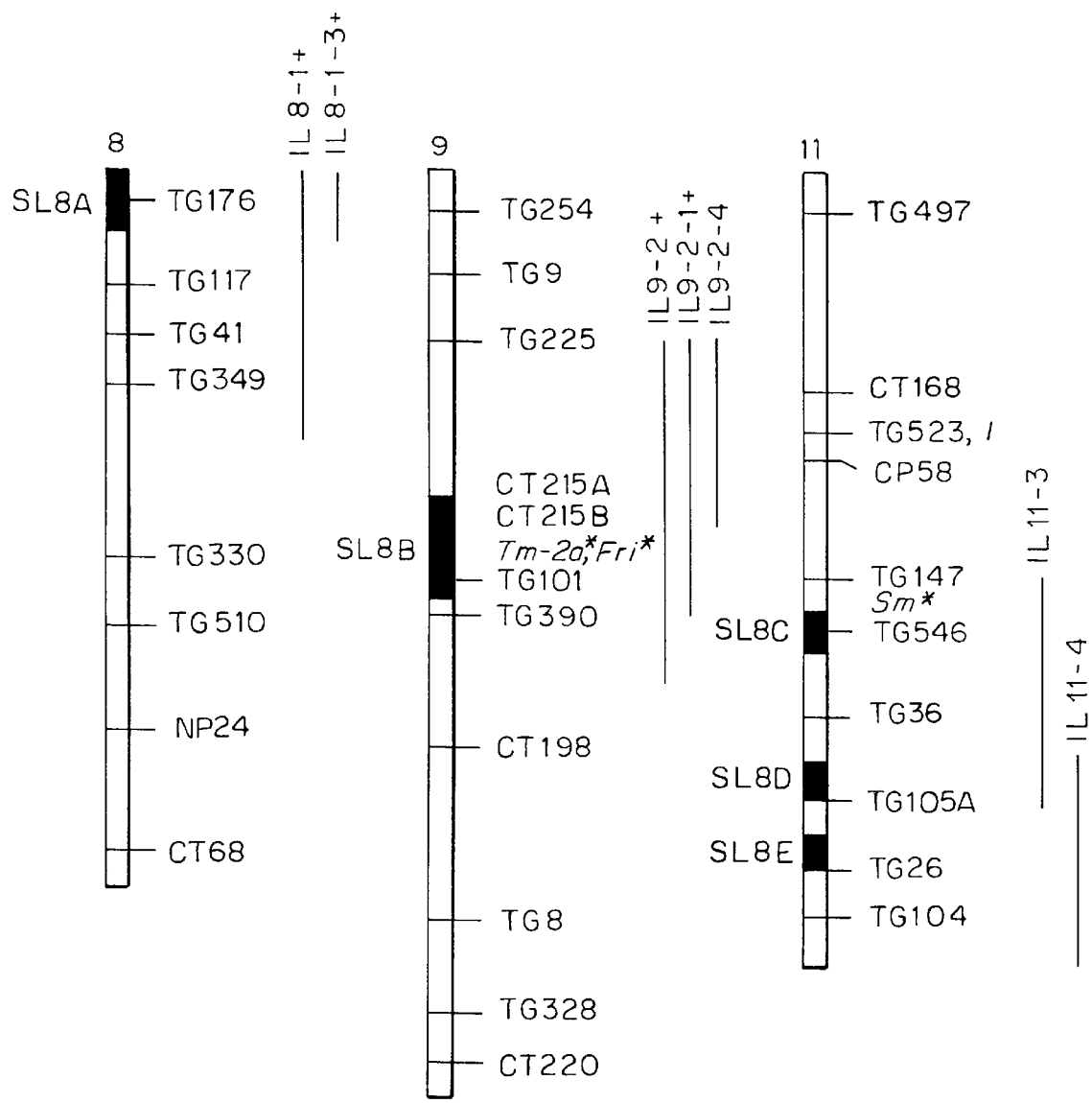
FIGS. 3A–B show distribution of SL8-homologues in the tomato genome. (1A) Linkage maps of chromosomes 8, 9 and 11. The linkage maps were adopted from Eshed et al. (1995). The relevant introgressed regions of the ILs are illustrated on the right of each tomato linkage map (solid lines). Asterisks indicate approximate map positions of known disease resistance genes. The mapped positions of the SL8 loci are indicated; (1B) Southern blot of TaqI digested DNA of representative ILs. *L. pennellii* fragments in the blot are designated A, B, C, D and E according to their genomic location, as indicated in panel A.
Figure 3B:
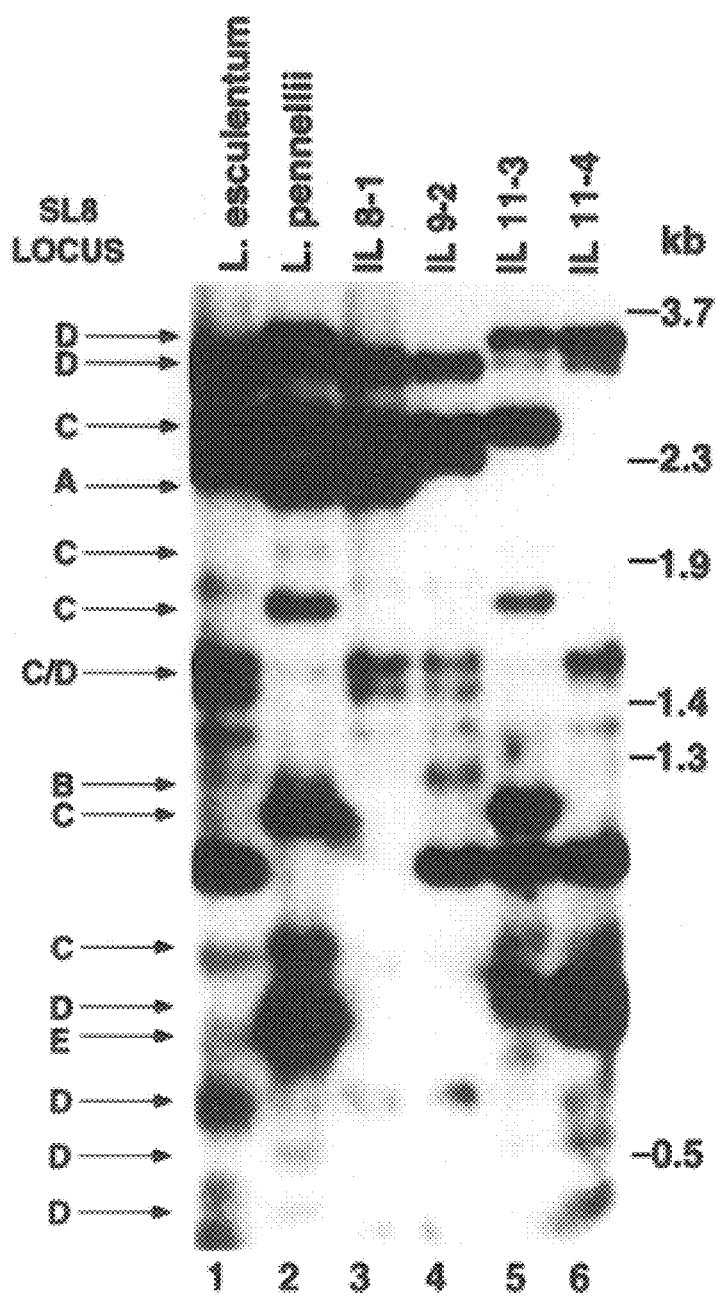

As only a subset of the SL8 copies showed polymorphism between the parents of the F2 populations used for mapping, additional populations were incorporated to map all the SL8 fragments. The first is an introgression-lines (IL) population, in which single chromosome segments from L. pennellii were introgressed into a L. esculentum background. Both parental species of the IL population carry the susceptible allele at the I2 locus (Eshed and Zamir, 1994). FIG. 3A illustrates the genomic segments introgressed from chromosomes 8, 9 and 11 in the IL lines, which proved relevant for the SL8 mapping. All SL8 copies appear to be polymorphic between L. esculentum and L. pennellii (FIG. 3B, lanes 1 and 2), a feature which facilitated their mapping. DNA digests from the IL lines were compared by southern blot hybridization with SL8 with that L. esculentum and L. pennellii (FIG. 3B). L. pennellii bands that are contained in each IL, as well as their allelic L. esculentum bands that are absent from these lines, represent SL8 copies that originate from the region introgressed in the respective line. One SL8 copy mapped to the short arm of chromosome 8 (SL8A ), as one L pennellii-type band is present, and one L. esculentum-type band is absent from IL 8-1. Similarly, one copy with weaker homology mapped near the centromere of chromosome 9 (SL8B; FIG. 3A,B). More accurate location of these two copies was obtained using lines containing shorter introgressed segments of the region, derived by selection of recombinants from the F2 of the original IL crossed back to L. esculentum var. M82 as illustrated in FIG. 3A. The rest of the SL8 copies mapped to the long arm of chromosome 11. Two of the introgression lines, IL 11-3 and IL 11-4, contain L. pennellii segments from the long arm of chromosome 11 (FIG. 3A). By comparing these two lines, three genetically distinct groups of SL8 family members could be identified on chromosome 11. The first (SL8C) maps to the region exclusively introgressed in IL 11-3, the second (SL8D) to the region of overlap between the IL 11-3 and IL 11-4, and the third (SL8E) to the region exclusively introgressed in IL 11-4. As previously established, the I2 resistance gene maps to the region of overlap designated SL8D.

Higher resolution mapping of the chromosome 11-based SL8 loci was accomplished using an F2 population of 150 plants, generated from an initial cross between L. esculentum and an introgression line that contains the long arm of chromosome 11 (line 11, Eshed et al., 1992). Analysis of the F2 population corroborated the division of SL8 markers into clusters. SL8C and SL8D congregated completely with the RFLP markers TG546 and 6-16, respectively, and SL8E mapped between markers TG26 and TG105, 0.25 cM from TG26 (FIG. 3) The susceptible-type L. esculentum is a common parent between the IL population and the F2 population. A comparison of the SL8 RFLP patterns of the ILs (FIG. 3) with those of resistant and susceptible L. esulentum plants (FIG. 2), shows clearly that nearly all fragments that belong to group SL8D are polymorphic between the resistant and susceptible F2 parents (compare FIG. 2 and FIG. 3). The nonpolymorphic bands in FIG. 2 belong mostly to the other groups. This indicates that the region containing cluster SL8D is the region which was originally introgressed from L. pimpinellifolium into L. esculentum.

Example 4

Heterogeneity in Recombination Rates in the I2 Region

Figure 11:
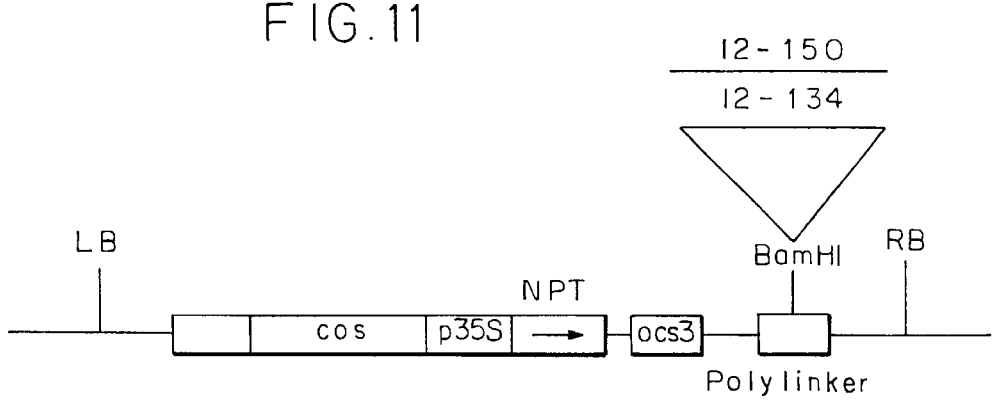
FIG. 11 depicts cosmids 12-134 and 12-150C, which contain the genes I2C-1 and I2C-2, respectively, in the BamHI site of cosmid TDNA 04541.
Figure 12A:
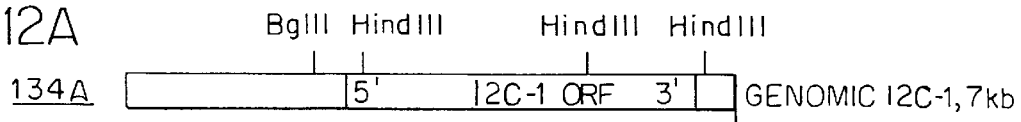
FIG. 12 shows sense constructs from the I2C-134 cosmid, which contains the genomic clone I2C-1 prepared in the PGA492 binaty vector.
Figure 12B:
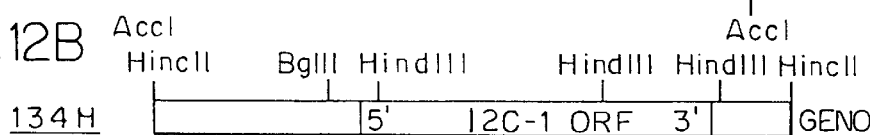
Figure 12C:
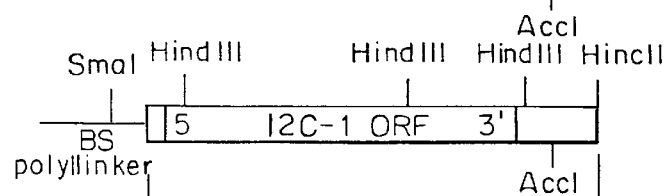
Figure 12D:
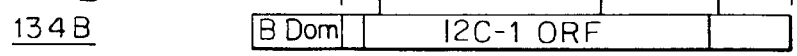

The locus SL8-D, containing at least 4 clustered members of the I2C family, spans a 0.03 cM region in the I2 locus. Two cosmid clones of approximately 20 kb insert from this cluster, I2C-134 and I2C-150 (FIG. 11), contain only one copy of SL8. Hence. 0.03 cM genetic interval spans at least 20 kb, which assigns an estimation of at least 670 kb/cM in the region containing this group. This ratio is similar to the average of 550 kb/cM over the entire genome. In contrast, in proximal regions the ratio is <150 kb/cM between D2 and SL8 (I2C-1; FIG. 1) and approximately 43 kb/cM between TG105A and TG26 (Segal et al., 1992). High variability in the physical to genetic ratio is common in the context of different regions of the chromosome, and is shown here to fluctuate regionally as well.

Example 5

I2C Genes Share Structural Similarity with a Family of Plant Resistance Genes Candidate members of the I2C gene family were isolated from genomic libraries of F.o.1 race 2 resistant tomatoes utilizing SL8 as a probe. The isolated clones were compared to the genomic DNA on southern blots, and clones that contain resistant-type polymorphic bands from the SL8D locus were further characterized. The cosmid clone I2C-134 (FIGS. 11, 12) contains the I2C-1 gene, teat includes in its 3' region the SL8 marker (FIG. 1C). It was found to contain the polymorphic bands TR1 and TR5 (FIG. 2). I2C-134 also exhibits resistant-type polymorphic bands after digestion with other endonucleases, such as HindIII, DraI and EcoRI (data not shown) Cosmid I2C-150 (FIG. 11) contains another gene, 12(C-2, represented by the polymorphic bands TR4 and TR7 (FIG. 2). As the recombination in individual BR 30(5) has occurred between band TR7 and the other resistant-type bands, it would be expected that the gene which contains TR7 will not contain other resistant-type bands. The presence of both TR4 and TR7 bands It I2C-150 could be explained either by a recombination within the gene I2C-2 in the individual BR 30(5), or by comigration of bands of different origin. Other cosmids isolated contained non-polymorphic bands, and were not sequenced.

Figure 9:
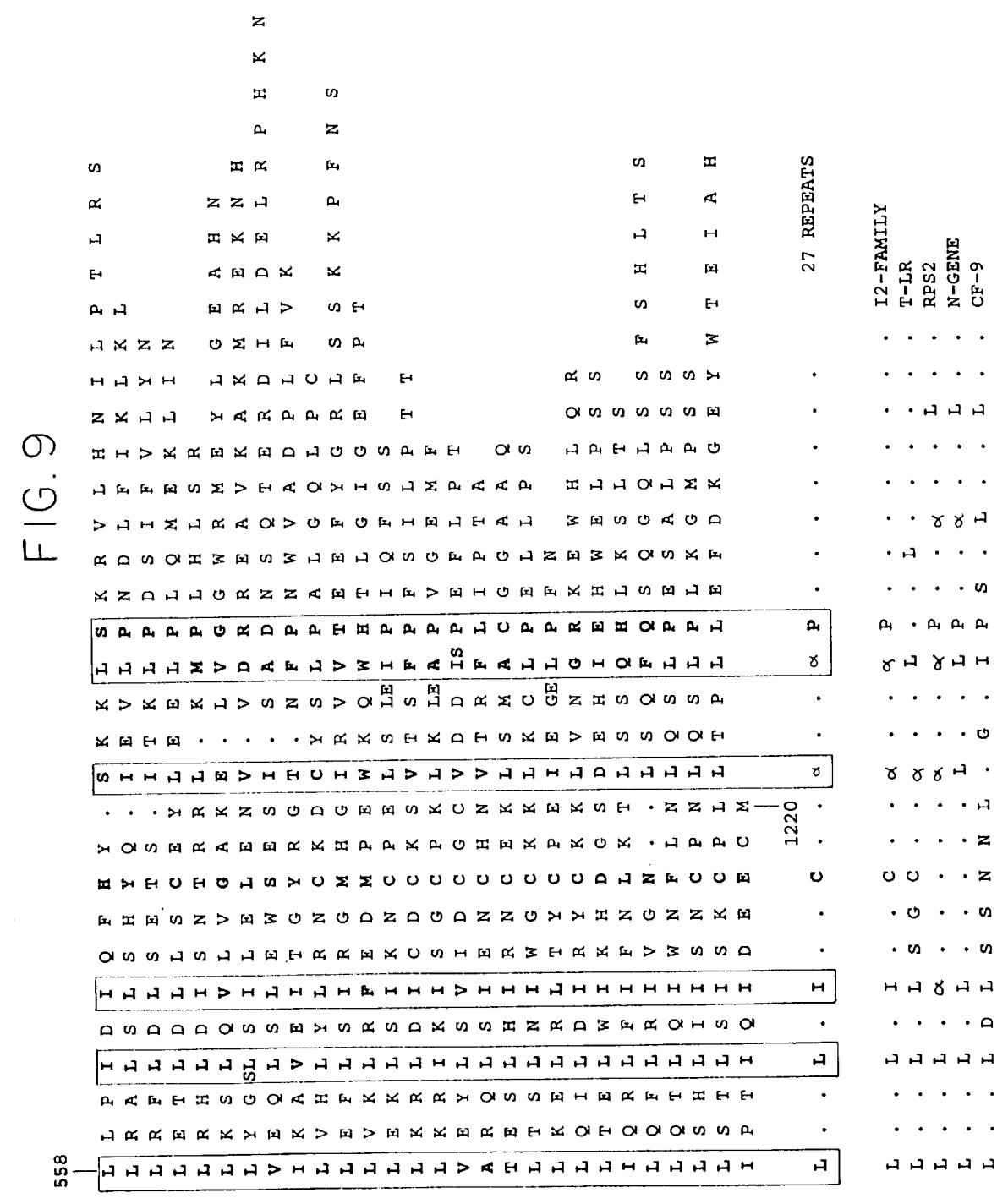

One continuous open reading frame was identified in each of the genes I2C-1 and I2C-2. FIG. 8 shows a comparison between the deduced amino acid sequences of the I2C-1 and the I2C-2 genes and recently isolated plant resistance genes. Although the overall homology is rather low, an intriguing structural similarity is apparent. All genes contain in their N terminus a conserved nucleotide binding site, P-loop, and other conserved amino acid stretches of unknown function, which are shown in FIG. 8 as boxes I–VI In their C terminus they all display a long region of leucine-rich-repeats (LRR), which spans at least half of the gene. The LRR of I2C-1 are aligned in FIG. 9. The N terminal parts of the I2C repeat segment are comparable to the consensus LRR found in the resistance genes RPS2, N gene and L6, and to the consensus of the T-LR VSG expression site associated gene from Trypanosoma (FIG. 9, Ross et al., 1991; Smiley et al., 1990). The latter protein shares 52% similarity and 25% Identity with the 3' part of I2C-1. The C-terminal parts of the repeat segments are not conserved, and are of variable length.

Example 6

Transcribed Sequences from the I2C Gene Family Contain Insertion and Frame-shifts.

In order to compare different resistant-type members of the I2C family, three different cDNA libraries of resistant tomato varieties were screened with the SL8 probe. Fifteen independent clones were isolated, and all of them were shorter than I2C-1, containing only the 3' ends of the genes. The reason for obtaining only partial clones is not known, as much longer inserts have been isolated from these libraries. Two of the longest clones, designated I2C-3 and I2C-4, of 1200 and 1600 bp long, respectively, were sequenced. Interestingly, one of the cDNA clones, I2C-4, contains two frame shifts, and thus, if translated, would result in a truncated peptide. In FIG. 10, I2C-4 is artificially shown as a continuous chimera of the 3 different ORFs, and the junctions are indicated with arrows. The comparison of the 3' region of the two genomic and two cDNA clones is shown in FIG. 10. Striking insertions or deletions, chiefly in the C-terminal region, can be observed. Most insertions are shared by at least two different genes, though the combinations are different for each insertion. Interestingly, close to the C-terminus the different genes contain between 2 and 6 repeats of an almost identical sequence. These repeats are indicated in FIG. 10. The largest insertions in genes I2C-3 and I2C-4 are made up exclusively of these repeats.

Example 7

Plant Transformation Procedures

In order to correlate the disease resistance capacity of the I2C genes, they have been transformed into tomato plants in a few different formats:

(a) Cosmid clones I2C-134 and I2C-150 containing the complete inserts of clones I2C-1 and I2C-2, respectively, in the BamHI site of cosmid TDNA 04541 (Jones et al., 1992) (FIG. 11), were directly transformed into sensitive tomato lines VF-36 and Money Maker (Jones et al., 1992). Another 10 cosmids have been isolated by homology to I2C and were similarly transformed. To this end the cosmids were transferred into Agrobacterium tumefaciens using, standard transformation procedures. The binary vector A. tumefaciens LBA 4404 is suitable for the transformation procedure. Tomato explants are inoculated as described in Jones et al., 1992.

(b) Similarly, clone I2C-1 was introduced into the PGA492 binary vector supplemented with the B-domain of the 35S promoter (constructs 134 A and 134H) and were directly transformed into the same sensitive tomato lines as described above.

FIG. 12 depicts sense constructs from the I2C-134 cosmid containing the I2C-1 clone in the PGA492 binary vector. A depicts an AccI subclone, I134A, containing approximately 3 kb upstream and 300 bp downstream to the open reading frame (ORF), cloned into the ClaI site of the PGA492 vector; B. depicts a Hincli subclone, 134H, containing around 3 kb upstream and 800 bp downstream to the translated region, cloned into the HpaI site of the PGA492 vector; D depicts a small subclone from the BS subclone of cosmid 134 depicted in C, containing 300 bp upstream and 800 bp downstream to the translated region, cloned downstream from the B domain (B Dom) of the 35S promoter, in the PGA492 vector, to create 134B.

(c) Antisense and sense partial clones were constructed with partial sequence; from I2C-1, 12C-2, and I2C-3, and subcloned into 35S omega expression vectors in the PGA492 binary vector. These constructs (2-1, 6-3, 5-1 and 31-17) were transformed into resistant tomato lines (Motelle) as described in section (a) above.

Figure 13:
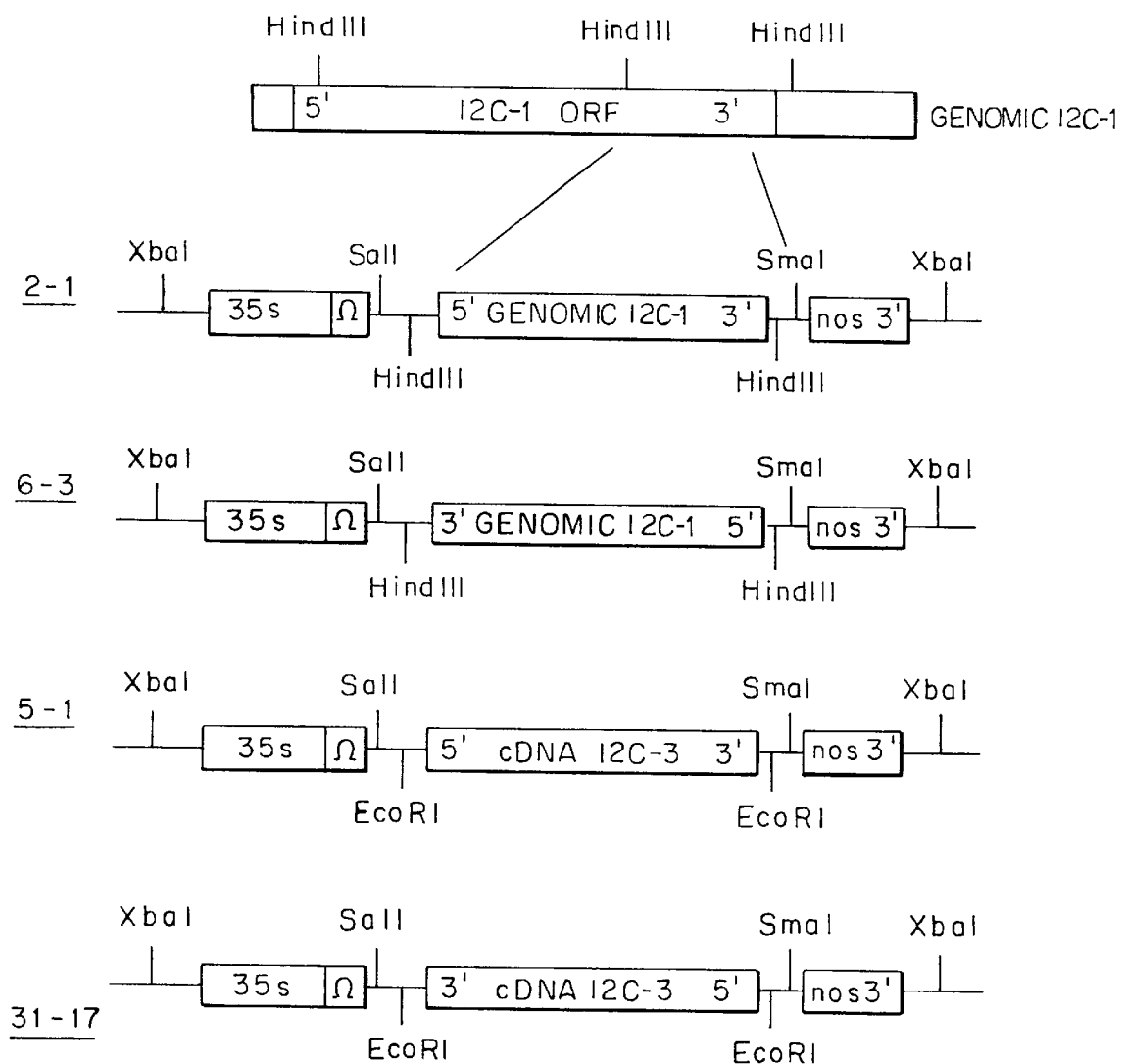
FIG. 13 shows sense (2-1 and 5-1) and antisense (6-3 and 31-17) constructs comprising the genomic clone I2C-1 or the cDNA clone I2C-3 for transformation of Fusarium resistant plants.

FIG. 13 depicts the antisense and sense constructs 2-1, 6-3, 5-1 and 31-17 for transformation of Fusarium resistant tomatoes. On the top is a map of SL8-134 (I2); indicated is the HindIII fragment used for the antisense and sense cloning in 2-1 and 6-3, which spans nucleotides 2540–3716 in the I2C-1 sequence shown in FIG. 4. Constructs 5-1 and 31-17 contain the full-length insert of cDNA I2C-3. 35S is the cauliflower mosaic virus (CaMV) 35S promoter, Ω is a translation enhancer from tobacco mosaic virus, and nos 3' is a terminator, 3' untranslated sequence of the nopaline synthase gene. All the clones were prepared in the PAG492 binary vector using the unique XbaI site.

The resulting transformed tomato lines are tested for complementation of Fusarium resistance in sensitive lines like Money Maker or abrogation of Fusarium resistance in the Motelle line. Tests are carried out by inoculating 10 days old seedlings with freshly prepared Fusarium fungus cultures and disease is estimated during 10–20 days following inoculation. Sensitive plants show retarded growth browning of vascular tissue and usually dye within 20 days.

REFERENCES

An, G., (1986) *Plant Physiol*. 81, 86–91.

Behare, J., Laterrot, H., Sarfatti, M., and Zamir, D. (1991). Restriction fragnent length polymorphism mapping of the Stemphylium resistance gene in tomato. *Mol. Plant-Microbe Interact*. 4, 489–492.

Bent, A. F., Kunkel, B. N., Dahlbeck, D., Brown, K. L., Schmidt, R., Giraudat, J., Leung, J., and Staskawicz, B. J. (1994). RPS2 of *Arabidopsis thaliana*: A leucine-rich repeat class of plant disease resistance genes. *Science* 265, 1856–1860.

Bournival, B. L., Vallejos, C. E., and Scott, J. W. (1990). Genetic analysis of resistances to races 1 and 2 of *Fusarium oxysporum* f. sp. *lycopersici* from the wild tomato *Lycopersicon pennellii*. *Theor. Appl. Genet*. 79, 641–645.

Briggs, S. P., and Johal, G. S. (1994). Genetic patterns of plant host-parasite interactions. *TIBS* 10, 12–16.

Busch, S. J., and Sassone-Corsi, P. (1990). Dimers, leucine zippers and DNA-binding domains. *TIG* 6, 36–40.

Colicelli, J., Field, J., Ballester, R., Chester, N., Young, D., and Wigler, M. (1990). Mutational mapping of RAS-responsive domains of the *Saccharomyces cerevisiae* adenylyl cyclase. *Mol. Cell. Biol*. 10, 2539–2543.

Dangl, J. L. (1995). Piece de Resistance: Novel classes of plant disease resistance genes. *Cell* 80, 363–366.

Dekeyser, R. A. et al., (1990) *Plant Cell* 2, 591–602.

Depicker, A., Stachel, S., Dhaese, P., Zambryski, P. and Goodman, H. M. (1982) Nopaline synthase: Transcript Mapping and DNA Sequence. *J. Molec. Appl. Genetics* 561–573.

Devereux, J., Haeberli, P. and Smithies O. (1984). A comprehensive set of sequence analysis programs for the VAX. *Nucl. Acids Res*. 12, 387–395.

Elias, K. S., Zamir, D., Lichtman-Pleban, T., and Katan, T. (1993). Population structure of *Fusarium oxysporum* f. sp. *lycopersici*: restriction fragment length polymorphisms provide genetic evidence that vegetative compatibility group is an indicator of evolutionary origin. *Mol. Plant-Microbe Interact*. 6, 565–572.

Ellis, J. G., Lawrence, G. J., Finnegan, E. J., and Anderson, P. A. (1995). Contrasting complexity of two rust resistance loci in flax. *Proc. Natl. Acad. Sci. USA* 92, 4185–4188.

Eshed, Y., Abu-Abied, M., Saranga, Y., and Zamir, D. (1992). *Lycopersicon esculentum* lines containing small overlapping introgressions from *L. pennellii*. *Theor. Appl. Gen*. 83, 1027–1034.

Eshed, Y., and Zamir. D. (1994). A genomic library of *lycopersicon pennellii. L. esculentum*: a tool for fine mapping of genes. Euphytica 79, 175–179.

Eshed Y. and Zamir, D. (1995). An introgression line population of *L. pinnellii* in the cultivated tomato enables the identification and fine mapping of yield associated QTL. *Genetics*, in press.

Eyal, Y., Meller, Y., Lev-Yadun, S. and Fluhr, R. (1993) A basic-type promoter directs ethylene responsiveness and abscission zone-specific expression. *The Plant J*. 4,225–235.

Gallie, D. R. et al. (1987) *Nucl. Acid Res*. 15, 3257–3273.

Gordon-Kahn, W. J. et al. (1990) *Plant Cell* 2, 603–618.

Grant, M. R., Laurence, G., Straube, E., Ashfield, T., Lewald, J., Sattler, A., Innes;, R. w., Dangl, J. (1995). Structure of the Arabidopsi RPM1 gene enabling dual specificity disease resistance. *Science* 269, 843–846.

Greve, H. D. et al. (1983) *J. Mol. Appl. Genet*. 1, 499–511.

Hayashimoto, A. et al. (1990) *Plant Physiol*. 93. 857–863.

Horsch, R. B. et al., (1985) *Science* 227, 1229–1231.

Johal, G. S., and Briggs, S. P. (1992). Reductase activity encoded by the HM1 disease resistance gene in maize. *Science* 258, 985–987.

Jones, D. A., Thomas, C. M., Hammond-Kosack, K. E., Balint-Kurti, P. J., and Jones, J. D. G. (1994). Isolation of the tomato Cf-9 gene for resistance to *Cladosporium fulvum* by transposon tagging. *Science* 266, 789–793.

Jones, J. D. G., Shlumukov, L., Carland, F., English, J., Scofield, S. R., Bishop, G., and Harrison, K. (1992). Effective vectors for transformation, expression of heterologous genes, and assaying transposon excision in transgenic plants. *Transgenic Research* 1, 283–297, Kobe, B., and Deisenhofer, J. (1993). Crystal structure of porcine ribonucl,aase inhibitor, a protein with leucine-rich repeats. *Nature* 366, 751–756.

Kobe. B., and Deisenhofer, J. (1994). The leucine-rch repeat: a versatile binding motif. *TIBS* 19, 415–421.

Kobe, B., and Deisenhofer, J. (1995). A structural basis of the interactions between leucine-rich repeats and protein ligands. *Nature* 374, 183–185.

Laterrot, H., and Moretti, A. (1995). Confinnation of the linkage Tm-2, ah, Frl. *TGC* 45, 29.

Lawrence, G. J., Finnegan, E. J., Ayliffe, M. A., and Ellis J. G. (1995). The L6 gene for flax rust resistance is related to the Arabidopsis bacterial resistance gene RPS2 and the tobacco viral resistance gene N. *Plant Cell* 7, 1195–1206.

Martin, G. B., Ganal, M. W. and Tanksley, S. (1992). Construction of a yeast artificial chromosome library of tomato and identification of cloned segments linked to two disease resistance loci. Mol. Gen. Genet. 233, 25–32.

Martin, G. B., Brommonschenkel, S. H., Chunwongse, J., Frary, A., Ganal, M. W., Spivey, R., Wu, T., Earle, E. D., and Tantksley, S. D. (1993). Map-based cloning of a protein kinase gene conferring disease resistance in tomato. *Science* 262, 1432–1436.

Mindrinos, M., Katagiri, F., Yu, G.-L., and Ausubel, F. M. (1994). The *A. Thaliana* disease resistance gene RPS2 encodes a protein containing a nucleotide-binding site and leucine rich repeats. *Cell* 78, 1089–1099.

Ori, N., Paran, I., Aviv, D., Eshed, Y., Tanksley. S., Zamir, D., and Fluhr, R (1994). A genomic search for the gene conferring resistance to Fusarium wilt in tomato. *Euphytica* 79, 201–204.

Ross, D. T., Raibaud, A., Florent, I. C., Sather. S., Gross, M. K, Storm, D. R., and Eisen, H. (1991). The trypanosome VSG expression site encodes adenylate cyclase and a leucine-rich putative regulatory gene. *EMBO J*. 10, 2047–2053.

Saraste, M., Sibbald, P. R., and Wittinghofer, A. (1990). The P-loop a common motif in ATP- and GTP-binding proteins. TIBS 15, 430–434.

Scott, J. W., and Jones, J. P. (1991). Genetic control of resistance to races 1, 2 and 3 of Fusarium wilt. *TGC* 41, 47.

Segal, G., Sarfatti, M., Schaffer, M. A., Ori N., Zamir, D., and Fluhr, R. 199). Correlation of genetic and physical structure in the region surrounding the I₂ *Fusarium oxysporum* resistance locus in tomato. *Mol. Gen. Genet.* 231, 179–185.

Smiley, B. L., Stadnyk, A. W., Myler, P. J., and Stuart, K. (1990). The trypanosome leucine repeat gene in the variant surface glycoprotein expression site encodes a putative metal-binding domain and a region resembling protein-binding domains of yeast Drosophila and mammalian proteins. *Mol. Cell. Biol.* 10, 6436–6444.

Staskawicz, B. J., Ausubel, F. M., Baker, B. J., Ellis, J. G., and Jones, J. D. G. (1995). Molecular Genetics of Plant Disease Resistance. *Science* 268, 661–666.

Tanksley, S. D., Ganal, M. W., Prince, J. C., de Vicente, M. C., Bonierabale, N. W., Broun, P., Fulton, T. M., Giovanonni, J. J., Grandillo, S., Martin, G. B., Messeguer, R., Miller, J. C., Miller, L., Paterson, A. H., Pineda, O., Roder, M. S., Wing, R. A., Wu, W. and Young, N. D. (1992). High density molecular linkage maps of the tomato and potato genomes. *Genetics* 132: 1141–1160.

Tanksley, S. D., Ganal, M. W. and Martin, G. B. (1995) Chromosome landing: a paradigm for map-based gene cloning in plants with large genomes. *TIG* 11, 63–68.

Whitham, S., Dinesh-Kumar, S. P., Choi, D., Hehl, R., Corr, C., and Baker, B. (1994). The product of the tobacco mosaic virus resistance gene N: Similarity to toll and the interleukin-1 receptor. *Cell* 78, 1101–1115.

Young, N. D., Zamir, D., Ganal, M. W., and Tanksley, S. D. (1988). Use of isogenic lines and simultaneous probing to identify DNA markers tightly linked to the Tm-2a gene in tomato. *Genetics* 120, 579–585.

What is claimed is:

1. An isolated DNA molecule which, when recombinantly transferred into a non-resistant tomato plant, expresses a protein which confers resistance to Fusarium oxysporum f.sp lycopersici race 2, comprising:
   (a) a DNA molecule comprising the nucleotide sequence of SEQ ID NO:1;
   (b) a DNA molecule capable of hybridization with SEQ ID NO:1 under conditions of 6×SSC, 0.5% SDS at 65° C., washing at 2×SSC at room temperature, and which encodes a protein which confers resistance to Fusarium oxysporum f.sp lycopersici race 2; or
   (c) a DNA molecule which encodes a protein encoded by the DNA of (a) or (b).

2. A gene construct containing a DNA molecule according to claim 1.

3. A gene construct according to claim 2 wherein said DNA molecule includes regulatory sequences that flank the coding region.

4. A cosmid into which is subcloned a gene construct according to claim 3.

5. A gene construct according to claim 2 which further comprises DNA regulatory sequences enabling the expression of said DNA molecule in plant cells.

6. An expression vector comprising a gene construct according to claim 5 wherein said DNA regulatory sequences comprise a plant promoter, a DNA sequence that enhances translation of the mRNA transcribed from said DNA molecule and a polyadenylation/terminator sequence.

7. A tomato cell line or plant line transformed with a cosmid into which is subcloned a gene construct wherein said DNA molecule includes regulatory sequences that flank the coding region with an expression vector according to claim 5.

8. An isolated DNA molecule useful as a PCR primer or a probe for detecting the presence of the Fusarium wilt gene resistance family in the DNA of a tomato plant, consisting of:

a DNA molecule comprising the nucleotide sequence of SEQ ID NO:1;

a DNA molecule comprising the nucleotide sequence of SEQ ID NO:3;

a DNA molecule comprising the nucleotide sequence of SEQ ID NO:5;

a DNA molecule comprising the nucleotide sequence of SEQ ID NO:6; or a DNA molecule capable of hybridization with any one of SEQ ID NOs:1, 3, 5 or 6 under hybridization conditions of 6×SSC, 0.5% SDS at 65° C., washing at 2×SSC at room temperature.

9. A transgenic tomato, plant recombinantly transformed with a DNA molecule in accordance with claim 1 in such a manner as to confer resistance to *Fusarium oxysporum* f.sp *lycopersici* race 2.

10. A seed of a transgenic tomato plant recombinantly transformed with a DNA molecule in accordance with claim 1 in such a manner as to confer resistance to *Fusarium oxysporum* f.sp *lycopersici* race 2.

* * * * *

UNITED STATES PATENT AND TRADEMARK OFFICE
CERTIFICATE OF CORRECTION

PATENT NO. : 6,100,449
DATED : August 8, 2000
INVENTOR(S) : Robert Fluhr et al.

It is certified that error appears in the above-identified patent and that said Letters Patent is hereby corrected as shown below:

Title page,
Item [73], Assignee, delete "Yissum Reseearch and Development Company" and insert therefor -- Yissum Research Development Company of the Hebrew University of Jerusalem --.

Signed and Sealed this

Twenty-fifth Day of October, 2005

JON W. DUDAS
*Director of the United States Patent and Trademark Office*

SEQUENCE LISTING

```
(1) GENERAL INFORMATION:

(iii) NUMBER OF SEQUENCES: 12

(2) INFORMATION FOR SEQ ID NO: 1:

(i) SEQUENCE CHARACTERISTICS:
        (A) LENGTH: 4946 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION:299..3958

(xi) SEQUENCE DESCRIPTION: SEQ ID NO: 1:

ATCTCAACTC TTCACAATTC TAAAATGTAT TGATTATATG GTAGGCCCCA CTACAATGAG         60

CTGTTGAAAA ATGGACTCAA TTATTCTATT CAAGTCAATA CTTTTTGAGA AGAGAAAAGA        120

GGACAGTTTT GATTAGCTGA AAAATAGTTG TACTAATTTC AAGCAATCAC TAATCATTCT        180

TGTTTGCAAA TTACTCTCAA CATTCAACGG GTAAAGTGAA GTACTATCTT TGTAGTTGAA        240

GATAGAAGAA AAATTTATCT TCTCAAAATC ATTTTGTGTT CCCTTGCAGA TTTGAGAA         298

ATG GAG ATT GGG TTA GCA ATT GGT GGT GCA TTT CTC TCC TCA GCT TTG        346
Met Glu Ile Gly Leu Ala Ile Gly Gly Ala Phe Leu Ser Ser Ala Leu
  1               5                  10                  15

AAT GTT CTG TTT GAT AGG CTT GCT CCT AAT GGT GAT CTG CTC AAC ATG        394
Asn Val Leu Phe Asp Arg Leu Ala Pro Asn Gly Asp Leu Leu Asn Met
             20                  25                  30

TTT CGG AAG CAT ACA GAT GAT GTT GAG CTC TTT GAG AAG CTG GGG GAC        442
Phe Arg Lys His Thr Asp Asp Val Glu Leu Phe Glu Lys Leu Gly Asp
         35                  40                  45

ATT TTG CTT AGT CTT CAA ATT GTG CTA AGT GAT GCA GAG AAT AAG AAA        490
Ile Leu Leu Ser Leu Gln Ile Val Leu Ser Asp Ala Glu Asn Lys Lys
     50                  55                  60

GCA TCG AAT CAA TTT GTG AGC CAG TGG TTA CAT AAG CTT CAG ACT GCT        538
Ala Ser Asn Gln Phe Val Ser Gln Trp Leu His Lys Leu Gln Thr Ala
 65                  70                  75                  80

GTG GAC GCT GCT GAA AAC TTG ATA GAA CAA GTC AAT TAT GAA GCT TTG        586
Val Asp Ala Ala Glu Asn Leu Ile Glu Gln Val Asn Tyr Glu Ala Leu
                 85                  90                  95
```

```
                                                                -continued

AGG CTT AAA GTG GAA ACA AGC AAC CAG CAA GTA AGT GAC CTC AAC CTG          634
Arg Leu Lys Val Glu Thr Ser Asn Gln Gln Val Ser Asp Leu Asn Leu
        100                 105                 110

TGC TTG AGT GAT GAT TTC TTT CTT AAC ATA AAG AAG AAG TTG GAA GAC          682
Cys Leu Ser Asp Asp Phe Phe Leu Asn Ile Lys Lys Lys Leu Glu Asp
            115                 120                 125

ACT ATT AAA AAA CTG GAG GTG TTG GAA AAG CAA ATT GGT CGC CTT GGC          730
Thr Ile Lys Lys Leu Glu Val Leu Glu Lys Gln Ile Gly Arg Leu Gly
    130                 135                 140

TTA AAG GAG CAT TTT ATT TCG ACC AAA CAA GAA ACT AGA ACA CCT TCA          778
Leu Lys Glu His Phe Ile Ser Thr Lys Gln Glu Thr Arg Thr Pro Ser
145                 150                 155                 160

ACT TCT TTG GTT GAT GAT TCT GGT ATC TTT GGA AGG AAG AAT GAA ATA          826
Thr Ser Leu Val Asp Asp Ser Gly Ile Phe Gly Arg Lys Asn Glu Ile
                165                 170                 175

GAG AAT TTG GTT GGC CGT TTG TTG TCT ATG GAT ACA AAG CGA AAA AAT          874
Glu Asn Leu Val Gly Arg Leu Leu Ser Met Asp Thr Lys Arg Lys Asn
            180                 185                 190

CTG GCT GTA GTT CCT ATT GTG GGA ATG GGC GGC ATG GGT AAG ACA ACA          922
Leu Ala Val Val Pro Ile Val Gly Met Gly Gly Met Gly Lys Thr Thr
        195                 200                 205

CTT GCT AAA GCC GTT TAC AAT GAT GAG AGA GTG CAG AAA CAT TTT GGT          970
Leu Ala Lys Ala Val Tyr Asn Asp Glu Arg Val Gln Lys His Phe Gly
    210                 215                 220

TTG ACA GCT TGG TTT TGT GTT TCT GAG GCA TAT GAT GCT TTC AGA ATA         1018
Leu Thr Ala Trp Phe Cys Val Ser Glu Ala Tyr Asp Ala Phe Arg Ile
225                 230                 235                 240

CCA AAA GGT TTA CTT CAA GAA ATT GGA TCA ACT GAC TTG AAG GCT GAT         1066
Pro Lys Gly Leu Leu Gln Glu Ile Gly Ser Thr Asp Leu Lys Ala Asp
                245                 250                 255

GAC AAT CTT AAT CAG CTA CAA GTC AAA TTG AAG GCT GAT GAC AAT CTT         1114
Asp Asn Leu Asn Gln Leu Gln Val Lys Leu Lys Ala Asp Asp Asn Leu
            260                 265                 270

AAT CAG CTA CAA GTC AAA TTG AAG GAA AAG CTG AAT GGA AAA AGG TTT         1162
Asn Gln Leu Gln Val Lys Leu Lys Glu Lys Leu Asn Gly Lys Arg Phe
        275                 280                 285

CTT GTT GTC CTT GAT GAC GTG TGG AAT GAT AAT TAT CCT GAG TGG GAT         1210
Leu Val Val Leu Asp Asp Val Trp Asn Asp Asn Tyr Pro Glu Trp Asp
    290                 295                 300

GAC TTG AGA AAT CTT TTT TTA CAA GGG GAT ATA GGA AGT AAG ATC ATT         1258
Asp Leu Arg Asn Leu Phe Leu Gln Gly Asp Ile Gly Ser Lys Ile Ile
305                 310                 315                 320

GTA ACG ACA CGT AAA GAG AGT GTT GCC TTG ATG ATG GAT AGT GGG GCA         1306
Val Thr Thr Arg Lys Glu Ser Val Ala Leu Met Met Asp Ser Gly Ala
                325                 330                 335

ATC TAC ATG GGA ATT CTG TCT AGT GAA GAC TCT TGG GCT CTA TTC AAA         1354
Ile Tyr Met Gly Ile Leu Ser Ser Glu Asp Ser Trp Ala Leu Phe Lys
            340                 345                 350

CGA CAT TCA TTA GAG CAC AAG GAT CCC AAG GAA CAT CCA GAA TTT GAA         1402
Arg His Ser Leu Glu His Lys Asp Pro Lys Glu His Pro Glu Phe Glu
        355                 360                 365

GAG GTT GGA AAA CAA ATT GCA GAC AAG TGC AAA GGG TTG CCT TTA GCT         1450
Glu Val Gly Lys Gln Ile Ala Asp Lys Cys Lys Gly Leu Pro Leu Ala
    370                 375                 380

CTA AAA GCA CTT GCT GGT ATG TTA CGC AGC AAA TCA GAG GTG GAT GAG         1498
Leu Lys Ala Leu Ala Gly Met Leu Arg Ser Lys Ser Glu Val Asp Glu
385                 390                 395                 400

TGG AGA AAC ATT TTA CGA AGT GAA ATA TGG GAG CTT CCA AGT TGT TCG         1546
Trp Arg Asn Ile Leu Arg Ser Glu Ile Trp Glu Leu Pro Ser Cys Ser
                405                 410                 415
```

-continued

| | | |
|---|---|---|
| AAT GGT ATA TTA CCA GCG CTA ATG TTG AGC TAC AAT GAT CTC CCT GCA<br>Asn Gly Ile Leu Pro Ala Leu Met Leu Ser Tyr Asn Asp Leu Pro Ala<br>420                             425                           430 | | 1594 |
| CAT TTA AAG CAA TGT TTG GCT TAT TGT GCA ATA TAT CCC AAA GAT TAT<br>His Leu Lys Gln Cys Leu Ala Tyr Cys Ala Ile Tyr Pro Lys Asp Tyr<br>             435                           440                     445 | | 1642 |
| CAA TTT CGC AAA GAG CAA GTT ATT CAC CTG TGG ATT GCT AAT GGT CTT<br>Gln Phe Arg Lys Glu Gln Val Ile His Leu Trp Ile Ala Asn Gly Leu<br>450                           455                           460 | | 1690 |
| GTA CAT CAG TTT CAT TCG GGT AAC CAA TAC TTT ATC GAG TTG AGA TCA<br>Val His Gln Phe His Ser Gly Asn Gln Tyr Phe Ile Glu Leu Arg Ser<br>465                       470                         475                   480 | | 1738 |
| AGA TCA TTG TTC GAA ATG GCC TCA GAG CCT TCT GAA AGA GAC GTA GAG<br>Arg Ser Leu Phe Glu Met Ala Ser Glu Pro Ser Glu Arg Asp Val Glu<br>                         485                         490                     495 | | 1786 |
| GAA TTC TTA ATG CAT GAC CTT GTC AAT GAT TTG GCA CAA ATT GCA TCT<br>Glu Phe Leu Met His Asp Leu Val Asn Asp Leu Ala Gln Ile Ala Ser<br>                     500                         505                     510 | | 1834 |
| TCA AAT CAT TGT ATA AGG TTG GAA GAT AAC AAA GGA TCG CAT ATG TTG<br>Ser Asn His Cys Ile Arg Leu Glu Asp Asn Lys Gly Ser His Met Leu<br>         515                         520                         525 | | 1882 |
| GAA CAA TGT CGG CAC ATG TCC TAT TCA ATA GGA CAA GAT GGT GAG TTT<br>Glu Gln Cys Arg His Met Ser Tyr Ser Ile Gly Gln Asp Gly Glu Phe<br>530                           535                          540 | | 1930 |
| GAG AAA TTG AAA TCA CTC TTT AAA TCA GAG CAG CTG AGG ACA TTA CTT<br>Glu Lys Leu Lys Ser Leu Phe Lys Ser Glu Gln Leu Arg Thr Leu Leu<br>545                         550                         555                   560 | | 1978 |
| CCA ATC GAT ATC CAG TTC CAT TAC TCA AAA AAA CTA AGC AAG AGG GTG<br>Pro Ile Asp Ile Gln Phe His Tyr Ser Lys Lys Leu Ser Lys Arg Val<br>                     565                         570                     575 | | 2026 |
| TTG CAT AAC ATA CTG CCT ACA CTA AGA TCC TTG AGG GCA CTA TCA TTG<br>Leu His Asn Ile Leu Pro Thr Leu Arg Ser Leu Arg Ala Leu Ser Leu<br>                       580                         585                     590 | | 2074 |
| TCT CAT TAC CAG ATT GAG GTG TTG CCA AAT GAC TTG TTT ATC AAA TTA<br>Ser His Tyr Gln Ile Glu Val Leu Pro Asn Asp Leu Phe Ile Lys Leu<br>         595                         600                         605 | | 2122 |
| AAG CTC CTC AGA TTT TTG GAC CTT TCT GAG ACA TCG ATT ACA AAG TTG<br>Lys Leu Leu Arg Phe Leu Asp Leu Ser Glu Thr Ser Ile Thr Lys Leu<br>610                           615                         620 | | 2170 |
| CCG GAT TCC ATT TTT GTG TTG TAT AAC TTA GAG ACA CTT CTC CTG TCA<br>Pro Asp Ser Ile Phe Val Leu Tyr Asn Leu Glu Thr Leu Leu Leu Ser<br>625                         630                        635                   640 | | 2218 |
| TCT TGT GAA TAT CTT GAG GAG CTA CCG CTG CAG ATG GAG AAG TTG ATT<br>Ser Cys Glu Tyr Leu Glu Glu Leu Pro Leu Gln Met Glu Lys Leu Ile<br>             645                           650                     655 | | 2266 |
| AAC TTG CGT CAT CTT GAC ATA AGC AAC ACT CGG CGC TTG AAG ATC CCA<br>Asn Leu Arg His Leu Asp Ile Ser Asn Thr Arg Arg Leu Lys Ile Pro<br>                   660                         665                     670 | | 2314 |
| CTA CAT CTG AGC AGG TTG AAA AGC CTC CAA GTG TTG GTG GGA GCC AAG<br>Leu His Leu Ser Arg Leu Lys Ser Leu Gln Val Leu Val Gly Ala Lys<br>         675                         680                         685 | | 2362 |
| TTT CTT GTA GGT GGT TGG AGA ATG GAA TAT TTG GGT GAA GCA CCC AAC<br>Phe Leu Val Gly Gly Trp Arg Met Glu Tyr Leu Gly Glu Ala Pro Asn<br>690                           695                          700 | | 2410 |
| TTA TAT GGA TCT CTA TCA ATT CTA GAG TTG GAA AAT GTG GTT GAT AGA<br>Leu Tyr Gly Ser Leu Ser Ile Leu Glu Leu Glu Asn Val Val Asp Arg<br>705                         710                         715                   720 | | 2458 |
| AGG GAA GCT GTG AAG GCA AAG ATG AGG GAG AAG AAT CAT GTT GAG CAA<br>Arg Glu Ala Val Lys Ala Lys Met Arg Glu Lys Asn His Val Glu Gln | | 2506 |

```
                      725                 730                 735
TTA TCA TTG GAG TGG AGT GAA AGC ATT AGT GCT GAC AAT TCA CAA ACA       2554
Leu Ser Leu Glu Trp Ser Glu Ser Ile Ser Ala Asp Asn Ser Gln Thr
                740                 745                 750

GAA AGA GAC ATA CTT GAT GAG CTA CGC CCA CAT AAA AAC ATT AAA GCA       2602
Glu Arg Asp Ile Leu Asp Glu Leu Arg Pro His Lys Asn Ile Lys Ala
            755                 760                 765

GTT GAA ATC ACT GGA TAT AGA GGG ACA AAC TTT CCA AAC TGG GTA GCT       2650
Val Glu Ile Thr Gly Tyr Arg Gly Thr Asn Phe Pro Asn Trp Val Ala
        770                 775                 780

GAT CCT TTG TTT GTT AAG CTG GTG CAT TTG TAT CTT AGA AAC TGC AAG       2698
Asp Pro Leu Phe Val Lys Leu Val His Leu Tyr Leu Arg Asn Cys Lys
785                 790                 795                 800

GAC TGT TAC TCC TTG CCA GCA CTA GGA CAA CTC CCT TGT TTG GAA TTC       2746
Asp Cys Tyr Ser Leu Pro Ala Leu Gly Gln Leu Pro Cys Leu Glu Phe
                805                 810                 815

CTT TCC ATT AGA GGG ATG CAT GGG ATA AGA GTG GTG ACA GAA GAG TTC       2794
Leu Ser Ile Arg Gly Met His Gly Ile Arg Val Val Thr Glu Glu Phe
            820                 825                 830

TAT GGC AGA TTG TCC TCC AAA AAG CCT TTT AAC TCT CTT GTG AAG CTT       2842
Tyr Gly Arg Leu Ser Ser Lys Lys Pro Phe Asn Ser Leu Val Lys Leu
        835                 840                 845

AGA TTT GAA GAT ATG CCT GAA TGG AAG CAA TGG CAC ACA CTA GGA ATT       2890
Arg Phe Glu Asp Met Pro Glu Trp Lys Gln Trp His Thr Leu Gly Ile
850                 855                 860

GGA GAG TTC CCT ACA CTT GAG AAA CTT TCC ATT AAA AAT TGC CCT GAG       2938
Gly Glu Phe Pro Thr Leu Glu Lys Leu Ser Ile Lys Asn Cys Pro Glu
865                 870                 875                 880

CTC AGT TTG GAG ATA CCC ATC CAA TTT TCA AGT TTA AAA AGG TTA GAT       2986
Leu Ser Leu Glu Ile Pro Ile Gln Phe Ser Ser Leu Lys Arg Leu Asp
                885                 890                 895

ATA TGT GAT TGT AAG TCT GTT ACC TCC TTT CCT TTT AGC ATA CTG CCA       3034
Ile Cys Asp Cys Lys Ser Val Thr Ser Phe Pro Phe Ser Ile Leu Pro
            900                 905                 910

ACT ACC TTG AAG AGA ATA AAG ATA TCT GGT TGC CCA AAA TTG AAA TTG       3082
Thr Thr Leu Lys Arg Ile Lys Ile Ser Gly Cys Pro Lys Leu Lys Leu
        915                 920                 925

GAG GCG CCA GTT GGT GAG ATG TTT GTG GAG TAT TTG AGT GTG ATT GAT       3130
Glu Ala Pro Val Gly Glu Met Phe Val Glu Tyr Leu Ser Val Ile Asp
    930                 935                 940

TGT GGT TGT GTA GAT GAT ATA TCA CCT GAG TTT CTC CCA ACA GCA CGT       3178
Cys Gly Cys Val Asp Asp Ile Ser Pro Glu Phe Leu Pro Thr Ala Arg
945                 950                 955                 960

CAA TTG AGT ATT GAG AAT TGC CAC AAC GTT ACT AGG TTT TTG ATT CCT       3226
Gln Leu Ser Ile Glu Asn Cys His Asn Val Thr Arg Phe Leu Ile Pro
                965                 970                 975

ACT GCC ACT GAA AGT CTC CAT ATT CGG AAT TGT GAA AAA CTC TCG ATG       3274
Thr Ala Thr Glu Ser Leu His Ile Arg Asn Cys Glu Lys Leu Ser Met
            980                 985                 990

GCA TGT GGA GGA GCG GCC CAG CTG ACG TCA CTG AAT ATT TGG GGA TGT       3322
Ala Cys Gly Gly Ala Ala Gln Leu Thr Ser Leu Asn Ile Trp Gly Cys
        995                 1000                1005

AAG AAG CTC AAG TGT CTT CCA GAA CTC CTT CCA TCT CTC AAG GAA CTG       3370
Lys Lys Leu Lys Cys Leu Pro Glu Leu Leu Pro Ser Leu Lys Glu Leu
    1010                1015                1020

CGA CTG ACT TAT TGT CCA GAA ATA GAA GGA GAA TTG CCC TTC AAT TTA       3418
Arg Leu Thr Tyr Cys Pro Glu Ile Glu Gly Glu Leu Pro Phe Asn Leu
1025                1030                1035                1040

CAA ATA CTC GAT ATC AGA TAT TGC AAG AAA CTG GTG AAT GGC CGA AAG       3466
```

-continued

```
Gln Ile Leu Asp Ile Arg Tyr Cys Lys Lys Leu Val Asn Gly Arg Lys
            1045                1050                1055

GAG TGG CAT TTA CAG AGA CTC ACA GAG TTA TGG ATC AAA CAT GAT GGG       3514
Glu Trp His Leu Gln Arg Leu Thr Glu Leu Trp Ile Lys His Asp Gly
        1060                1065                1070

AGT GAC GAA CAT ATT GAA CAT TGG GAG TTG CCT TCC TCT ATT CAG AGA       3562
Ser Asp Glu His Ile Glu His Trp Glu Leu Pro Ser Ser Ile Gln Arg
        1075                1080                1085

CTA TTC ATA TTC AAT CTG AAA ACA TTA AGC AGC CAA CAT CTC AAA AGC       3610
Leu Phe Ile Phe Asn Leu Lys Thr Leu Ser Ser Gln His Leu Lys Ser
        1090                1095                1100

CTC ACC TCT CTT CAA TTT CTA CGT ATT GTT GGT AAT TTA TCT CAG TTT       3658
Leu Thr Ser Leu Gln Phe Leu Arg Ile Val Gly Asn Leu Ser Gln Phe
1105                1110                1115                1120

CAG TCA CAA GGC CAA CTT TCC TCC TTT TCT CAC CTC ACT TCG CTT CAA       3706
Gln Ser Gln Gly Gln Leu Ser Ser Phe Ser His Leu Thr Ser Leu Gln
            1125                1130                1135

ACT CTA CAA ATC TGG AAT TTT CTT AAT CTT CAA TCA CTA CCT GAA TCA       3754
Thr Leu Gln Ile Trp Asn Phe Leu Asn Leu Gln Ser Leu Pro Glu Ser
        1140                1145                1150

GCA CTG CCC TCC TCC CTC TCT CAC CTG ATC ATC TCC AAT TGC CCT AAT       3802
Ala Leu Pro Ser Ser Leu Ser His Leu Ile Ile Ser Asn Cys Pro Asn
        1155                1160                1165

CTC CAA TCC CTT CCA TTA AAA GGG ATG CCC TCT TCC CTC TCT ACA CTA       3850
Leu Gln Ser Leu Pro Leu Lys Gly Met Pro Ser Ser Leu Ser Thr Leu
        1170                1175                1180

TCA ATT TCC AAA TGT CCA TTG CTC ACA CCA CTA CTA GAA TTT GAC AAG       3898
Ser Ile Ser Lys Cys Pro Leu Leu Thr Pro Leu Leu Glu Phe Asp Lys
1185                1190                1195                1200

GGG GAA TAC TGG ACA GAA ATT GCT CAT ATC CCC ACC ATA CAG ATC GAT       3946
Gly Glu Tyr Trp Thr Glu Ile Ala His Ile Pro Thr Ile Gln Ile Asp
            1205                1210                1215

GAG GAA TGC ATG TAATGATTAA ACAAATGGC TCCCCAACTG ATGTAAGCTA            3998
Glu Glu Cys Met
            1220

TTCTTTTCCC TCATAAGCTT TTTATTTCAC TTTGCTTTTG GGGTTACTTC TTTTCATTTT     4058

TAATCATGCC GGGCTAGCTC ATCATCAAAC ACATAGCATT ATATTTAACC TCCATAGAGA     4118

ATCTAAATTT TTTAAAGGAT AATTCAATCA CAAGTTTTAG GAAATAACTG CAACTTCCAT     4178

TGTCAGATGT TATATGATTC TATGTTTCTC ATGGCTATT GGTTTATGCT CTTACCGTGT      4238

TTGAATTCAC GTCTCAATTG CCACCATGTT TAATCAAAAG TTTTTAGTTC TTGTAATCAT     4298

CAACCATCCT ATGTCACTAG CAATTTGGAT AGATAAAAGA GGTAGACAAA AAAAGCGAAA    4358

CATCTTTTTT CTTTCGTATA GCGACCAGAC GACTACATTT TGATAGGTAA GGGCTATAGA    4418

TATACATTTG CAGGGTGTTA ATCCAACGAG TTAGAAAATC CCTGTCTTTA GATATCTTCT    4478

CTTGCATATA CTTTGGCAAT TTTAAGCTAC AGTTTGAACT CATGTGTTGT TGCTAACTTA    4538

AACATGTTTT GTGCTTAATC AGATGTGGAT TTTGAAGAGC GAGTACGACA AGTCTGGTAC    4598

ATTAATTGTC CGTAGGAAGT GTTTCTAAGG TGCTGCTGCT ATTTTTACAT CTGTTCCCGA    4658

GTTTGGTTTT TTTTTTAAAT CTTTCCACTA AAGCTATTAT GTCGTCCACA GTGAATTTTC    4718

AGGTCTGTTG TTATAGGCAA GTCTTTGAGA TGCGACTATC AAAGAAGGGC GATTACAATC    4778

AGTGTACCGC TGAAACTATT TCATGTTTCC AGTGCAAGCC TCTTTTGTAA GTTGACAAAC    4838

TCGATTAGTT AATATGTTTG GGACTCAACT AGTGGTTAGA GTACTCATTT TGTAAGACTT    4898

GGTACAGAAA ATCAAATTAG AATTATCACT CGCGATGGTT GGAATAAC                 4946
```

(2) INFORMATION FOR SEQ ID NO: 2:

(i) SEQUENCE CHARACTERISTICS:
        (A) LENGTH: 1220 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Glu Ile Gly Leu Ala Ile Gly Gly Ala Phe Leu Ser Ser Ala Leu
 1               5                  10                  15

Asn Val Leu Phe Asp Arg Leu Ala Pro Asn Gly Asp Leu Leu Asn Met
            20                  25                  30

Phe Arg Lys His Thr Asp Asp Val Glu Leu Phe Glu Lys Leu Gly Asp
        35                  40                  45

Ile Leu Leu Ser Leu Gln Ile Val Leu Ser Asp Ala Glu Asn Lys Lys
    50                  55                  60

Ala Ser Asn Gln Phe Val Ser Gln Trp Leu His Lys Leu Gln Thr Ala
65                  70                  75                  80

Val Asp Ala Ala Glu Asn Leu Ile Glu Gln Val Asn Tyr Glu Ala Leu
                85                  90                  95

Arg Leu Lys Val Glu Thr Ser Asn Gln Gln Val Ser Asp Leu Asn Leu
            100                 105                 110

Cys Leu Ser Asp Asp Phe Phe Leu Asn Ile Lys Lys Lys Leu Glu Asp
        115                 120                 125

Thr Ile Lys Lys Leu Glu Val Leu Glu Lys Gln Ile Gly Arg Leu Gly
    130                 135                 140

Leu Lys Glu His Phe Ile Ser Thr Lys Gln Glu Thr Arg Thr Pro Ser
145                 150                 155                 160

Thr Ser Leu Val Asp Asp Ser Gly Ile Phe Gly Arg Lys Asn Glu Ile
                165                 170                 175

Glu Asn Leu Val Gly Arg Leu Leu Ser Met Asp Thr Lys Arg Lys Asn
            180                 185                 190

Leu Ala Val Val Pro Ile Val Gly Met Gly Gly Met Gly Lys Thr Thr
        195                 200                 205

Leu Ala Lys Ala Val Tyr Asn Asp Glu Arg Val Gln Lys His Phe Gly
    210                 215                 220

Leu Thr Ala Trp Phe Cys Val Ser Glu Ala Tyr Asp Ala Phe Arg Ile
225                 230                 235                 240

Pro Lys Gly Leu Leu Gln Glu Ile Gly Ser Thr Asp Leu Lys Ala Asp
                245                 250                 255

Asp Asn Leu Asn Gln Leu Gln Val Lys Leu Lys Ala Asp Asp Asn Leu
            260                 265                 270

Asn Gln Leu Gln Val Lys Leu Lys Glu Lys Leu Asn Gly Lys Arg Phe
        275                 280                 285

Leu Val Val Leu Asp Asp Val Trp Asn Asp Asn Tyr Pro Glu Trp Asp
    290                 295                 300

Asp Leu Arg Asn Leu Phe Leu Gln Gly Asp Ile Gly Ser Lys Ile Ile
305                 310                 315                 320

Val Thr Thr Arg Lys Glu Ser Val Ala Leu Met Met Asp Ser Gly Ala
                325                 330                 335

Ile Tyr Met Gly Ile Leu Ser Ser Glu Asp Ser Trp Ala Leu Phe Lys
            340                 345                 350

Arg His Ser Leu Glu His Lys Asp Pro Lys Glu His Pro Glu Phe Glu
```

-continued

```
            355                 360                 365
Glu Val Gly Lys Gln Ile Ala Asp Lys Cys Lys Gly Leu Pro Leu Ala
            370                 375                 380
Leu Lys Ala Leu Ala Gly Met Leu Arg Ser Lys Ser Glu Val Asp Glu
385                 390                 395                 400
Trp Arg Asn Ile Leu Arg Ser Glu Ile Trp Glu Leu Pro Ser Cys Ser
                405                 410                 415
Asn Gly Ile Leu Pro Ala Leu Met Leu Ser Tyr Asn Asp Leu Pro Ala
                420                 425                 430
His Leu Lys Gln Cys Leu Ala Tyr Cys Ala Ile Tyr Pro Lys Asp Tyr
            435                 440                 445
Gln Phe Arg Lys Glu Gln Val Ile His Leu Trp Ile Ala Asn Gly Leu
            450                 455                 460
Val His Gln Phe His Ser Gly Asn Gln Tyr Phe Ile Glu Leu Arg Ser
465                 470                 475                 480
Arg Ser Leu Phe Glu Met Ala Ser Glu Pro Ser Glu Arg Asp Val Glu
                485                 490                 495
Glu Phe Leu Met His Asp Leu Val Asn Asp Leu Ala Gln Ile Ala Ser
                500                 505                 510
Ser Asn His Cys Ile Arg Leu Glu Asp Asn Lys Gly Ser His Met Leu
            515                 520                 525
Glu Gln Cys Arg His Met Ser Tyr Ser Ile Gly Gln Asp Gly Glu Phe
            530                 535                 540
Glu Lys Leu Lys Ser Leu Phe Lys Ser Glu Gln Leu Arg Thr Leu Leu
545                 550                 555                 560
Pro Ile Asp Ile Gln Phe His Tyr Ser Lys Lys Leu Ser Lys Arg Val
                565                 570                 575
Leu His Asn Ile Leu Pro Thr Leu Arg Ser Leu Arg Ala Leu Ser Leu
                580                 585                 590
Ser His Tyr Gln Ile Glu Val Leu Pro Asn Asp Leu Phe Ile Lys Leu
            595                 600                 605
Lys Leu Leu Arg Phe Leu Asp Leu Ser Glu Thr Ser Ile Thr Lys Leu
            610                 615                 620
Pro Asp Ser Ile Phe Val Leu Tyr Asn Leu Glu Thr Leu Leu Leu Ser
625                 630                 635                 640
Ser Cys Glu Tyr Leu Glu Glu Leu Pro Leu Gln Met Glu Lys Leu Ile
                645                 650                 655
Asn Leu Arg His Leu Asp Ile Ser Asn Thr Arg Arg Leu Lys Ile Pro
                660                 665                 670
Leu His Leu Ser Arg Leu Lys Ser Leu Gln Val Leu Val Gly Ala Lys
            675                 680                 685
Phe Leu Val Gly Gly Trp Arg Met Glu Tyr Leu Gly Glu Ala Pro Asn
            690                 695                 700
Leu Tyr Gly Ser Leu Ser Ile Leu Glu Leu Glu Asn Val Val Asp Arg
705                 710                 715                 720
Arg Glu Ala Val Lys Ala Lys Met Arg Glu Lys Asn His Val Glu Gln
                725                 730                 735
Leu Ser Leu Glu Trp Ser Glu Ser Ile Ser Ala Asp Asn Ser Gln Thr
                740                 745                 750
Glu Arg Asp Ile Leu Asp Glu Leu Arg Pro His Lys Asn Ile Lys Ala
            755                 760                 765
Val Glu Ile Thr Gly Tyr Arg Gly Thr Asn Phe Pro Asn Trp Val Ala
            770                 775                 780
```

-continued

```
Asp Pro Leu Phe Val Lys Leu Val His Leu Tyr Leu Arg Asn Cys Lys
785                 790                 795                 800

Asp Cys Tyr Ser Leu Pro Ala Leu Gly Gln Leu Pro Cys Leu Glu Phe
            805                 810                 815

Leu Ser Ile Arg Gly Met His Gly Ile Arg Val Val Thr Glu Glu Phe
            820                 825                 830

Tyr Gly Arg Leu Ser Ser Lys Lys Pro Phe Asn Ser Leu Val Lys Leu
            835                 840                 845

Arg Phe Glu Asp Met Pro Glu Trp Lys Gln Trp His Thr Leu Gly Ile
850                 855                 860

Gly Glu Phe Pro Thr Leu Glu Lys Leu Ser Ile Lys Asn Cys Pro Glu
865                 870                 875                 880

Leu Ser Leu Glu Ile Pro Ile Gln Phe Ser Leu Lys Arg Leu Asp
                885                 890                 895

Ile Cys Asp Cys Lys Ser Val Thr Ser Phe Pro Phe Ser Ile Leu Pro
                900                 905                 910

Thr Thr Leu Lys Arg Ile Lys Ile Ser Gly Cys Pro Lys Leu Lys Leu
            915                 920                 925

Glu Ala Pro Val Gly Glu Met Phe Val Glu Tyr Leu Ser Val Ile Asp
930                 935                 940

Cys Gly Cys Val Asp Asp Ile Ser Pro Glu Phe Leu Pro Thr Ala Arg
945                 950                 955                 960

Gln Leu Ser Ile Glu Asn Cys His Asn Val Thr Arg Phe Leu Ile Pro
                965                 970                 975

Thr Ala Thr Glu Ser Leu His Ile Arg Asn Cys Glu Lys Leu Ser Met
            980                 985                 990

Ala Cys Gly Gly Ala Ala Gln Leu Thr Ser Leu Asn Ile Trp Gly Cys
            995                 1000                1005

Lys Lys Leu Lys Cys Leu Pro Glu Leu Leu Pro Ser Leu Lys Glu Leu
    1010                1015                1020

Arg Leu Thr Tyr Cys Pro Glu Ile Glu Gly Glu Leu Pro Phe Asn Leu
1025                1030                1035                1040

Gln Ile Leu Asp Ile Arg Tyr Cys Lys Lys Leu Val Asn Gly Arg Lys
        1045                1050                1055

Glu Trp His Leu Gln Arg Leu Thr Glu Leu Trp Ile Lys His Asp Gly
        1060                1065                1070

Ser Asp Glu His Ile Glu His Trp Glu Leu Pro Ser Ser Ile Gln Arg
        1075                1080                1085

Leu Phe Ile Phe Asn Leu Lys Thr Leu Ser Ser Gln His Leu Lys Ser
    1090                1095                1100

Leu Thr Ser Leu Gln Phe Leu Arg Ile Val Gly Asn Leu Ser Gln Phe
1105                1110                1115                1120

Gln Ser Gln Gly Gln Leu Ser Ser Phe Ser His Leu Thr Ser Leu Gln
            1125                1130                1135

Thr Leu Gln Ile Trp Asn Phe Leu Asn Leu Gln Ser Leu Pro Glu Ser
            1140                1145                1150

Ala Leu Pro Ser Ser Leu Ser His Leu Ile Ile Ser Asn Cys Pro Asn
            1155                1160                1165

Leu Gln Ser Leu Pro Leu Lys Gly Met Pro Ser Ser Leu Ser Thr Leu
    1170                1175                1180

Ser Ile Ser Lys Cys Pro Leu Leu Thr Pro Leu Leu Glu Phe Asp Lys
1185                1190                1195                1200
```

```
Gly Glu Tyr Trp Thr Glu Ile Ala His Ile Pro Thr Ile Gln Ile Asp
        1205                1210                1215

Glu Glu Cys Met
       1220

(2) INFORMATION FOR SEQ ID NO: 3:

(i) SEQUENCE CHARACTERISTICS:
        (A) LENGTH: 4465 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION:204..3923

(xi) SEQUENCE DESCRIPTION: SEQ ID NO: 3:

AAGAGGGAAA GTTTTGCTTC TTGTAGATTA GCTAGAACAT AGTTGTACTA AACAAAGAGA      60

GAGCAATCGC TGATCATTCT TGTTTGCAAA TTACTCTTAG CATTCGACAG GTAAAATAAA     120

GCTCATAACA GACACTATTT GAATATATAT TTTGTTAAAG AATCATATTG TGTTTCCTTG     180

TTTTGCTTTT GCAGATTTGA GAA ATG GAG ATT GGC TTA GCA GTT GGT GGT        230
                         Met Glu Ile Gly Leu Ala Val Gly Gly
                                         1225

GCA TTT CTC TCC TCA GCT TTG AAT GTT CTG TTT GAT AGG CTT GCT CCT      278
Ala Phe Leu Ser Ser Ala Leu Asn Val Leu Phe Asp Arg Leu Ala Pro
1230                1235                1240                1245

AAC GGT GAT CTG CTC AAC ATG TTT CGG AAG CAT AAG GAT CAT GTT AAG      326
Asn Gly Asp Leu Leu Asn Met Phe Arg Lys His Lys Asp His Val Lys
                1250                1255                1260

CTC TTA AAG AAG CTG AAA ATG ACT TTG CGT GGT ATT CAG ATT GTG CTA      374
Leu Leu Lys Lys Leu Lys Met Thr Leu Arg Gly Ile Gln Ile Val Leu
            1265                1270                1275

AGT GAT GCA GAG AAT AAG CAA GCA TCA AAT CCA TCT GTG AGA GAC TGG      422
Ser Asp Ala Glu Asn Lys Gln Ala Ser Asn Pro Ser Val Arg Asp Trp
        1280                1285                1290

CTT AAT GAG CTT CGA GAT GCT GTC GAC TCT GCT GAA AAT TTA ATA GAA      470
Leu Asn Glu Leu Arg Asp Ala Val Asp Ser Ala Glu Asn Leu Ile Glu
    1295                1300                1305

GAA GTC AAT TAT GAA GCT TTG AGG CTT AAG GTG GAA GGT CAG CAT CAG      518
Glu Val Asn Tyr Glu Ala Leu Arg Leu Lys Val Glu Gly Gln His Gln
1310                1315                1320                1325

AAC TTT TCA GAA ACA AGC AAC CAG CAA GTA AGT GAT GAA TTT TTC CTT      566
Asn Phe Ser Glu Thr Ser Asn Gln Gln Val Ser Asp Glu Phe Phe Leu
                1330                1335                1340

AAC ATA AAG GAC AAG TTG GAA GAC ACT ATT GAA ACA TTA AAG GAT TTG      614
Asn Ile Lys Asp Lys Leu Glu Asp Thr Ile Glu Thr Leu Lys Asp Leu
            1345                1350                1355

CAA GAG CAA ATT GGT CTC CTT GGC TTA AAG GAG TAT TTT GAT TCC ACG      662
Gln Glu Gln Ile Gly Leu Leu Gly Leu Lys Glu Tyr Phe Asp Ser Thr
        1360                1365                1370

AAA CTA GAA ACT AGA ACA CCT TCA ACT TCT TTG ATT GAT GAA CCA GAT      710
Lys Leu Glu Thr Arg Thr Pro Ser Thr Ser Leu Ile Asp Glu Pro Asp
    1375                1380                1385

ATC TTT GGT AGG CAG AGC GAA ATA GAG GAT TTG ATT GAC CGT CTA TTG      758
Ile Phe Gly Arg Gln Ser Glu Ile Glu Asp Leu Ile Asp Arg Leu Leu
1390                1395                1400                1405

TCT GAA GGT GCA AGT GGG AAA AAT CTG ACA GTG GTT CCT ATT GTT GGA      806
Ser Glu Gly Ala Ser Gly Lys Asn Leu Thr Val Val Pro Ile Val Gly
```

-continued

```
                    1410              1415              1420
ATG GGT GGC TTG GGC AAG ACA ACA CTT GCT AAA GCC GTA TAC AAT GAT        854
Met Gly Gly Leu Gly Lys Thr Thr Leu Ala Lys Ala Val Tyr Asn Asp
            1425              1430              1435

GAG AGT GTG AAG AAC CAT TTT GAT TTG AAA GCT TGG TTT TGT GTT TCC        902
Glu Ser Val Lys Asn His Phe Asp Leu Lys Ala Trp Phe Cys Val Ser
            1440              1445              1450

GAG GCG TAT AAT GCT TTC AGA ATA ACA AAA GGG TTA CTT CAA GAA ATT        950
Glu Ala Tyr Asn Ala Phe Arg Ile Thr Lys Gly Leu Leu Gln Glu Ile
            1455              1460              1465

GGC TCA ATT GAC TTA GTT GAT GAC AAT CTT AAT CAG CTA CAA GTC AAA        998
Gly Ser Ile Asp Leu Val Asp Asp Asn Leu Asn Gln Leu Gln Val Lys
1470              1475              1480              1485

TTG AAG GAA AGA TTA AAG GAA AAG AAG TTT CTT ATC GTT CTG GAT GAT       1046
Leu Lys Glu Arg Leu Lys Glu Lys Lys Phe Leu Ile Val Leu Asp Asp
            1490              1495              1500

GTG TGG AAT GAC AAC TAC AAC GAG TGG GAT GAA TTG AGA AAT GTT TTT       1094
Val Trp Asn Asp Asn Tyr Asn Glu Trp Asp Glu Leu Arg Asn Val Phe
            1505              1510              1515

GTA CAA GGA GAT ATA GGA AGT AAG ATC ATT GTG ACG ACA CGC AAA GAC       1142
Val Gln Gly Asp Ile Gly Ser Lys Ile Ile Val Thr Thr Arg Lys Asp
            1520              1525              1530

AGT GTT GCC TTG ATG ATG GGA AAT GAG CAA ATT AGC ATG GGC AAT TTG       1190
Ser Val Ala Leu Met Met Gly Asn Glu Gln Ile Ser Met Gly Asn Leu
            1535              1540              1545

TCT ACC GAA GCC TCT TGG TCT TTA TTT CAA AGA CAT GCA TTT GAA AAC       1238
Ser Thr Glu Ala Ser Trp Ser Leu Phe Gln Arg His Ala Phe Glu Asn
1550              1555              1560              1565

ATG GAT CCT ATG GGA CAT TCG GAA CTT GAA GAG GTT GGA AGA CAA ATT       1286
Met Asp Pro Met Gly His Ser Glu Leu Glu Glu Val Gly Arg Gln Ile
            1570              1575              1580

GCA GCT AAG TGC AAA GGA CTG CCC TTA GCT CTG AAG ACG CTT GCT GGC       1334
Ala Ala Lys Cys Lys Gly Leu Pro Leu Ala Leu Lys Thr Leu Ala Gly
            1585              1590              1595

ATG TTA CGC TCC AAA TCA GAG GTT GAA GAG TGG AAA TGT ATT CTG AGA       1382
Met Leu Arg Ser Lys Ser Glu Val Glu Glu Trp Lys Cys Ile Leu Arg
            1600              1605              1610

AGT GAA ATA TGG GAG CTG CGA GAC AAT GAC ATA TTA CCA GCG TTA ATG       1430
Ser Glu Ile Trp Glu Leu Arg Asp Asn Asp Ile Leu Pro Ala Leu Met
            1615              1620              1625

TTG AGC TAC AAT GAT CTT CCT GCA CAT TTA AAG CGA TGC TTT TCT TTT       1478
Leu Ser Tyr Asn Asp Leu Pro Ala His Leu Lys Arg Cys Phe Ser Phe
1630              1635              1640              1645

TGT GCA ATA TTT CCT AAA GAT TAT CCA TTT AGG AAA GAA CAA GTT ATT       1526
Cys Ala Ile Phe Pro Lys Asp Tyr Pro Phe Arg Lys Glu Gln Val Ile
            1650              1655              1660

CAT CTA TGG ATT GCC AAT GGT CTT GTA CCT GTG GAA GAT GAA ATA ATT       1574
His Leu Trp Ile Ala Asn Gly Leu Val Pro Val Glu Asp Glu Ile Ile
            1665              1670              1675

CAA GAT TTA GGC AAC CAA TTC TTT CTC GAG TTG AGT TCA AGA TCA TTA       1622
Gln Asp Leu Gly Asn Gln Phe Phe Leu Glu Leu Ser Ser Arg Ser Leu
            1680              1685              1690

TTT GAA AGG GTC CCA AAT CCT TCT GAA GGA AAC ATA AAG GAA TTA TTC       1670
Phe Glu Arg Val Pro Asn Pro Ser Glu Gly Asn Ile Lys Glu Leu Phe
            1695              1700              1705

CTA ATG CAT GAC CTT GTC AAT GAT TTA GCC CAA CTT GCA TCT TCA AAA       1718
Leu Met His Asp Leu Val Asn Asp Leu Ala Gln Leu Ala Ser Ser Lys
1710              1715              1720              1725

CTT TGT ATC AGG TTG GAA GAG AGC CAA GGA TCT CAT ATG TTG GAA CAA       1766
```

-continued

```
Leu Cys Ile Arg Leu Glu Glu Ser Gln Gly Ser His Met Leu Glu Gln
            1730                1735                1740

TGT CGG CAC TTA TCA TAT TCT ATG GGA TAT GAC GGT GGG TTT GAG AAA       1814
Cys Arg His Leu Ser Tyr Ser Met Gly Tyr Asp Gly Gly Phe Glu Lys
            1745                1750                1755

TTG ACA CCC CTC TAC AAA TTG GAG CAG CTG AGG ACA TTG CTT CCG ACA       1862
Leu Thr Pro Leu Tyr Lys Leu Glu Gln Leu Arg Thr Leu Leu Pro Thr
            1760                1765                1770

TGT AGT AGT GTC AAT TAT TTC TAT AAC CCT CTA ACC AAG AGG GTG TTG       1910
Cys Ser Ser Val Asn Tyr Phe Tyr Asn Pro Leu Thr Lys Arg Val Leu
            1775                1780                1785

CAT AAC ATA CTG CCT ACA CTA AGA TCC TTA AGG GCA TTA TCA TTG TCT       1958
His Asn Ile Leu Pro Thr Leu Arg Ser Leu Arg Ala Leu Ser Leu Ser
1790                1795                1800                1805

CAT TAC AAG ATG GAG GAG TTG CCA AAT GAC TTG TTT ATC AAA TTA AAG       2006
His Tyr Lys Met Glu Glu Leu Pro Asn Asp Leu Phe Ile Lys Leu Lys
                1810                1815                1820

CTC CTC AGA TTT TTG GAT ATT TCT CGG ACA AAT ATT AAA AGG TTG CCA       2054
Leu Leu Arg Phe Leu Asp Ile Ser Arg Thr Asn Ile Lys Arg Leu Pro
            1825                1830                1835

GAT TCC ATT TGT GTG TTG TAT AAC TTG GAG ACA CTT CTC CTT TCA TCT       2102
Asp Ser Ile Cys Val Leu Tyr Asn Leu Glu Thr Leu Leu Leu Ser Ser
            1840                1845                1850

TGT AAA CTT GAG GAG CTA CCG CTG CAG ATG GAG AAG TTG ATT AAC TTG       2150
Cys Lys Leu Glu Glu Leu Pro Leu Gln Met Glu Lys Leu Ile Asn Leu
            1855                1860                1865

CGT CAT CTT GAC ATA AGC AAC ACT TGG CAC TTG AAG ATG CCA CTA CAT       2198
Arg His Leu Asp Ile Ser Asn Thr Trp His Leu Lys Met Pro Leu His
1870                1875                1880                1885

CTG AGC AGG TTG AAA AGC CTC CAA GTG TTG GTG GGA GCC AAG TTT CTT       2246
Leu Ser Arg Leu Lys Ser Leu Gln Val Leu Val Gly Ala Lys Phe Leu
            1890                1895                1900

GTA GGT GTT TGG AGA ATG GAA GAT TTG GGT GAA GCA CAA AAC TTA TAT       2294
Val Gly Val Trp Arg Met Glu Asp Leu Gly Glu Ala Gln Asn Leu Tyr
            1905                1910                1915

GGA TCT CTA TCA GTT GTA AAG TTG GAA AAT GTG GTT GAT AGA AGG GAA       2342
Gly Ser Leu Ser Val Val Lys Leu Glu Asn Val Val Asp Arg Arg Glu
            1920                1925                1930

GCT GTG AAG CCA AAG ATG AGG GAG AAG AAT CAT GTT GAG CAA TTA TCA       2390
Ala Val Lys Pro Lys Met Arg Glu Lys Asn His Val Glu Gln Leu Ser
            1935                1940                1945

TTG GAG TGG AGT GAA AGC ATT AGT GCT GAC AAT TCA CAA ACA GAA AGA       2438
Leu Glu Trp Ser Glu Ser Ile Ser Ala Asp Asn Ser Gln Thr Glu Arg
1950                1955                1960                1965

GAC ATA CTT GAT GAG CTA CGC CCA CAT AAA AAT ATT CAA GAA GTC AAA       2486
Asp Ile Leu Asp Glu Leu Arg Pro His Lys Asn Ile Gln Glu Val Lys
            1970                1975                1980

ATC ATT GGA TAT AGA GGG ACA AAC TTT CCC AAT TGG GTA GCT GAT CCT       2534
Ile Ile Gly Tyr Arg Gly Thr Asn Phe Pro Asn Trp Val Ala Asp Pro
            1985                1990                1995

TTG TTT CTT AAG CTG GTG AAA TTG TCT CTT AGA AAC TGC AAG GAC TGT       2582
Leu Phe Leu Lys Leu Val Lys Leu Ser Leu Arg Asn Cys Lys Asp Cys
            2000                2005                2010

TAC TCC TTG CCA GCA CTA GGA CAA CTC CCT TGT TTG AAA TTC CTT TCC       2630
Tyr Ser Leu Pro Ala Leu Gly Gln Leu Pro Cys Leu Lys Phe Leu Ser
            2015                2020                2025

GTT AAA GGG ATG CAT GGA ATA AGA GTG GTG ACG GAA GAA TTC TAC GGC       2678
Val Lys Gly Met His Gly Ile Arg Val Val Thr Glu Glu Phe Tyr Gly
2030                2035                2040                2045
```

```
AGA TTG TCC TCC AAA AAG CCT TTT AAC TGT CTT GAG AAG CTT GAA TTT       2726
Arg Leu Ser Ser Lys Lys Pro Phe Asn Cys Leu Glu Lys Leu Glu Phe
            2050                2055                2060

GAA GAT ATG ACA GAG TGG AAG CAA TGG CAC GCA CTA GGA ATT GGA GAG       2774
Glu Asp Met Thr Glu Trp Lys Gln Trp His Ala Leu Gly Ile Gly Glu
        2065                2070                2075

TTC CCT ACA CTT GAG AAG CTT TCA ATT ATA AAT TGC CCT GAG CTC AGT       2822
Phe Pro Thr Leu Glu Lys Leu Ser Ile Ile Asn Cys Pro Glu Leu Ser
    2080                2085                2090

TTG GAG ATA CCG ATC CAA TTT TCA AGT TTA AAA AGG TTT AGG GTT TTT       2870
Leu Glu Ile Pro Ile Gln Phe Ser Ser Leu Lys Arg Phe Arg Val Phe
2095                2100                2105

GGT TGT CCA GTT GTT TTT TAT GAT GCT CAA GTG TTA AGA TCC CAA CTT       2918
Gly Cys Pro Val Val Phe Tyr Asp Ala Gln Val Leu Arg Ser Gln Leu
2110                2115                2120                2125

GAG GGA ATG AAG CAG ATT GAG GAA ATA TAT ATC CGT GAT TGT AAC TCT       2966
Glu Gly Met Lys Gln Ile Glu Glu Ile Tyr Ile Arg Asp Cys Asn Ser
        2130                2135                2140

GTT ACC TCC TTT CCT TTT AGC ATA CTG CCA ACT ACC TTG AAG ACA ATA       3014
Val Thr Ser Phe Pro Phe Ser Ile Leu Pro Thr Thr Leu Lys Thr Ile
            2145                2150                2155

GAC ATA TCT GGT TGC CCA AAA TTG AAA TTG GAG GCG CCA GTT TGT GAG       3062
Asp Ile Ser Gly Cys Pro Lys Leu Lys Leu Glu Ala Pro Val Cys Glu
        2160                2165                2170

ATG AGT ATG TTT CTG GAG GAA TTT AGT GTG GAA GAA TGT GGT TGT GTA       3110
Met Ser Met Phe Leu Glu Glu Phe Ser Val Glu Glu Cys Gly Cys Val
    2175                2180                2185

TCA CCT GAG TTT CTC CCA ACA GCA CGT GAA TTG AGA ATT GGG AAT TGC       3158
Ser Pro Glu Phe Leu Pro Thr Ala Arg Glu Leu Arg Ile Gly Asn Cys
2190                2195                2200                2205

CAC AAC GTA AGG TTT TTG ATT CCT ACT GCC ACT GAA ACT CTC CAT ATT       3206
His Asn Val Arg Phe Leu Ile Pro Thr Ala Thr Glu Thr Leu His Ile
            2210                2215                2220

CGG AAT TGT GAG AAT GTT GAA AAA CTA TCG ATG GCA TGT GGA GGA GCT       3254
Arg Asn Cys Glu Asn Val Glu Lys Leu Ser Met Ala Cys Gly Gly Ala
        2225                2230                2235

GCC CAG CTG ACA TCA CTG GAT ATT TCG GGA TGT AAG AAG CTC AAG TGT       3302
Ala Gln Leu Thr Ser Leu Asp Ile Ser Gly Cys Lys Lys Leu Lys Cys
    2240                2245                2250

CTT CCA GAA CTC CTT CCA TCT CTC AAG GAA CTG CAA CTG ACT AAT TGT       3350
Leu Pro Glu Leu Leu Pro Ser Leu Lys Glu Leu Gln Leu Thr Asn Cys
2255                2260                2265

CCA GAA ATA GAA GGA GAA TTA CCC TTC AAT TTA CAA AAA CTC TAT ATC       3398
Pro Glu Ile Glu Gly Glu Leu Pro Phe Asn Leu Gln Lys Leu Tyr Ile
2270                2275                2280                2285

AGA GAT TGC AAA AAA CTG GTG AAT GGC CGA AAG GAG TGG CAT TTA CAG       3446
Arg Asp Cys Lys Lys Leu Val Asn Gly Arg Lys Glu Trp His Leu Gln
        2290                2295                2300

AGA CTC ACA AAG TTA GTG ATC TAT CAT GAT GGG AGT GAC GAA GAT ATT       3494
Arg Leu Thr Lys Leu Val Ile Tyr His Asp Gly Ser Asp Glu Asp Ile
            2305                2310                2315

GAA CAT TGG GAG TTG CCT TGT TCT ATT ACA AGA CTT GAG GTA TTT AAT       3542
Glu His Trp Glu Leu Pro Cys Ser Ile Thr Arg Leu Glu Val Phe Asn
        2320                2325                2330

CTG ATA ACA TTA AGC AGC CAA CAT CTC AAA AGC CTC ACC TCT CTT CAA       3590
Leu Ile Thr Leu Ser Ser Gln His Leu Lys Ser Leu Thr Ser Leu Gln
    2335                2340                2345

TAT CTA TGT ATT GAT GGT AAT TTA TCT CCG ATT CAG TCA CAA GGC CAG       3638
Tyr Leu Cys Ile Asp Gly Asn Leu Ser Pro Ile Gln Ser Gln Gly Gln
2350                2355                2360                2365
```

```
ATT TCC TCC TTT TCT CAC CTC ACT TCG CTT CAA ACT CTA CAA ATC TGG      3686
Ile Ser Ser Phe Ser His Leu Thr Ser Leu Gln Thr Leu Gln Ile Trp
                2370                2375                2380

AAT TTC CAT AAT CTC CAA TCA CTT TCA GAA TCA GCA CTG CCC TCC TCC      3734
Asn Phe His Asn Leu Gln Ser Leu Ser Glu Ser Ala Leu Pro Ser Ser
            2385                2390                2395

CTC TCT CAG CTG GAG ATC TTC CAT TGC CCT AAT CTC CAA TCC CTT CCA      3782
Leu Ser Gln Leu Glu Ile Phe His Cys Pro Asn Leu Gln Ser Leu Pro
        2400                2405                2410

TTA AAC GGG ATG CCC TCT TCC CTC TCT AAA CTA TTG ATT TCA GGA TGT      3830
Leu Asn Gly Met Pro Ser Ser Leu Ser Lys Leu Leu Ile Ser Gly Cys
    2415                2420                2425

CCA TTG CTC ACA CCA CTA CTA GAA TTT GAC AAG GGG GAA TAC TGG CCA      3878
Pro Leu Leu Thr Pro Leu Leu Glu Phe Asp Lys Gly Glu Tyr Trp Pro
2430                2435                2440                2445

CAA ATT GCT CAT ATC CCC ACC ATA CTG ATC GAT TGG GAA TAT ATT          3923
Gln Ile Ala His Ile Pro Thr Ile Leu Ile Asp Trp Glu Tyr Ile
                2450                2455                2460

TAACAATTAA AACAAATGGC TCTCCAACTG ATGTAAGCTA TTTGTTACCC TCAGAAGCTT    3983

TTTATTTCAC TTTGCTTTTT TCTTAATTCT TTTCATTTTA AATCATGTCG TGCTCATCAT    4043

CAAACACATA GCTTTATAGG TAAGCTCCAT ACAGAATCTA ACTTTTTGAA AGGATAATTC    4103

GATCACAAGT TTTAGGAAAT ATCTGCAACT TCCATTGTCA GATGTTATAT GATTCTATGT    4163

TTCTCATGGC TTATTGGTTT ATGCTCTTAC CGCGTTTTCA TTCACGTCTC AATTGCCAAA    4223

GAAATCATAT GTAGCTTCTG CCACCATGTC CAATCGAAAG TTTTTAGTTC TTGTAATCAT    4283

CAACCATCCT ATGTCACTAG AAATTTGGAT AGGTAAAAGA GGTAGACAGA AAAGCTAAAC    4343

ATCTTTTTTC TTTCGTACAG CGACCAGACA ACTACATTTG GATAGGTAAG GGCTATAGAT    4403

ATACATTTGC AGGGTGTTAA TCTAACGAGT AAGGAAAATC ACTGCCTCCA GATATCTCCT    4463

CT                                                                    4465

(2) INFORMATION FOR SEQ ID NO: 4:

(i) SEQUENCE CHARACTERISTICS:
        (A) LENGTH: 1240 amino acids
        (B) TYPE: amino acid
        (D) TOPOLOGY: linear (ii) MOLECULE TYPE: protein (xi) SEQUENCE DESCRIPTION: SEQ ID NO: 4:

Met Glu Ile Gly Leu Ala Val Gly Gly Ala Phe Leu Ser Ser Ala Leu
1               5                   10                  15

Asn Val Leu Phe Asp Arg Leu Ala Pro Asn Gly Asp Leu Leu Asn Met
                20                  25                  30

Phe Arg Lys His Lys Asp His Val Lys Leu Leu Lys Lys Leu Lys Met
            35                  40                  45

Thr Leu Arg Gly Ile Gln Ile Val Leu Ser Asp Ala Glu Asn Lys Gln
        50                  55                  60

Ala Ser Asn Pro Ser Val Arg Asp Trp Leu Asn Glu Leu Arg Asp Ala
65                  70                  75                  80

Val Asp Ser Ala Glu Asn Leu Ile Glu Glu Val Asn Tyr Glu Ala Leu
                85                  90                  95

Arg Leu Lys Val Glu Gly Gln His Gln Asn Phe Ser Glu Thr Ser Asn
            100                 105                 110

Gln Gln Val Ser Asp Glu Phe Phe Leu Asn Ile Lys Asp Lys Leu Glu
```

-continued

```
               115                 120                 125
Asp Thr Ile Glu Thr Leu Lys Asp Leu Gln Glu Gln Ile Gly Leu Leu
        130                 135                 140
Gly Leu Lys Glu Tyr Phe Asp Ser Thr Lys Leu Glu Thr Arg Thr Pro
145                 150                 155                 160
Ser Thr Ser Leu Ile Asp Glu Pro Asp Ile Phe Gly Arg Gln Ser Glu
                165                 170                 175
Ile Glu Asp Leu Ile Asp Arg Leu Leu Ser Glu Gly Ala Ser Gly Lys
            180                 185                 190
Asn Leu Thr Val Val Pro Ile Val Gly Met Gly Gly Leu Gly Lys Thr
        195                 200                 205
Thr Leu Ala Lys Ala Val Tyr Asn Asp Glu Ser Val Lys Asn His Phe
210                 215                 220
Asp Leu Lys Ala Trp Phe Cys Val Ser Glu Ala Tyr Asn Ala Phe Arg
225                 230                 235                 240
Ile Thr Lys Gly Leu Leu Gln Glu Ile Gly Ser Ile Asp Leu Val Asp
                245                 250                 255
Asp Asn Leu Asn Gln Leu Gln Val Lys Leu Lys Glu Arg Leu Lys Glu
            260                 265                 270
Lys Lys Phe Leu Ile Val Leu Asp Asp Val Trp Asn Asp Asn Tyr Asn
        275                 280                 285
Glu Trp Asp Glu Leu Arg Asn Val Phe Val Gln Gly Asp Ile Gly Ser
290                 295                 300
Lys Ile Ile Val Thr Thr Arg Lys Asp Ser Val Ala Leu Met Met Gly
305                 310                 315                 320
Asn Glu Gln Ile Ser Met Gly Asn Leu Ser Thr Glu Ala Ser Trp Ser
                325                 330                 335
Leu Phe Gln Arg His Ala Phe Glu Asn Met Asp Pro Met Gly His Ser
            340                 345                 350
Glu Leu Glu Glu Val Gly Arg Gln Ile Ala Ala Lys Cys Lys Gly Leu
        355                 360                 365
Pro Leu Ala Leu Lys Thr Leu Ala Gly Met Leu Arg Ser Lys Ser Glu
370                 375                 380
Val Glu Glu Trp Lys Cys Ile Leu Arg Ser Glu Ile Trp Glu Leu Arg
385                 390                 395                 400
Asp Asn Asp Ile Leu Pro Ala Leu Met Leu Ser Tyr Asn Asp Leu Pro
                405                 410                 415
Ala His Leu Lys Arg Cys Phe Ser Phe Cys Ala Ile Phe Pro Lys Asp
            420                 425                 430
Tyr Pro Phe Arg Lys Glu Gln Val Ile His Leu Trp Ile Ala Asn Gly
        435                 440                 445
Leu Val Pro Val Glu Asp Glu Ile Ile Gln Asp Leu Gly Asn Gln Phe
450                 455                 460
Phe Leu Glu Leu Ser Ser Arg Ser Leu Phe Glu Arg Val Pro Asn Pro
465                 470                 475                 480
Ser Glu Gly Asn Ile Lys Glu Leu Phe Leu Met His Asp Leu Val Asn
                485                 490                 495
Asp Leu Ala Gln Leu Ala Ser Ser Lys Leu Cys Ile Arg Leu Glu Glu
            500                 505                 510
Ser Gln Gly Ser His Met Leu Glu Gln Cys Arg His Leu Ser Tyr Ser
        515                 520                 525
Met Gly Tyr Asp Gly Gly Phe Glu Lys Leu Thr Pro Leu Tyr Lys Leu
530                 535                 540
```

-continued

```
Glu Gln Leu Arg Thr Leu Leu Pro Thr Cys Ser Ser Val Asn Tyr Phe
545                 550                 555                 560

Tyr Asn Pro Leu Thr Lys Arg Val Leu His Asn Ile Leu Pro Thr Leu
                565                 570                 575

Arg Ser Leu Arg Ala Leu Ser Leu Ser His Tyr Lys Met Glu Glu Leu
            580                 585                 590

Pro Asn Asp Leu Phe Ile Lys Leu Lys Leu Leu Arg Phe Leu Asp Ile
        595                 600                 605

Ser Arg Thr Asn Ile Lys Arg Leu Pro Asp Ser Ile Cys Val Leu Tyr
    610                 615                 620

Asn Leu Glu Thr Leu Leu Ser Ser Cys Lys Leu Glu Glu Leu Pro
625                 630                 635                 640

Leu Gln Met Glu Lys Leu Ile Asn Leu Arg His Leu Asp Ile Ser Asn
                645                 650                 655

Thr Trp His Leu Lys Met Pro Leu His Leu Ser Arg Leu Lys Ser Leu
                660                 665                 670

Gln Val Leu Val Gly Ala Lys Phe Leu Val Gly Val Trp Arg Met Glu
            675                 680                 685

Asp Leu Gly Glu Ala Gln Asn Leu Tyr Gly Ser Leu Ser Val Val Lys
        690                 695                 700

Leu Glu Asn Val Val Asp Arg Arg Glu Ala Val Lys Pro Lys Met Arg
705                 710                 715                 720

Glu Lys Asn His Val Glu Gln Leu Ser Leu Glu Trp Ser Glu Ser Ile
                725                 730                 735

Ser Ala Asp Asn Ser Gln Thr Glu Arg Asp Ile Leu Asp Glu Leu Arg
            740                 745                 750

Pro His Lys Asn Ile Gln Glu Val Lys Ile Ile Gly Tyr Arg Gly Thr
        755                 760                 765

Asn Phe Pro Asn Trp Val Ala Asp Pro Leu Phe Leu Lys Leu Val Lys
        770                 775                 780

Leu Ser Leu Arg Asn Cys Lys Asp Cys Tyr Ser Leu Pro Ala Leu Gly
785                 790                 795                 800

Gln Leu Pro Cys Leu Lys Phe Leu Ser Val Lys Gly Met His Gly Ile
                805                 810                 815

Arg Val Val Thr Glu Glu Phe Tyr Gly Arg Leu Ser Ser Lys Lys Pro
            820                 825                 830

Phe Asn Cys Leu Glu Lys Leu Glu Phe Glu Asp Met Thr Glu Trp Lys
        835                 840                 845

Gln Trp His Ala Leu Gly Ile Gly Glu Phe Pro Thr Leu Glu Lys Leu
    850                 855                 860

Ser Ile Ile Asn Cys Pro Glu Leu Ser Leu Glu Ile Pro Ile Gln Phe
865                 870                 875                 880

Ser Ser Leu Lys Arg Phe Arg Val Phe Gly Cys Pro Val Val Phe Tyr
                885                 890                 895

Asp Ala Gln Val Leu Arg Ser Gln Leu Glu Gly Met Lys Gln Ile Glu
            900                 905                 910

Glu Ile Tyr Ile Arg Asp Cys Asn Ser Val Thr Ser Phe Pro Phe Ser
        915                 920                 925

Ile Leu Pro Thr Thr Leu Lys Thr Ile Asp Ile Ser Gly Cys Pro Lys
    930                 935                 940

Leu Lys Leu Glu Ala Pro Val Cys Glu Met Ser Met Phe Leu Glu Glu
945                 950                 955                 960
```

```
Phe Ser Val Glu Glu Cys Gly Cys Val Ser Pro Glu Phe Leu Pro Thr
            965                 970                 975

Ala Arg Glu Leu Arg Ile Gly Asn Cys His Asn Val Arg Phe Leu Ile
            980                 985                 990

Pro Thr Ala Thr Glu Thr Leu His Ile Arg Asn Cys Glu Asn Val Glu
            995                1000                1005

Lys Leu Ser Met Ala Cys Gly Gly Ala Ala Gln Leu Thr Ser Leu Asp
           1010                1015                1020

Ile Ser Gly Cys Lys Lys Leu Lys Cys Leu Pro Glu Leu Leu Pro Ser
1025                1030                1035                1040

Leu Lys Glu Leu Gln Leu Thr Asn Cys Pro Glu Ile Glu Gly Glu Leu
           1045                1050                1055

Pro Phe Asn Leu Gln Lys Leu Tyr Ile Arg Asp Cys Lys Lys Leu Val
           1060                1065                1070

Asn Gly Arg Lys Glu Trp His Leu Gln Arg Leu Thr Lys Leu Val Ile
           1075                1080                1085

Tyr His Asp Gly Ser Asp Glu Asp Ile Glu His Trp Glu Leu Pro Cys
           1090                1095                1100

Ser Ile Thr Arg Leu Glu Val Phe Asn Leu Ile Thr Leu Ser Ser Gln
1105                1110                1115                1120

His Leu Lys Ser Leu Thr Ser Leu Gln Tyr Leu Cys Ile Asp Gly Asn
           1125                1130                1135

Leu Ser Pro Ile Gln Ser Gln Gly Gln Ile Ser Ser Phe Ser His Leu
           1140                1145                1150

Thr Ser Leu Gln Thr Leu Gln Ile Trp Asn Phe His Asn Leu Gln Ser
           1155                1160                1165

Leu Ser Glu Ser Ala Leu Pro Ser Ser Leu Ser Gln Leu Glu Ile Phe
           1170                1175                1180

His Cys Pro Asn Leu Gln Ser Leu Pro Leu Asn Gly Met Pro Ser Ser
1185                1190                1195                1200

Leu Ser Lys Leu Leu Ile Ser Gly Cys Pro Leu Leu Thr Pro Leu Leu
           1205                1210                1215

Glu Phe Asp Lys Gly Glu Tyr Trp Pro Gln Ile Ala His Ile Pro Thr
           1220                1225                1230

Ile Leu Ile Asp Trp Glu Tyr Ile
           1235                1240

(2) INFORMATION FOR SEQ ID NO: 5:

(i) SEQUENCE CHARACTERISTICS:
        (A) LENGTH: 1371 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

AATTCGGCAC GAGAATTGAA ATTGGAGGCT CCAGTTGGTG AGATGTTTGT GGAGTATTTG    60

AGTGTGAATG ATTGTGGTTG TGTAGAAGAT ATATCACCTG AGTTTCTCCC AACAGCACGT   120

AAATTGATTA TTACGGATTG CCAGAACGTT ACTAGGATTT TGATTCCTAC TGCCACTGAA   180

ACTCTCACTA TTGAGAATTG TGAGAATGTT GAAAAACTAT CGGTGGCATG TGGAGGAGCG   240

GCCCAGATGA CGTCTCTGAT TATTTCGGAG TGTAAGAAGC TCAAGTGTCT TCCAGAACGT   300

ATGCAGGAAC TCCTTCCATC TCTCAAGGAA CTGCGTCTGT CTGATTGTCC AGAAATAGAA   360
```

```
GGAGAATTGC CCTTCAATTT ACAAAAACTC TATATCAGTT ATTGCAAGAA ATTGGTGAAT      420

GGCCGAAAGG AGTGGCATTT ACAGAGACTC ACAGAGTTAT GGATCCATCA TGATGGGAGT      480

GACGAAGATA TTGAACATTG GGAGTTGCCT TCCTCTATTC AGAGTCTTAC CATATGCAAT      540

CTGATAACAT TAAGCAGCCA ACATCTCAAA AGCCTCACCT CTCTTCAATA TCTATGTTTT      600

GATGGTAATT TATCTCAGAT TCAGTCACAA GGCCAGCTTT CCTCCTTTTC TCACCTCACT      660

TCGCTTCAAA CTCTACAAAT CCGTAATCTC CAATCACTTG CTGCATTAGC ACTGCCCTCC      720

TCCCTCTCTC ACCTGACCAT CCTCAATTTC CCTAATCTCC AATACTTTC AGAATCAGCA       780

CTGCCCTCCT CCCTCTCTCA CCTGATCATA GATGATTGCC CTAATCTCCA ATCACTTTCA      840

GAATCAGCAC TGCCCTCCTC CCTCTCTCAC CTGGACATCT CCAATTGCCC TAATCTCCAA      900

TCACTTTCAG AATCAGCACT GCCCTCCTCC CTCTCTAGCC TGACCATCTA TGATTGCCCT      960

AATCTCCAAT CACTTCCAGT AAAAGGGATG CCGTCTTCCC TCTCTGAACT AGCAATTTCC     1020

AAATGTCCAT TGCTCAAACC ACTACTAGAA TTTGGAAAGG GGGAATACTG GCCAAATATT     1080

GCTCATATCC CCTCCATATA CATCGATTGG GAACGCATGT AATGATTAAA ACGAATGGCT     1140

CCCCAACTGA TATGTGGATT TTGAAGAGCG AGTACGACAA GTCTGGTACA TCAATTGTCC     1200

GTAGGAAGTG TTTCTAAGTG AATTTTCAGG TTTGTTGTTA TAGGCAAGTC TTTGAGATGC     1260

GACTATCAAA GAAGGGCGAT TACGATCAGT GTACCGCTGA TATTATTTCA TGTTTCCAGT     1320

GCAAGCTTCT TTTGTAAGTT GACAAACTTG ATTAGTTCTC GTGCCGAATT C              1371

(2) INFORMATION FOR SEQ ID NO: 6:

(i) SEQUENCE CHARACTERISTICS:
        (A) LENGTH: 2027 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

CCAGGGTTTT CCCAGTCACG ACGTTGTAAA ACGACGGCCA GTGAATTGTA ATACGACTCA       60

CTATAGGGCG AATTGGAGCT CCACCGCGGT GGCGGCCGCT CTAGAACTAG TGGATCCCCC      120

CGGGCTGCAG GAATTCTATG GCAGATTGTC CTCCAAAAAG CCTTTTAACT GTCTTGAGAA      180

GCTTGAATTT GAAGATATGA CGGGGTGGAA GCAATGGCAC GCACTAGGAA TTGGAGAGTT      240

CCCTACACTT GAGAACCTTT CCATTAAAAA TTGCCCTGAG CTCAGTTTGA AGATACCCAT      300

CCAATTTTCA AGTTTAAAAA GGTTACAAGT TAGAGGTTGT CCAGTTGTTT TTGATGATGC      360

TCAACTGTTT AGATCCCAAC TTGAAGCAAT GAAGCAGATT GAAGCATTAT ATATACGTGA      420

TTGTAACTCT ATTACCTCCT TTCCTTTTAG CATACTGCCA ACTACCTTGA AGACAATAGA      480

GATATCTGGT TGCCCAAAAT TGAAATTCGA GGCGCCAGTT GGTGAGATGT TTGTGGAGTA      540

TTTGAGTGTG ATTGATTGTG GTTGTGTAGA TGATAATATC ATTAGAGTTT CTCCCAGCAG      600

CGTGTAAATT GAGTATTATG AGTTGCCACA ACTTTACTAG GTTTTTGATT CCTACTGCAA      660

CTGAAACTCT CACTATTTCG AATTGTGAGA ATGTTGAAAA ACTATCGGTG GCATGTGGAG      720

GAGCGGCCCA GATGACGTTA CTGCATATTT TGAAGTGTAA GAAGCTCAAG TGTCTGCCAG      780

AACGTATGCA GGAACTCCTT CCATCTCTCA AGGATTTGTA TCTTTCCAAT TGTCCAGAAA      840

TAGAAGGAGA ATTGCCCTTC AATTTACATA AACTCCGTAT CAGTGATTGC AAGAAACTGG      900

TGAATGGCCG AAAGGAGTGG CATTTACAGA GACTCACAGA GTTAGTGATC CATCATGATG      960
```

-continued

```
GGAGTGACGA AGATATTGAA CATTGGGAGT TGCCTTGTTC TATTACAGAA CTTGAGGGTA    1020

TACAATATGA TAACATTAAG CAGCCAACAT CTCAAAAGCC TCACCTCTCT TCAATGTCTA    1080

AGTATTGGTG GTAATTTATC TCAGATTGGC CGTCTTTCCT CCTTTTCTCA CCTCACTTCG    1140

CTTCAAACTC TACAAATCAG GAATTTCGGT AATCTCCAAT CACTTGCTGA ATCAGCACTG    1200

CCATCCTCCC TCTCTCACCT GACCATCTCC CGTTGCCCGA ATCTCCAATC ACTTGCTGAA    1260

TCAGCACTGC CCTCCTCCCT CTCTCACCTG AACATCTATG ATTGCCCGAA TCTCCAATTA    1320

CTACCTGAAT CAGCACTGCC CTCCTCCCTC TCTCACCTGG ACATCTCCCA TTGTCCTAAT    1380

CTCCAATCAC TACCTGAATC AGCACTGCTC TCCTCCCTCT CTCACCTGGA CATCTCCCAC    1440

TGTCCTAATC TCCAATCACT TGCTGAATCA GCACTGCCCT CCTCCCTCTC TCACCTGACC    1500

ATCTCCCATT GCCCTAATCT CCATTCACTT TCAGAAAAAG GGATGCCCTC TTCCCTCTCT    1560

AAACTATCTA TTTCCAAATG TTCATTGCTC ACACCACTAC TAGAATTTAA CAAGGGGGAA    1620

TACTGGACAA ATATTGCTCA TATCTCCACC ATACAGATCG ATTGGAAATG CATGTAATGA    1680

TTAAAACGAA TGACTCCCCA ACTGATATGT GGATTTAGAA GAGCGAGTAC GACAAGTCTG    1740

GTACATCAAT TGTCCGTAGG AAGTGTTTCT AAGTGAATTT TCAGGTCTGT TGTTATAGGC    1800

AAGTCTTTGA GATGTGACTA TCAAAGAAGG GCGATTACAA TCAGTGTACC GCTGATACTA    1860

TTTCATGTTT CCAGTGCTAC AGTGCAAGCC TCTTTTGTAA GTTGNCAAAC TCGATTAGTT    1920

AATATGTTTG GGACTCAACT ACTACTCATT TTGTAAGACT TAAGTACAGA AAATCAAATT    1980

AGAATTATAA CTCGCGATGG TTGAGTAAAC TCCAAGAAGC TCGTGCC                 2027
```

(2) INFORMATION FOR SEQ ID NO: 7:

(i) SEQUENCE CHARACTERISTICS:
        (A) LENGTH: 907 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 7:

```
Met Asp Phe Ile Ser Ser Leu Ile Val Gly Cys Ala Gln Val Leu Cys
1               5                   10                  15

Glu Ser Met Asn Met Ala Glu Arg Arg Gly His Lys Thr Asp Leu Arg
            20                  25                  30

Gln Ala Ile Thr Asp Leu Glu Thr Ala Ile Gly Asp Leu Lys Ala Ile
        35                  40                  45

Arg Asp Asp Leu Thr Leu Arg Ile Gln Gln Asp Gly Leu Glu Gly Arg
    50                  55                  60

Ser Cys Ser Asn Arg Ala Arg Glu Trp Leu Ser Ala Val Gln Val Thr
65                  70                  75                  80

Glu Thr Lys Thr Ala Leu Leu Leu Val Arg Phe Arg Arg Glu Gln
                85                  90                  95

Arg Thr Arg Met Arg Arg Arg Tyr Leu Ser Cys Phe Gly Cys Ala Asp
                100                 105                 110

Tyr Lys Leu Cys Lys Lys Val Ser Ala Ile Leu Lys Ser Ile Gly Glu
            115                 120                 125

Leu Arg Glu Arg Ser Glu Ala Ile Lys Thr Asp Gly Gly Ser Ile Gln
        130                 135                 140

Val Thr Cys Arg Glu Ile Pro Ile Asp Ser Val Val Gly Asn Thr Thr
145                 150                 155                 160
```

-continued

```
Met Met Glu Gln Val Leu Glu Phe Leu Ser Glu Glu Glu Arg Gly
             165                 170                 175

Ile Ile Gly Val Tyr Gly Pro Gly Val Gly Lys Thr Thr Leu Met
             180                 185                 190

Gln Ser Ile Asn Asn Glu Leu Ile Thr Lys Gly His Gln Tyr Asp Val
             195                 200                 205

Leu Ile Trp Val Gln Met Ser Arg Glu Phe Gly Glu Cys Thr Ile Gln
    210                 215                 220

Gln Ala Val Gly Ala Arg Leu Gly Leu Ser Trp Asp Glu Lys Glu Thr
225                 230                 235                 240

Gly Glu Asn Arg Ala Leu Lys Ile Tyr Arg Ala Leu Arg Gln Lys Arg
                245                 250                 255

Phe Leu Leu Leu Leu Asp Asp Val Trp Glu Glu Ile Asp Leu Glu Lys
                260                 265                 270

Thr Gly Val Pro Arg Pro Asp Arg Glu Asn Lys Cys Lys Val Met Phe
            275                 280                 285

Thr Thr Arg Ser Ile Ala Leu Cys Asn Asn Met Gly Ala Glu Tyr Lys
    290                 295                 300

Leu Arg Val Glu Phe Leu Glu Lys Lys His Ala Trp Glu Leu Phe Cys
305                 310                 315                 320

Ser Lys Val Trp Arg Lys Asp Leu Leu Glu Ser Ser Ile Arg Arg
                325                 330                 335

Leu Ala Glu Ile Leu Val Ser Lys Cys Gly Gly Leu Pro Leu Ala Leu
            340                 345                 350

Ile Thr Leu Gly Gly Ala Met Ala His Arg Glu Thr Glu Glu Glu Trp
    355                 360                 365

Ile His Ala Ser Glu Val Leu Thr Arg Phe Pro Ala Glu Met Lys Gly
    370                 375                 380

Met Asn Tyr Val Phe Ala Leu Leu Lys Phe Ser Tyr Asp Asn Leu Glu
385                 390                 395                 400

Ser Asp Leu Leu Arg Ser Cys Phe Leu Tyr Cys Ala Leu Phe Pro Glu
                405                 410                 415

Glu His Ser Ile Glu Ile Glu Gln Leu Val Glu Tyr Trp Val Gly Glu
            420                 425                 430

Gly Phe Leu Thr Ser Ser His Gly Val Asn Thr Ile Tyr Lys Gly Tyr
            435                 440                 445

Phe Leu Ile Gly Asp Leu Lys Ala Ala Cys Leu Leu Glu Thr Gly Asp
    450                 455                 460

Glu Lys Thr Gln Val Lys Met His Asn Val Glu Arg Ser Phe Ala Leu
465                 470                 475                 480

Trp Met Ala Ser Glu Gln Gly Thr Tyr Lys Glu Leu Ile Leu Val Glu
                485                 490                 495

Pro Ser Met Gly His Thr Glu Ala Pro Lys Ala Glu Asn Trp Arg Gln
            500                 505                 510

Ala Leu Val Ile Ser Leu Leu Asp Asn Arg Ile Gln Thr Leu Pro Glu
            515                 520                 525

Lys Leu Ile Cys Pro Lys Leu Thr Thr Leu Met Leu Gln Gln Asn Ser
    530                 535                 540

Ser Leu Lys Lys Ile Pro Thr Gly Phe Met His Met Pro Val Leu Arg
545                 550                 555                 560

Val Leu Asp Leu Ser Phe Thr Ser Ile Thr Glu Ile Pro Leu Ser Ile
                565                 570                 575

Lys Tyr Leu Val Glu Leu Tyr His Leu Ser Met Ser Gly Thr Lys Ile
```

```
              580                 585                 590
Ser Val Leu Pro Gln Glu Leu Gly Asn Leu Arg Lys Leu Lys His Leu
            595                 600                 605

Asp Leu Gln Arg Thr Gln Phe Leu Gln Thr Ile Pro Arg Asp Ala Ile
            610                 615                 620

Cys Trp Leu Ser Lys Leu Glu Val Leu Asn Leu Tyr Tyr Ser Tyr Ala
625                 630                 635                 640

Gly Trp Glu Leu Gln Ser Phe Gly Asp Glu Ala Glu Glu Leu Gly
            645                 650                 655

Phe Ala Asp Leu Glu Tyr Leu Glu Asn Leu Thr Thr Leu Gly Ile Thr
            660                 665                 670

Val Leu Ser Leu Glu Thr Leu Lys Thr Leu Phe Glu Phe Gly Ala Leu
            675                 680                 685

His Lys His Ile Gln His Leu His Val Glu Glu Cys Asn Glu Leu Leu
            690                 695                 700

Tyr Phe Asn Leu Pro Ser Leu Thr Asn His Gly Arg Asn Leu Arg Arg
705                 710                 715                 720

Leu Ser Ile Lys Ser Cys His Asp Leu Glu Tyr Leu Val Thr Pro Ala
                725                 730                 735

Asp Phe Glu Asn Asp Trp Leu Pro Ser Leu Glu Val Leu Thr Leu His
            740                 745                 750

Ser Leu His Asn Leu Thr Arg Val Trp Gly Asn Ser Val Ser Gln Asp
            755                 760                 765

Cys Leu Arg Asn Ile Arg Cys Ile Asn Ile Ser His Cys Asn Lys Leu
770                 775                 780

Lys Asn Val Ser Trp Val Gln Lys Leu Pro Lys Leu Glu Val Ile Glu
785                 790                 795                 800

Leu Phe Asp Cys Arg Glu Ile Glu Glu Leu Ile Ser Glu His Glu Ser
                805                 810                 815

Pro Val Glu Asp Pro Thr Leu Phe Pro Ser Leu Lys Thr Leu Arg Thr
            820                 825                 830

Arg Asp Leu Pro Glu Leu Asn Ser Ile Leu Pro Ser Arg Phe Ser Phe
            835                 840                 845

Gln Lys Val Glu Thr Leu Val Ile Thr Asn Cys Pro Arg Val Lys Lys
850                 855                 860

Leu Pro Phe Gln Glu Arg Arg Thr Gln Met Asn Leu Pro Thr Val Tyr
865                 870                 875                 880

Cys Glu Glu Lys Trp Trp Lys Ala Leu Glu Lys Asp Gln Pro Asn Glu
                885                 890                 895

Glu Leu Cys Tyr Leu Pro Arg Phe Val Pro Asn
            900                 905

(2) INFORMATION FOR SEQ ID NO: 8:

(i) SEQUENCE CHARACTERISTICS:
        (A) LENGTH: 920 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 8:

Met Ala Ser Ala Thr Val Asp Phe Gly Ile Gly Arg Ile Leu Ser Val
1               5                  10                  15

Leu Glu Asn Glu Thr Leu Leu Leu Ser Gly Val His Gly Glu Ile Lys
```

-continued

```
                20                  25                  30
Met Lys Lys Glu Leu Leu Ile Met Lys Ser Phe Leu Glu Asp Thr His
                35                  40                  45
Lys His Gly Gly Asn Gly Ser Thr Thr Thr Thr Gln Leu Phe Gln
 50                  55                  60
Thr Phe Val Ala Asn Thr Arg Asp Leu Ala Tyr Gln Ile Glu Asp Ile
 65                  70                  75                  80
Leu Asp Glu Phe Gly Tyr His Ile His Gly Tyr Arg Ser Cys Ala Lys
                 85                  90                  95
Ile Trp Arg Ala Phe His Phe Pro Arg Tyr Met Trp Ala Arg His Ser
                100                 105                 110
Ile Ala Gln Lys Leu Gly Met Val Asn Val Met Ile Gln Ser Ile Ser
                115                 120                 125
Asp Ser Met Lys Arg Tyr Tyr His Ser Glu Asn Tyr Gln Ala Ala Leu
130                 135                 140
Leu Pro Pro Ile Asp Asp Gly Asp Ala Lys Trp Val Asn Asn Ile Ser
145                 150                 155                 160
Glu Ser Ser Leu Phe Phe Ser Glu Asn Ser Leu Val Gly Ile Asp Ala
                165                 170                 175
Pro Lys Gly Lys Leu Ile Gly Arg Leu Leu Ser Pro Glu Pro Gln Arg
                180                 185                 190
Ile Val Val Ala Val Val Gly Met Gly Gly Ser Gly Lys Thr Thr Leu
                195                 200                 205
Ser Ala Asn Ile Phe Lys Ser Gln Ser Val Arg Arg His Phe Glu Ser
                210                 215                 220
Tyr Ala Trp Val Thr Ile Ser Lys Ser Tyr Val Ile Glu Asp Val Phe
225                 230                 235                 240
Arg Thr Met Ile Lys Glu Phe Tyr Lys Glu Ala Asp Thr Gln Ile Pro
                245                 250                 255
Ala Glu Leu Tyr Ser Leu Gly Tyr Arg Glu Leu Val Glu Lys Leu Val
                260                 265                 270
Glu Tyr Leu Gln Ser Lys Arg Tyr Ile Val Val Leu Asp Asp Val Trp
                275                 280                 285
Thr Thr Gly Leu Trp Arg Glu Ile Ser Ile Ala Leu Pro Asp Gly Ile
                290                 295                 300
Tyr Gly Ser Arg Val Met Met Thr Thr Arg Asp Met Asn Val Ala Ser
305                 310                 315                 320
Phe Pro Tyr Gly Ile Gly Ser Thr Lys His Glu Ile Glu Leu Leu Lys
                325                 330                 335
Glu Asp Glu Ala Trp Val Leu Phe Ser Asn Lys Ala Phe Pro Ala Ser
                340                 345                 350
Leu Glu Gln Cys Arg Thr Gln Asn Leu Glu Pro Ile Ala Arg Lys Leu
                355                 360                 365
Val Glu Arg Cys Gly Leu Pro Leu Ala Ile Ala Ser Leu Gly Ser Met
                370                 375                 380
Met Ser Thr Lys Lys Phe Glu Ser Glu Trp Lys Val Tyr Ser Thr
385                 390                 395                 400
Leu Asn Trp Glu Leu Asn Asn Asn His Glu Leu Lys Ile Val Arg Ser
                405                 410                 415
Ile Met Phe Leu Ser Phe Asn Asp Leu Pro Tyr Pro Leu Lys Arg Cys
                420                 425                 430
Phe Leu Tyr Cys Ser Leu Phe Pro Val Asn Tyr Arg Met Lys Arg Lys
                435                 440                 445
```

-continued

```
Arg Leu Ile Arg Met Trp Met Ala Gln Arg Phe Val Glu Pro Ile Arg
    450                 455                 460
Gly Val Lys Ala Glu Val Ala Asp Ser Tyr Leu Asn Glu Leu Val
465                 470                 475                 480
Tyr Arg Asn Met Leu Gln Val Ile Leu Trp Asn Pro Phe Gly Arg Pro
                485                 490                 495
Lys Ala Phe Lys Met His Asp Val Ile Trp Glu Ile Ala Leu Ser Val
                500                 505                 510
Ser Lys Leu Glu Arg Phe Cys Asp Val Tyr Asn Asp Ser Asp Gly
                515                 520                 525
Asp Asp Ala Ala Glu Thr Met Glu Asn Tyr Gly Ser Arg His Leu Cys
530                 535                 540
Ile Gln Lys Glu Met Thr Pro Asp Ser Ile Arg Ala Thr Asn Leu His
545                 550                 555                 560
Ser Leu Leu Val Cys Ser Ser Ala Lys His Lys Met Glu Leu Leu Pro
                565                 570                 575
Ser Leu Asn Leu Leu Arg Ala Leu Asp Leu Glu Asp Ser Ser Ile Ser
                580                 585                 590
Lys Leu Pro Asp Cys Leu Val Thr Met Phe Asn Leu Lys Tyr Leu Asn
                595                 600                 605
Leu Ser Lys Thr Gln Val Lys Glu Leu Pro Lys Asn Phe His Lys Leu
                610                 615                 620
Val Asn Leu Glu Thr Leu Asn Thr Lys His Ser Lys Ile Glu Glu Leu
625                 630                 635                 640
Pro Leu Gly Met Trp Lys Leu Lys Lys Leu Arg Tyr Leu Ile Thr Phe
                645                 650                 655
Arg Arg Asn Glu Gly His Asp Ser Asn Trp Asn Tyr Val Leu Gly Thr
                660                 665                 670
Arg Val Val Pro Lys Ile Trp Gln Leu Lys Asp Leu Gln Val Met Asp
                675                 680                 685
Cys Phe Asn Glu Asp Glu Leu Ile Lys Asn Leu Gly Cys Met Thr Gln
                690                 695                 700
Leu Thr Arg Ile Ser Leu Val Met Val Arg Arg Glu His Gly Arg Asp
705                 710                 715                 720
Leu Cys Asp Ser Leu Asn Lys Ile Lys Arg Ile Arg Phe Leu Ser Leu
                725                 730                 735
Thr Ser Ile Asp Glu Glu Pro Leu Glu Ile Asp Asp Leu Ala Thr
                740                 745                 750
Ala Ser Ile Glu Lys Leu Phe Leu Ala Gly Lys Leu Glu Arg Val Pro
                755                 760                 765
Ser Trp Phe Asn Thr Leu Gln Asn Leu Thr Tyr Leu Gly Leu Arg Gly
                770                 775                 780
Ser Gln Leu Gln Glu Asn Ala Ile Leu Ser Ile Gln Thr Leu Pro Arg
785                 790                 795                 800
Leu Val Trp Leu Ser Phe Tyr Asn Ala Tyr Met Gly Pro Arg Leu Arg
                805                 810                 815
Phe Ala Gln Gly Phe Gln Asn Leu Lys Ile Leu Glu Ile Val Gln Met
                820                 825                 830
Lys His Leu Thr Glu Val Val Ile Glu Asp Gly Ala Met Phe Glu Leu
                835                 840                 845
Gln Lys Leu Tyr Val Arg Ala Cys Arg Gly Leu Glu Tyr Val Pro Arg
                850                 855                 860
```

-continued

```
Gly Ile Glu Asn Leu Ile Asn Leu Gln Glu Leu His Leu Ile His Val
865                 870                 875                 880

Ser Asn Gln Leu Val Glu Arg Ile Arg Gly Glu Gly Ser Val Asp Ser
                885                 890                 895

Arg Val His Ile Pro Ala Ile Lys His Tyr Phe Arg Thr Asp Asn Gly
                900                 905                 910

Ser Phe Tyr Val Ser Leu Ser Ser
                915                 920
```

(2) INFORMATION FOR SEQ ID NO: 9:

(i) SEQUENCE CHARACTERISTICS:
        (A) LENGTH: 1144 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 9:

```
Met Ala Ser Ser Ser Ser Ser Arg Trp Ser Tyr Asp Val Phe Leu
1               5                   10                  15

Ser Phe Arg Gly Glu Asp Thr Arg Lys Thr Phe Thr Ser His Leu Tyr
                20                  25                  30

Glu Val Leu Asn Asp Lys Gly Ile Lys Thr Phe Gln Asp Asp Lys Arg
                35                  40                  45

Leu Glu Tyr Gly Ala Thr Ile Pro Gly Glu Leu Cys Lys Ala Ile Glu
50                  55                  60

Glu Ser Gln Phe Ala Ile Val Val Phe Ser Glu Asn Tyr Ala Thr Ser
65                  70                  75                  80

Arg Trp Cys Leu Asn Glu Leu Val Lys Ile Met Glu Cys Lys Thr Arg
                85                  90                  95

Phe Lys Gln Thr Val Ile Pro Ile Phe Tyr Asp Val Asp Pro Ser His
                100                 105                 110

Val Arg Asn Gln Lys Glu Ser Phe Ala Lys Ala Phe Glu Glu His Glu
                115                 120                 125

Thr Lys Tyr Lys Asp Asp Val Glu Gly Ile Gln Arg Trp Arg Ile Ala
                130                 135                 140

Leu Asn Glu Ala Ala Asn Leu Lys Gly Ser Cys Asp Asn Arg Asp Lys
145                 150                 155                 160

Thr Asp Ala Asp Cys Ile Arg Gln Ile Val Asp Gln Ile Ser Ser Lys
                165                 170                 175

Leu Cys Lys Ile Ser Leu Ser Tyr Leu Gln Asn Ile Val Gly Ile Asp
                180                 185                 190

Thr His Leu Glu Lys Ile Glu Ser Leu Leu Glu Ile Gly Ile Asn Gly
                195                 200                 205

Val Arg Ile Met Gly Ile Trp Gly Met Gly Gly Val Gly Lys Thr Thr
                210                 215                 220

Ile Ala Arg Ala Ile Phe Asp Thr Leu Leu Gly Arg Met Asp Ser Ser
225                 230                 235                 240

Tyr Gln Phe Asp Gly Ala Cys Phe Leu Lys Asp Ile Lys Glu Asn Lys
                245                 250                 255

Arg Gly Met His Ser Leu Gln Asn Ala Leu Leu Ser Glu Leu Leu Arg
                260                 265                 270

Glu Lys Ala Asn Tyr Asn Asn Glu Glu Asp Gly Lys His Gln Met Ala
                275                 280                 285
```

```
Ser Arg Leu Arg Ser Lys Lys Val Leu Ile Val Leu Asp Asp Ile Asp
    290                 295                 300

Asn Lys Asp His Tyr Leu Glu Tyr Leu Ala Gly Asp Leu Asp Trp Phe
305                 310                 315                 320

Gly Asn Gly Ser Arg Ile Ile Ile Thr Thr Arg Asp Lys His Leu Ile
                325                 330                 335

Glu Lys Asn Asp Ile Ile Tyr Glu Val Thr Ala Leu Pro Asp His Glu
                340                 345                 350

Ser Ile Gln Leu Phe Lys Gln His Ala Phe Gly Lys Glu Val Pro Asn
                355                 360                 365

Glu Asn Phe Glu Lys Leu Ser Leu Glu Val Val Asn Tyr Ala Lys Gly
        370                 375                 380

Leu Pro Leu Ala Leu Lys Val Trp Gly Ser Leu Leu His Asn Leu Arg
385                 390                 395                 400

Leu Thr Glu Trp Lys Ser Ala Ile Glu His Met Lys Asn Asn Ser Tyr
                405                 410                 415

Ser Gly Ile Ile Asp Lys Leu Lys Ile Ser Tyr Asp Gly Leu Glu Pro
                420                 425                 430

Lys Gln Gln Glu Met Phe Leu Asp Ile Ala Cys Phe Leu Arg Gly Glu
        435                 440                 445

Glu Lys Asp Tyr Ile Leu Gln Ile Leu Glu Ser Cys His Ile Gly Ala
        450                 455                 460

Glu Tyr Gly Leu Arg Ile Leu Ile Asp Lys Ser Leu Val Phe Ile Ser
465                 470                 475                 480

Glu Tyr Asn Gln Val Gln Met His Asp Leu Ile Gln Asp Met Gly Lys
                485                 490                 495

Tyr Ile Val Asn Phe Gln Lys Asp Pro Gly Glu Arg Ser Arg Leu Trp
                500                 505                 510

Leu Ala Lys Glu Val Glu Glu Val Met Ser Asn Asn Thr Gly Thr Met
                515                 520                 525

Ala Met Glu Ala Ile Met Val Ser Ser Tyr Ser Ser Thr Leu Arg Phe
                530                 535                 540

Ser Asn Gln Ala Val Lys Asn Met Lys Arg Leu Arg Val Phe Asn Met
545                 550                 555                 560

Gly Arg Ser Ser Thr His Tyr Ala Ile Asp Tyr Leu Pro Asn Asn Leu
                565                 570                 575

Arg Cys Phe Val Cys Thr Asn Tyr Pro Trp Glu Ser Phe Pro Ser Thr
                580                 585                 590

Phe Glu Leu Lys Met Leu Val His Leu Gln Leu Arg His Asn Ser Leu
        595                 600                 605

Arg His Leu Trp Thr Glu Thr Lys His Leu Pro Ser Leu Arg Arg Ile
        610                 615                 620

Leu Leu Ser Trp Ser Lys Arg Leu Thr Arg Thr Pro Asp Phe Thr Gly
625                 630                 635                 640

Met Pro Asn Leu Glu Tyr Val Asn Leu Tyr Gln Cys Ser Asn Leu Glu
                645                 650                 655

Glu Val His His Ser Leu Gly Cys Cys Ser Lys Val Ile Gly Leu Tyr
                660                 665                 670

Leu Asn Asp Cys Lys Ser Leu Lys Arg Phe Pro Cys Val Asn Val Glu
                675                 680                 685

Ser Leu Glu Tyr Leu Gly Leu Arg Ser Cys Asp Ser Leu Glu Lys Leu
        690                 695                 700

Pro Glu Ile Tyr Gly Arg Met Lys Pro Glu Ile Gln Ile His Met Gln
```

-continued

```
705                 710                 715                 720

Gly Ser Gly Ile Arg Glu Leu Pro Ser Ser Ile Phe Gln Tyr Lys Thr
                725                 730                 735

His Val Thr Lys Leu Leu Leu Trp Asn Met Lys Asn Leu Val Ala Leu
                740                 745                 750

Pro Ser Ser Ile Cys Arg Leu Lys Ser Leu Val Ser Leu Ser Val Ser
                755                 760                 765

Gly Cys Ser Lys Leu Glu Ser Leu Pro Glu Glu Ile Gly Asp Leu Asp
                770                 775                 780

Asn Leu Arg Val Phe Asp Ala Ser Asp Thr Leu Ile Leu Arg Pro Pro
785                 790                 795                 800

Ser Ser Ile Ile Arg Leu Asn Lys Leu Ile Ile Leu Met Phe Arg Gly
                805                 810                 815

Phe Lys Asp Gly Val His Phe Glu Phe Pro Pro Val Ala Glu Gly Leu
                820                 825                 830

His Ser Leu Glu Tyr Leu Asn Leu Ser Tyr Cys Asn Leu Ile Asp Gly
                835                 840                 845

Gly Leu Pro Glu Glu Ile Gly Ser Leu Ser Ser Leu Lys Lys Leu Asp
                850                 855                 860

Leu Ser Arg Asn Asn Phe Glu His Leu Pro Ser Ser Ile Ala Gln Leu
865                 870                 875                 880

Gly Ala Leu Gln Ser Leu Asp Leu Lys Asp Cys Gln Arg Leu Thr Gln
                885                 890                 895

Leu Pro Glu Leu Pro Pro Glu Leu Asn Glu Leu His Val Asp Cys His
                900                 905                 910

Met Ala Leu Lys Phe Ile His Tyr Leu Val Thr Lys Arg Lys Lys Leu
                915                 920                 925

His Arg Val Lys Leu Asp Asp Ala His Asn Asp Thr Met Tyr Asn Leu
                930                 935                 940

Phe Ala Tyr Thr Met Phe Gln Asn Ile Ser Ser Met Arg His Asp Ile
945                 950                 955                 960

Ser Ala Ser Asp Ser Leu Ser Leu Thr Val Phe Thr Gly Gln Pro Tyr
                965                 970                 975

Pro Glu Lys Ile Pro Ser Trp Phe His His Gln Gly Trp Asp Ser Ser
                980                 985                 990

Val Ser Val Asn Leu Pro Glu Asn Trp Tyr Ile Pro Asp Lys Phe Leu
                995                 1000                1005

Gly Phe Ala Val Cys Tyr Ser Arg Ser Leu Ile Asp Thr Thr Ala His
                1010                1015                1020

Leu Ile Pro Val Cys Asp Asp Lys Met Ser Arg Met Thr Gln Lys Leu
1025                1030                1035                1040

Ala Leu Ser Glu Cys Asp Thr Glu Ser Ser Asn Tyr Ser Glu Trp Asp
                1045                1050                1055

Ile His Phe Phe Phe Val Pro Phe Ala Gly Leu Trp Asp Thr Ser Lys
                1060                1065                1070

Ala Asn Gly Lys Thr Pro Asn Asp Tyr Gly Ile Ile Arg Leu Ser Phe
                1075                1080                1085

Ser Gly Glu Glu Lys Met Tyr Gly Leu Arg Leu Leu Tyr Lys Glu Gly
                1090                1095                1100

Pro Glu Val Asn Ala Leu Leu Gln Met Arg Glu Asn Ser Asn Glu Pro
1105                1110                1115                1120

Thr Glu His Ser Thr Gly Ile Arg Arg Thr Gln Tyr Asn Asn Arg Thr
                1125                1130                1135
```

Ser Phe Tyr Glu Leu Ile Asn Gly
                1140

(2) INFORMATION FOR SEQ ID NO: 10:

(i) SEQUENCE CHARACTERISTICS:
        (A) LENGTH: 1294 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 10:

Met Ser Tyr Leu Arg Glu Val Ala Thr Ala Val Ala Leu Leu Leu Pro
1               5                   10                  15

Phe Ile Leu Leu Asn Lys Phe Trp Arg Pro Asn Ser Lys Asp Ser Ile
            20                  25                  30

Val Asn Asp Asp Asp Ser Thr Ser Glu Val Asp Ala Ile Ser Asp
            35                  40                  45

Ser Thr Asn Pro Ser Gly Ser Phe Pro Ser Val Glu Tyr Glu Val Phe
    50                  55                  60

Leu Ser Phe Arg Gly Pro Asp Thr Arg Glu Gln Phe Thr Asp Phe Leu
65                  70                  75                  80

Tyr Gln Ser Leu Arg Arg Tyr Lys Ile His Thr Phe Arg Asp Asp Asp
                85                  90                  95

Glu Leu Leu Lys Gly Lys Glu Ile Gly Pro Asn Leu Leu Arg Ala Ile
            100                 105                 110

Asp Gln Ser Lys Ile Tyr Val Pro Ile Ile Ser Ser Gly Tyr Ala Asp
            115                 120                 125

Ser Lys Trp Cys Leu Met Glu Leu Ala Glu Ile Val Arg Arg Gln Glu
    130                 135                 140

Glu Asp Pro Arg Arg Ile Ile Leu Pro Ile Phe Tyr Met Val Asp Pro
145                 150                 155                 160

Ser Asp Val Arg His Gln Thr Gly Cys Tyr Lys Lys Ala Phe Arg Lys
                165                 170                 175

His Ala Asn Lys Phe Asp Gly Gln Thr Ile Gln Asn Trp Lys Asp Ala
            180                 185                 190

Leu Lys Lys Val Gly Asp Leu Lys Gly Trp His Ile Gly Lys Asn Asp
            195                 200                 205

Lys Gln Gly Ala Ile Ala Asp Lys Val Ser Ala Asp Ile Trp Ser His
    210                 215                 220

Ile Ser Lys Glu Asn Leu Ile Leu Glu Thr Asp Glu Leu Val Gly Asn
225                 230                 235                 240

Asp Asp His Ile Thr Ala Val Leu Glu Lys Leu Ser Leu Asp Ser Glu
                245                 250                 255

Asn Val Thr Met Val Gly Leu Tyr Gly Met Gly Gly Ile Gly Lys Thr
            260                 265                 270

Thr Thr Ala Lys Ala Val Tyr Asn Lys Ile Ser Ser Cys Phe Asp Cys
            275                 280                 285

Cys Cys Phe Ile Asp Asn Ile Arg Glu Thr Gln Glu Lys Asp Gly Val
    290                 295                 300

Val Val Leu Gln Lys Lys Leu Val Ser Glu Ile Leu Arg Ile Asp Ser
305                 310                 315                 320

Gly Ser Val Gly Phe Asn Asn Asp Ser Gly Gly Arg Lys Thr Ile Lys
                325                 330                 335

```
Glu Arg Val Ser Arg Phe Lys Ile Leu Val Leu Asp Asp Val Asp
                340                 345                 350

Glu Lys Phe Lys Phe Glu Asp Met Leu Gly Ser Pro Lys Asp Phe Ile
            355                 360                 365

Ser Gln Ser Arg Phe Ile Ile Thr Ser Arg Ser Met Arg Val Leu Gly
        370                 375                 380

Thr Leu Asn Glu Asn Gln Cys Lys Leu Tyr Glu Val Gly Ser Met Ser
385                 390                 395                 400

Lys Pro Arg Ser Leu Glu Leu Phe Ser Lys His Ala Phe Lys Lys Asn
                405                 410                 415

Thr Pro Pro Ser Tyr Tyr Glu Thr Leu Ala Asn Asp Val Val Asp Thr
            420                 425                 430

Thr Ala Gly Leu Pro Leu Thr Leu Lys Val Ile Gly Ser Leu Leu Phe
        435                 440                 445

Lys Gln Glu Ile Ala Val Trp Glu Asp Thr Leu Glu Gln Leu Arg Arg
        450                 455                 460

Thr Leu Asn Leu Asp Glu Val Tyr Asp Arg Leu Lys Ile Ser Tyr Asp
465                 470                 475                 480

Ala Leu Asn Pro Glu Ala Lys Glu Ile Phe Leu Asp Ile Ala Cys Phe
                485                 490                 495

Phe Ile Gly Gln Asn Lys Glu Glu Pro Tyr Tyr Met Trp Thr Asp Cys
            500                 505                 510

Asn Phe Tyr Pro Ala Ser Asn Ile Ile Phe Leu Ile Gln Arg Cys Met
            515                 520                 525

Ile Gln Val Gly Asp Asp Asp Glu Phe Lys Met His Asp Gln Leu Arg
530                 535                 540

Asp Met Gly Arg Glu Ile Val Arg Arg Glu Met Val Leu Pro Trp Lys
545                 550                 555                 560

Arg Ser Arg Ile Trp Ser Ala Glu Gly Ile Asp Leu Leu Asn
                565                 570                 575

Lys Lys Gly Ser Ser Lys Val Lys Ala Ile Ser Ile Pro Trp Gly Val
            580                 585                 590

Lys Tyr Glu Phe Lys Ser Glu Cys Phe Leu Asn Leu Ser Glu Leu Arg
            595                 600                 605

Tyr Leu His Ala Arg Glu Ala Met Leu Thr Gly Asp Phe Asn Asn Leu
        610                 615                 620

Leu Pro Asn Leu Lys Trp Leu Glu Leu Pro Phe Tyr Lys His Gly Glu
625                 630                 635                 640

Asp Asp Pro Pro Leu Thr Asn Tyr Thr Met Lys Asn Leu Ile Ile Val
                645                 650                 655

Ile Leu Glu His Ser His Ile Thr Ala Asp Asp Trp Gly Gly Trp Arg
                660                 665                 670

His Met Met Lys Met Ala Glu Arg Leu Lys Val Val Arg Leu Ala Ser
            675                 680                 685

Asn Tyr Ser Leu Tyr Gly Arg Arg Val Arg Leu Ser Asp Cys Trp Arg
        690                 695                 700

Phe Pro Lys Ser Ile Glu Val Leu Ser Met Thr Ala Ile Glu Met Asp
705                 710                 715                 720

Glu Val Asp Ile Gly Glu Leu Lys Lys Leu Lys Thr Leu Val Leu Lys
                725                 730                 735

Phe Cys Pro Ile Gln Lys Ile Ser Gly Gly Thr Phe Gly Met Leu Lys
            740                 745                 750
```

-continued

```
Gly Leu Arg Glu Leu Cys Leu Glu Phe Asn Trp Gly Thr Asn Leu Arg
        755                 760                 765

Glu Val Val Ala Asp Ile Gly Gln Leu Ser Ser Leu Lys Val Leu Lys
    770                 775                 780

Thr Thr Gly Ala Lys Glu Val Glu Ile Asn Glu Phe Pro Leu Gly Leu
785                 790                 795                 800

Lys Glu Leu Ser Thr Ser Ser Arg Ile Pro Asn Leu Ser Gln Leu Leu
                805                 810                 815

Asp Leu Glu Val Leu Lys Val Tyr Asp Cys Lys Asp Gly Phe Asp Met
            820                 825                 830

Pro Pro Ala Ser Pro Ser Glu Asp Glu Ser Ser Val Trp Trp Lys Val
            835                 840                 845

Ser Lys Leu Lys Ser Leu Gln Leu Glu Lys Thr Arg Ile Asn Val Asn
    850                 855                 860

Val Val Asp Asp Ala Ser Ser Gly Gly His Leu Pro Arg Tyr Leu Leu
865                 870                 875                 880

Pro Thr Ser Leu Thr Tyr Leu Lys Ile Tyr Gln Cys Thr Glu Pro Thr
                885                 890                 895

Trp Leu Pro Gly Ile Glu Asn Leu Glu Asn Leu Thr Ser Leu Glu Val
            900                 905                 910

Asn Asp Ile Phe Gln Thr Leu Gly Gly Asp Leu Asp Gly Leu Gln Gly
        915                 920                 925

Leu Arg Ser Leu Glu Ile Leu Arg Ile Arg Lys Val Asn Gly Leu Ala
    930                 935                 940

Arg Ile Lys Gly Leu Lys Asp Leu Leu Cys Ser Ser Thr Cys Lys Leu
945                 950                 955                 960

Arg Lys Phe Tyr Ile Thr Glu Cys Pro Asp Leu Ile Glu Leu Leu Pro
                965                 970                 975

Cys Glu Leu Gly Val Gln Thr Val Val Val Pro Ser Met Ala Glu Leu
            980                 985                 990

Thr Ile Arg Asp Cys Pro Arg Leu Glu Val Gly Pro Met Ile Arg Ser
        995                 1000                1005

Leu Pro Lys Phe Pro Met Leu Lys Lys Leu Asp Leu Ala Val Ala Asn
    1010                1015                1020

Ile Thr Lys Glu Glu Asp Leu Asp Ala Ile Gly Ser Leu Glu Glu Leu
1025                1030                1035                1040

Val Ser Leu Glu Leu Glu Leu Asp Asp Thr Ser Ser Gly Ile Glu Arg
                1045                1050                1055

Ile Val Ser Ser Ser Lys Leu Gln Lys Leu Thr Thr Leu Val Val Lys
            1060                1065                1070

Val Pro Ser Leu Arg Glu Ile Glu Gly Leu Glu Glu Leu Lys Ser Leu
    1075                1080                1085

Gln Asp Leu Tyr Leu Glu Gly Cys Thr Ser Leu Gly Arg Leu Pro Leu
    1090                1095                1100

Glu Lys Leu Lys Glu Leu Asp Ile Gly Gly Cys Pro Asp Leu Thr Glu
1105                1110                1115                1120

Leu Val Gln Thr Val Val Ala Val Pro Ser Leu Arg Gly Leu Thr Ile
                1125                1130                1135

Arg Asp Cys Pro Arg Leu Glu Val Gly Pro Met Ile Gln Ser Leu Pro
            1140                1145                1150

Lys Phe Pro Met Leu Asn Glu Leu Thr Leu Ser Met Val Asn Ile Thr
            1155                1160                1165

Lys Glu Asp Glu Leu Glu Val Leu Gly Ser Leu Glu Glu Leu Asp Ser
```

```
            1170                1175                1180
Leu Glu Leu Thr Leu Asp Asp Thr Cys Ser Ser Ile Glu Arg Ile Ser
1185                1190                1195                1200

Phe Leu Ser Lys Leu Gln Lys Leu Thr Thr Leu Ile Val Glu Val Pro
            1205                1210                1215

Ser Leu Arg Glu Ile Glu Gly Leu Ala Glu Leu Lys Ser Leu Arg Ile
            1220                1225                1230

Leu Tyr Leu Glu Gly Cys Thr Ser Leu Glu Arg Leu Trp Pro Asp Gln
            1235                1240                1245

Gln Gln Leu Gly Ser Leu Lys Asn Leu Asn Val Leu Asp Ile Gln Gly
            1250                1255                1260

Cys Lys Ser Leu Ser Val Asp His Leu Ser Ala Leu Lys Thr Thr Leu
1265                1270                1275                1280

Pro Pro Arg Ala Arg Ile Thr Trp Pro Asp Gln Pro Tyr Arg
                1285                1290

(2) INFORMATION FOR SEQ ID NO: 11:

(i) SEQUENCE CHARACTERISTICS:
         (A) LENGTH: 373 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO: 11:

Asn Ser Ala Arg Glu Leu Lys Leu Glu Ala Pro Val Gly Glu Met Phe
1               5                   10                  15

Val Glu Tyr Leu Ser Val Asn Asp Cys Gly Cys Val Glu Asp Ile Ser
                20                  25                  30

Pro Glu Phe Leu Pro Thr Ala Arg Lys Leu Ile Ile Thr Asp Cys Gln
            35                  40                  45

Asn Val Thr Arg Ile Leu Ile Pro Thr Ala Thr Glu Thr Leu Thr Ile
        50                  55                  60

Glu Asn Cys Glu Asn Val Glu Lys Leu Ser Val Ala Cys Gly Gly Ala
65                  70                  75                  80

Ala Gln Met Thr Ser Leu Ile Ile Ser Glu Cys Lys Lys Leu Lys Cys
                85                  90                  95

Leu Pro Glu Arg Met Gln Glu Leu Leu Pro Ser Leu Lys Glu Leu Arg
            100                 105                 110

Leu Ser Asp Cys Pro Glu Ile Glu Gly Glu Leu Pro Phe Asn Leu Gln
        115                 120                 125

Lys Leu Tyr Ile Ser Tyr Cys Lys Lys Leu Val Asn Gly Arg Lys Glu
    130                 135                 140

Trp His Leu Gln Arg Leu Thr Glu Leu Trp Ile His His Asp Gly Ser
145                 150                 155                 160

Asp Glu Asp Ile Glu His Trp Glu Leu Pro Ser Ser Ile Gln Ser Leu
                165                 170                 175

Thr Ile Cys Asn Leu Ile Thr Leu Ser Ser Gln His Leu Lys Ser Leu
            180                 185                 190

Thr Ser Leu Gln Tyr Leu Cys Phe Asp Gly Asn Leu Ser Gln Ile Gln
        195                 200                 205

Ser Gln Gly Gln Leu Ser Ser Phe Ser His Leu Thr Ser Leu Gln Thr
    210                 215                 220

Leu Gln Ile Arg Asn Leu Gln Ser Leu Ala Ala Leu Ala Leu Pro Ser
```

```
                225                 230                 235                 240
Ser Leu Ser His Leu Thr Ile Leu Asn Phe Pro Asn Leu Gln Ser Leu
                245                 250                 255

Ser Glu Ser Ala Leu Pro Ser Ser Leu Ser His Leu Ile Ile Asp Asp
                260                 265                 270

Cys Pro Asn Leu Gln Ser Leu Ser Glu Ser Ala Leu Pro Ser Ser Leu
                275                 280                 285

Ser His Leu Asp Ile Ser Asn Cys Pro Asn Leu Gln Ser Leu Ser Glu
                290                 295                 300

Ser Ala Leu Pro Ser Ser Leu Ser Ser Leu Thr Ile Tyr Asp Cys Pro
305                 310                 315                 320

Asn Leu Gln Ser Leu Pro Val Lys Gly Met Pro Ser Ser Leu Ser Glu
                325                 330                 335

Leu Ala Ile Ser Lys Cys Pro Leu Leu Lys Pro Leu Leu Glu Phe Gly
                340                 345                 350

Lys Gly Glu Tyr Trp Pro Asn Ile Ala His Ile Pro Ser Ile Tyr Ile
                355                 360                 365

Asp Trp Glu Arg Met
                370

(2) INFORMATION FOR SEQ ID NO: 12:

(i) SEQUENCE CHARACTERISTICS:
        (A) LENGTH: 515 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 12:

Gln Glu Phe Tyr Gly Arg Leu Ser Ser Lys Lys Pro Phe Asn Cys Leu
1                   5                  10                  15

Glu Lys Leu Glu Phe Glu Asp Met Thr Gly Trp Lys Gln Trp His Ala
                20                  25                  30

Leu Gly Ile Gly Glu Phe Pro Thr Leu Glu Asn Leu Ser Ile Lys Asn
                35                  40                  45

Cys Pro Glu Leu Ser Leu Lys Ile Pro Ile Gln Phe Ser Ser Leu Lys
50                  55                  60

Arg Leu Gln Val Arg Gly Cys Pro Val Val Phe Asp Asp Ala Gln Leu
65                  70                  75                  80

Phe Arg Ser Gln Leu Glu Ala Met Lys Gln Ile Glu Ala Leu Tyr Ile
                85                  90                  95

Arg Asp Cys Asn Ser Ile Thr Ser Phe Pro Phe Ser Ile Leu Pro Thr
                100                 105                 110

Thr Leu Lys Thr Ile Glu Ile Ser Gly Cys Pro Lys Leu Lys Phe Glu
                115                 120                 125

Ala Pro Val Gly Glu Met Phe Val Glu Tyr Leu Ser Val Ile Asp Cys
                130                 135                 140

Gly Cys Val Asp Asp Ile Ser Leu Glu Phe Leu Pro Ala Ala Cys Lys
145                 150                 155                 160

Leu Ser Ile Met Ser Cys His Asn Phe Thr Arg Phe Leu Ile Pro Thr
                165                 170                 175

Ala Thr Glu Thr Leu Thr Ile Ser Asn Cys Glu Asn Val Glu Lys Leu
                180                 185                 190

Ser Val Ala Cys Gly Gly Ala Ala Gln Met Thr Leu Leu His Ile Leu
```

-continued

```
              195                 200                 205
Lys Cys Lys Lys Leu Lys Cys Leu Pro Glu Arg Met Gln Glu Leu Leu
        210                 215                 220

Pro Ser Leu Lys Asp Leu Tyr Leu Ser Asn Cys Pro Glu Ile Glu Gly
225                 230                 235                 240

Glu Leu Pro Phe Asn Leu His Lys Leu Arg Ile Ser Asp Cys Lys Lys
                245                 250                 255

Leu Val Asn Gly Arg Lys Glu Trp His Leu Gln Arg Leu Thr Glu Leu
                260                 265                 270

Val Ile His His Asp Gly Ser Asp Glu Asp Ile Glu His Trp Glu Leu
            275                 280                 285

Pro Cys Ser Ile Gln Asn Leu Arg Val Tyr Asn Met Ile Thr Leu Ser
        290                 295                 300

Ser Gln His Leu Lys Ser Leu Thr Ser Leu Gln Cys Phe Ser Ile Gly
305                 310                 315                 320

Gly Asn Leu Ser Gln Ile Gly Arg Leu Ser Ser Phe Ser His Leu Thr
                325                 330                 335

Ser Leu Gln Thr Leu Gln Ile Arg Asn Phe Gly Asn Leu Gln Ser Leu
            340                 345                 350

Ala Glu Ser Ala Leu Pro Ser Ser Leu Ser His Leu Thr Ile Ser Arg
            355                 360                 365

Cys Pro Asn Leu Gln Ser Leu Ala Glu Ser Ala Leu Pro Ser Ser Leu
        370                 375                 380

Ser His Leu Asn Ile Tyr Asp Cys Pro Asn Leu Gln Leu Leu Pro Glu
385                 390                 395                 400

Ser Ala Leu Pro Ser Ser Leu Ser His Leu Asp Ile Ser His Cys Pro
                405                 410                 415

Asn Leu Gln Ser Leu Pro Glu Ser Ala Leu Leu Ser Ser Leu Ser His
            420                 425                 430

Leu Asp Ile Ser His Cys Pro Asn Leu Gln Ser Leu Ala Glu Ser Ala
        435                 440                 445

Leu Pro Ser Ser Leu Ser His Leu Thr Ile Ser His Cys Pro Asn Leu
    450                 455                 460

His Ser Leu Ser Glu Lys Gly Met Pro Ser Ser Leu Ser Lys Leu Ser
465                 470                 475                 480

Ile Ser Lys Cys Ser Leu Leu Thr Pro Leu Leu Glu Phe Asn Lys Gly
                485                 490                 495

Glu Tyr Trp Thr Asn Ile Ala His Ile Ser Thr Ile Gln Ile Asp Trp
            500                 505                 510

Lys Cys Met
        515
```